(12) United States Patent
Negishi

(10) Patent No.: US 10,000,432 B2
(45) Date of Patent: Jun. 19, 2018

(54) PROCESSES FOR THE SYNTHESIS OF CHIRAL 1-ALKANOLS

(71) Applicant: PURDUE RESEARCH FOUNDATION, West Lafayette, IN (US)

(72) Inventor: Ei-ichi Negishi, West Lafayette, IN (US)

(73) Assignee: PURDUE RESEARCH FOUNDATION, West Lafayette, IN (US)

( * ) Notice: Subject to any disclaimer, the term of this patent is extended or adjusted under 35 U.S.C. 154(b) by 7 days.

(21) Appl. No.: 15/111,449

(22) PCT Filed: Jan. 9, 2015

(86) PCT No.: PCT/US2015/010720
§ 371 (c)(1),
(2) Date: Jul. 13, 2016

(87) PCT Pub. No.: WO2015/106045
PCT Pub. Date: Jul. 16, 2015

(65) Prior Publication Data
US 2016/0332940 A1  Nov. 17, 2016

Related U.S. Application Data

(60) Provisional application No. 61/926,584, filed on Jan. 13, 2014.

(51) Int. Cl.
| | | |
|---|---|---|
| C12P 17/06 | (2006.01) |
| C07C 29/50 | (2006.01) |
| C07C 29/44 | (2006.01) |
| C07F 5/06 | (2006.01) |
| C07C 67/03 | (2006.01) |
| C07C 29/62 | (2006.01) |
| C07C 67/317 | (2006.01) |
| C07C 67/343 | (2006.01) |
| C07C 69/734 | (2006.01) |
| C07C 41/26 | (2006.01) |
| C07C 51/295 | (2006.01) |
| C07C 29/09 | (2006.01) |
| C07C 29/10 | (2006.01) |
| C07D 319/06 | (2006.01) |
| C12P 7/62 | (2006.01) |

(52) U.S. Cl.
CPC ............ *C07C 29/50* (2013.01); *C07C 29/095* (2013.01); *C07C 29/10* (2013.01); *C07C 29/44* (2013.01); *C07C 29/62* (2013.01); *C07C 41/26* (2013.01); *C07C 51/295* (2013.01); *C07C 67/03* (2013.01); *C07C 67/317* (2013.01); *C07C 67/343* (2013.01); *C07C 69/734* (2013.01); *C07D 319/06* (2013.01); *C07F 5/06* (2013.01); *C12P 7/62* (2013.01); *C07B 2200/05* (2013.01); *C07B 2200/07* (2013.01); *C07C 2101/14* (2013.01)

(58) Field of Classification Search
None
See application file for complete search history.

(56) References Cited

PUBLICATIONS

Xu et al. Chemistry: An Asian Journal (Aug. 2013) 8(8): 1829-1835.*
Organ et al. J. Org. Chem. (2002) 67: 5175-5183 (Year: 2002).*

* cited by examiner

*Primary Examiner* — Susan M Hanley
(74) *Attorney, Agent, or Firm* — Purdue Research Foundation; Yonghao Hou

(57) ABSTRACT

The invention relates to highly enantioselective processes for the synthesis of chiral 1-alkanols via Zr-catalyzed asymmetric carboalumination of alkenes.

20 Claims, 2 Drawing Sheets form
PROCESSES FOR THE SYNTHESIS OF CHIRAL 1-ALKANOLS

CROSS-REFERENCE TO RELATED APPLICATIONS

The present non-provisional patent application is a 35 U.S.C. § 371 national phase application of PCT/US2015/010720, filed Jan. 9, 2015, which is related to and claims the priority of U.S. Provisional Patent Application Ser. No. 61/926,584, filed Jan. 13, 2014, the contents of which is hereby incorporated by reference in its entirety into the present disclosure.

GOVERNMENT INTEREST STATEMENT

This invention was made with government support under GM 036792 awarded by the National Institutes of Health. The government has certain rights in the invention.

TECHNICAL FIELD

The invention relates to highly enantioselective processes for the synthesis of chiral 1-alkanols via Zr-catalyzed asymmetric carboalumination of alkenes.

BACKGROUND OF THE INVENTION

Asymmetric synthesis remains a significant challenge to synthetic organic chemists as the demand for enantiomerically pure compounds continues to increase. Chirality greatly influences a drug's biological and pharmacological properties. Advances in the synthesis of chiral tertiary alkyl-containing compounds have been made through the development of catalytic asymmetric alkene hydrogenation (e.g., Noyori, R. *Asymmetric Catalysis in Organic Synthesis*, 1994, 16-94), epoxidation (e.g., Katsuki, et al. *J. Am. Chem. Soc.* 1980, 102, 5974-5976), and carboalumination (e.g., Kondakov, et al, *J. Am. Chem. Soc.* 1995, 117, 10771-10772). Further, a low enantiomerically pure compound may be purified to the level of ≥98% ee by resorting to sufficiently high selectivity factors (E) (Chen. et al, *J. Am. Chem. Soc.* 1982, 104, 7294-7299) associated with the $R^a$ or $R^b$ group in a desired compound of $R^a R^b CHCH_2OH$. However, in cases where (i) the initial enantiomeric excess of the crude product is low, (ii) the two carbon groups $R^a$ and $R^b$ are structurally similar, and/or (iii) the selectivity factors (E) are sufficiently low, enantiomeric purification of the crudely obtained products, such as $R^a R^b CHCH_2OH$, is difficult and synthetically impractical.

SUMMARY OF THE INVENTION

In one aspect, the present invention features a process of preparing a compound of formula (I)

$$R^2CH_2 - \overset{R^1}{\underset{H}{C}} - (CH_2)_n - OH, \quad (I)$$

wherein $R^1$ is alkyl, cycloalkyl-alkyl, cyclo(hetero)alkyl-alkyl, or aryl-alkyl;

$R^2$ is H, D, $CD_3$, $CH_2CD_3$, $CD_2CH_3$, $CD_2CD_3$, alkyl, cycloalkyl, cycloalkyl-alkyl, cyclo(hetero)alkyl-alkyl, aryl-alkyl, alkenyl, aryl, or heteroaryl, wherein each of alkyl, cycloalkyl, cycloalkyl-alkyl, cyclo(hetero)alkyl-alkyl, aryl-alkyl, alkenyl, aryl, and heteroaryl is optionally mono- or polysubstituted with substituents independently selected from halo, O-alkyl, cyano, amino, nitro, COOMe, and COOEt; and n is 1-8;

the process comprising treating a compound of formula (IV) having a high enantiomeric purity (ee≥99%):

$$XCH_2 - \overset{R^1}{\underset{H}{C}} - (CH_2)_n - OZ, \quad (IV)$$

wherein X is halo or $OR_x$, $R_x$ is a protective group, and Z is H or a protective group; under a reduction condition or a cross-coupling condition to prepare the compound of formula (I), wherein said compound of formula (I) has a high enantiomeric purity (ee≥99%).

In some embodiments, the compound of formula (IV) is prepared by (a) treating a compound of formula (III)

$$\overset{}{\underset{}{\diagup\!\!\!\diagdown}}_n \diagdown OZ \quad (III)$$

under a Zr-catalyzed asymmetric carboalumination condition to prepare intermediate (I);

(b) treating said intermediate (I) with a reagent to prepare said compound of formula (IV) having a low enantiomeric purity (ee<99%); and (c) purifying the compound of formula (IV) having a low enantiomeric purity under a lipase-catalyzed acetylation reaction condition to prepare the compound of formula (IV) having a high enantiomeric purity (ee≥99%).

In another aspect, the invention features a process of preparing a compound of formula (I)

$$R^2CH_2 - \overset{R^1}{\underset{H}{C}} - (CH_2)_n - OH, \quad (I)$$

wherein $R^1$ is alkyl, cycloalkyl-alkyl, cyclo(hetero)alkyl-alkyl, or aryl-alkyl;

$R^2$ is H, D, $CD_3$, $CH_2CD_3$, $CD_2CH_3$, $CD_2CD_3$, alkyl, cycloalkyl, cycloalkyl-alkyl, cyclo(hetero)alkyl-alkyl, aryl-alkyl, alkenyl, aryl, or heteroaryl, wherein each of alkyl, cycloalkyl, cycloalkyl-alkyl, cyclo(hetero)alkyl-alkyl, aryl-alkyl, alkenyl, aryl, and heteroaryl is optionally mono- or polysubstituted with substituents independently selected from halo, O-alkyl, cyano, amino, nitro, COOMe, and COOEt; and n is 1-8;

the process comprising
(a) treating a compound of formula (III)

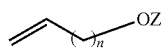

under a Zr-catalyzed asymmetric carboalumination condition to prepare intermediate (I);

(b) treating said intermediate (I) with a reagent to prepare said compound of formula (IV) having a low enantiomeric purity (ee<99%)

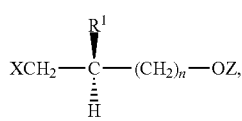

wherein X is halo or $OR_x$, $R_x$ is a protective group, and Z is H or a protective group;

(c) purifying the compound of formula (IV) having a low enantiomeric purity (ee<99%) under a lipase-catalyzed acetylation reaction condition to prepare a compound of formula (IV) having a enantiomeric excess (ee) of 99% or above; and (d) treating said compound of formula (IV) having a high enantiomeric purity (ee≥99%) under a reduction condition or a cross-coupling condition to prepare said compound of formula (I), wherein said compound of formula (I) has a high enantiomeric purity (ee≥99%).

In another aspect, the invention features a process of preparing a compound of formula (II)

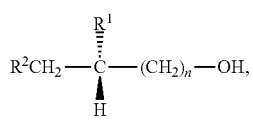

wherein
$R^1$ is alkyl, cycloalkyl-alkyl, cyclo(hetero)alkyl-alkyl, or aryl-alkyl;
$R^2$ is H, D, $CD_3$, $CH_2CD_3$, $CD_2CH_3$, $CD_2CD_3$, alkyl, cycloalkyl, cycloalkyl-alkyl, cyclo(hetero)alkyl-alkyl, aryl-alkyl, alkenyl, aryl, or heteroaryl, wherein each of alkyl, cycloalkyl, cycloalkyl-alkyl, cyclo(hetero)alkyl-alkyl, aryl-alkyl, alkenyl, aryl, and heteroaryl is optionally mono- or polysubstituted with substituents independently selected from halo, O-alkyl, cyano, amino, nitro, COOMe, and COOEt; and
n is 1-8;
the process comprising treating a compound of formula (V) having a high enantiomeric purity (ee≥99%):

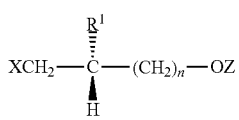

wherein X is halo or $OR_x$, $R_x$ is a protective group, and Z is H or a protective group; under a reduction condition or a cross-coupling condition to prepare said compound of formula (I), wherein said compound of formula (I) has a high enantiomeric purity (ee≥99%).

In some embodiments, the compound of formula (V) is prepared by
(a) treating a compound of formula (III)

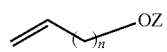

under a Zr-catalyzed asymmetric carboalumination condition to prepare intermediate (II);

(b) treating said intermediate (II) with a reagent to prepare said compound of formula (V) having a low enantiomeric purity (ee<99%); and (c) purifying the compound of formula (V) having a low enantiomeric purity under a lipase-catalyzed acetylation reaction condition to prepare said compound of formula (V) having a high enantiomeric purity (ee≥99%).

In another aspect, the invention features a process of preparing a compound of formula (II)

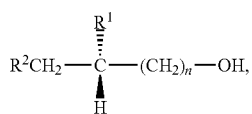

wherein
$R^1$ is alkyl, cycloalkyl-alkyl, cyclo(hetero)alkyl-alkyl, or aryl-alkyl;
$R^2$ is H, D, $CD_3$, $CH_2CD_3$, $CD_2CH_3$, $CD_2CD_3$, alkyl, cycloalkyl, cycloalkyl-alkyl, cyclo(hetero)alkyl-alkyl, aryl-alkyl, alkenyl, aryl, or heteroaryl, wherein each of alkyl, cycloalkyl, cycloalkyl-alkyl, cyclo(hetero)alkyl-alkyl, aryl-alkyl, alkenyl, aryl, and heteroaryl is optionally mono- or polysubstituted with substituents independently selected from halo, O-alkyl, cyano, amino, nitro, COOMe, and COOEt; and
n is 1-8;
the process comprising
(a) treating a compound of formula (III)

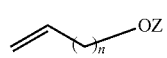

under a Zr-catalyzed asymmetric carboalumination condition to prepare intermediate (II);

(b) treating said intermediate (II) with a reagent to prepare said compound of formula (V) having a low enantiomeric purity (ee<99%)

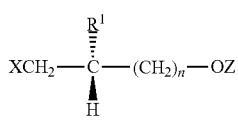

wherein X is halo or $OR_x$, $R_x$ is a protective group, and Z is H or a protective group;

(c) purifying the compound of formula (V) having a low enantiomeric purity under a lipase-catalyzed acetylation reaction condition to prepare a compound of formula (V) having a high enantiomeric purity (ee≥99%); and (d) treating said compound of formula (V) having a high enantiomeric purity (ee≥99%) under a reduction condition or a cross-coupling condition to prepare said compound of formula (II), wherein said compound of formula (II) has a high enantiomeric purity (ee≥99%).

The details of one or more embodiments of the invention are set forth in the accompanying the description below. Other features, objects, and advantages of the invention will be apparent from the description and drawings, and from the claims.

Figure 1:
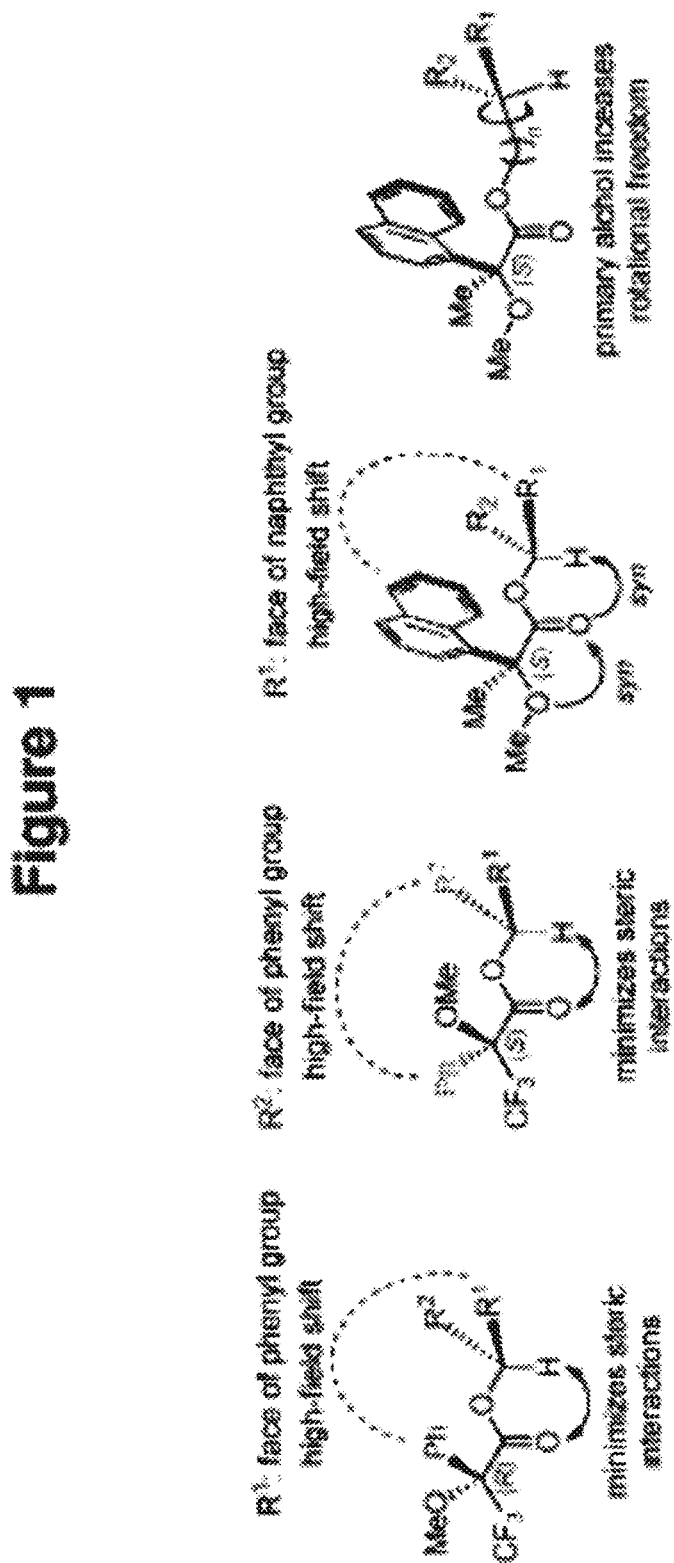
FIG. 1 depicts MTPA and MαNP esters of secondary alcohols as NMR-distinguishable chiral derivatives.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

In one aspect, the invention features a process of preparing a compound of formula (I)

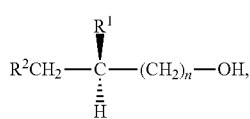

(I)

wherein
$R^1$ is alkyl, cycloalkyl-alkyl, cyclo(hetero)alkyl-alkyl, or aryl-alkyl;
$R^2$ is H, D, CD$_3$, CH$_2$CD$_3$, CD$_2$CH$_3$, CD$_2$CD$_3$, alkyl, cycloalkyl, cycloalkyl-alkyl, cyclo(hetero)alkyl-alkyl, aryl-alkyl, alkenyl, aryl, or heteroaryl, wherein each of alkyl, cycloalkyl, cycloalkyl-alkyl, cyclo(hetero)alkyl-alkyl, aryl-alkyl, alkenyl, aryl, and heteroaryl is optionally mono- or polysubstituted with substituents independently selected from halo, O-alkyl, cyano, amino, nitro, COOMe, and COOEt; and
n is 1-8;

the process comprising treating a compound of formula (IV) having a high enantiomeric purity (ee≥99%):

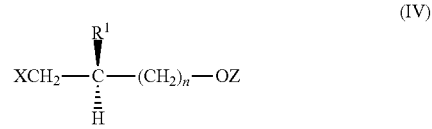

(IV)

wherein X is halo or $OR_x$, $R_x$ is a protective group; and Z is H or a protective group; under a reduction condition or a cross-coupling condition to prepare said compound of formula (I), wherein said compound of formula (I) has a high enantiomeric purity (ee≥99%).

In some embodiments, the compound of formula (IV) is prepared by (a) treating a compound of formula (III)

(III)

under a Zr-catalyzed asymmetric carboalumination condition to prepare intermediate (I);

(b) treating said intermediate (I) with a reagent to prepare said compound of formula (IV) having a low enantiomeric purity (ee<99%); and (c) purifying the compound of formula (IV) having a low enantiomeric purity under a lipase-catalyzed acetylation reaction condition to prepare said compound of formula (IV) having a high enantiomeric purity (ee≥99%)

In some embodiments, the reduction condition comprises LiAlH$_4$. In some embodiments, the reduction condition comprises LiAlD$_4$.

In some embodiments, the cross-coupling condition is a Cu-, Ni-, or Pd-catalyzed cross-coupling reaction.

In some embodiments, the cross-coupling condition is a Cu-catalyzed cross-coupling reaction with an alkylmagnesium halide reagent. In some embodiments, the cross-coupling condition comprises MeMgBr and Li$_2$CuCl$_4$. In some embodiments, the cross-coupling condition comprises CD$_3$MgBr and Li$_2$CuCl$_4$. In other embodiments, the cross-coupling condition comprises EtMgCl, CuCl$_2$, and 1-phenylpropyne. In some embodiments, the cross-coupling condition comprises CD$_3$CH$_2$MgCl, CuCl$_2$, and 1-phenylpropyne. In some embodiments, the cross-coupling condition comprises CD$_3$CD$_2$MgCl, CuCl$_2$, and 1-phenylpropyne. In some embodiments, the cross-coupling condition comprises CH$_3$CD$_2$MgCl, CuCl$_2$, and 1-phenylpropyne.

In some embodiments, the cross-coupling condition is a Pd-catalyzed Negishi coupling reaction condition. In certain embodiments, the Pd-catalyzed Negishi coupling condition comprises vinyl bromide and Pd(DPEphos)Cl$_2$.

In some embodiments, the Zr-catalyzed asymmetric carboalumination condition comprises a trialkylaluminium reagent, an aluminoxane, and (+)-(NMI)$_2$ZrCl$_2$ in a solvent. In some embodiments, the aluminoxane is methylaluminoxane. In some embodiments, the trialkylaluminium is Me$_3$Al. In other embodiments, the aluminoxane is isobutylaluminoxane. In certain embodiments, the trialkylaluminium is Et$_3$Al or $^n$Pr$_3$Al. In some embodiments, the solvent is CH$_2$Cl$_2$.

In some embodiments, the lipase-catalyzed acetylation reaction condition comprises a lipase and vinyl acetate in a solvent. In some embodiments, the lipase is Amano PS lipase or Amano AK lipase. In certain embodiments, the lipase is Amano AK lipase. In some embodiments, the solvent is an organic solvent or a inorganic solvent, or a combination thereof. In certain embodiments, the solvent is $CH_2Cl_2$, $CH_2ClCH_2Cl$, or THF, or $H_2O$. In some embodiments, the solvent is a combination of THF and $H_2O$.

In some embodiments, the reagent in step (b) of the process is an iodinolysis reagent. In other embodiments, the reagent in step (b) of the process is an oxidation reagent. In certain embodiments, the oxidation reagent comprises $O_2$.

In some embodiments, n is 1. In some embodiments, X is iodo. In some embodiments, Z is H. In some embodiments, $R^1$ is alkyl. In certain embodiments, $R^1$ is methyl, ethyl, or n-propyl. In some embodiments, $R^2$ is H, alkyl, or alkenyl.

In some embodiments, n is 2-4. In some embodiments, X is $OR_x$. In certain embodiments, $OR_x$ is OH. In some embodiments, Z is TBS. In some embodiments, $R^1$ is alkyl. In certain embodiments, $R^1$ is methyl, ethyl, or n-propyl. In some embodiments, $R^2$ is H, alkyl, cycloalkyl, cyclo(hetero)alkyl-alkyl, alkenyl, or aryl. In other embodiments, $R^2$ is H, alkyl, cyclohexyl, or p-methylphenyl.

In some embodiments, the process further comprises treating said compound of formula (IV) under a tosylation condition or an iodination condition prior to the cross coupling reaction.

In some embodiments, the compound of formula (I) is selected from
(R)-2-methylpropan-3-$d_1$-1-ol;
(R)-2-ethylbutan-4,4,4-$d_3$-1-ol;
(R)-4-Propylheptan-6,6,7,7,7-$d_5$-1-ol;
(R)-4-propylheptan-6,6-$d_2$-1-ol; and
(R)-4-propylheptan-7,7,7-$d_3$-1-ol.

In some embodiments, the compound of formula (I) is
(R)-2-methylbutan-1-ol;
(R)-2-methylbutan-1-ol;
(R)-2-methylpent-4-en-1-ol;
(R)-2-methylpentan-1-ol;
(R)-2-ethylpentan-1-ol;
(R)-2-ethylpentan-1-ol;
(R)-2-ethylhexan-1-ol;
(R)-2-ethylheptan-1-ol;
(R)-2-propyloctan-1-ol;
(R)-2-propylpent-4-en-1-ol;
(S)-4-ethylheptan-1-ol;
(S)-6-methyl-4-propylheptan-1-ol;
(S)-4-(cyclohexylmethyl)heptan-1-ol; or
(R)-7-(1,3-dioxan-2-yl)-4-propylheptan-1-ol.

In another aspect, the invention features a process of preparing a compound of formula (I)

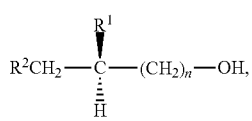

(I)

wherein
$R^1$ is alkyl, cycloalkyl-alkyl, cyclo(hetero)alkyl-alkyl, or aryl-alkyl;
$R^2$ is H, D, $CD_3$, $CH_2CD_3$, $CD_2CH_3$, $CD_2CD_3$, alkyl, cycloalkyl, cycloalkyl-alkyl, cyclo(hetero)alkyl-alkyl, aryl-alkyl, alkenyl, aryl, or heteroaryl, wherein each of alkyl, cycloalkyl, cycloalkyl-alkyl, cyclo(hetero)alkyl-alkyl, aryl-alkyl, alkenyl, aryl, and heteroaryl is optionally mono- or polysubstituted with substituents independently selected from halo, O-alkyl, cyano, amino, nitro, COOMe, and COOEt; and
n is 1-8;
the process comprising
(a) treating a compound of formula (III)

(III)

under a Zr-catalyzed asymmetric carboalumination condition to prepare intermediate (I);

(b) treating said intermediate (I) with a reagent to prepare said compound of formula (IV) having a low enantiomeric purity (ee<99%)

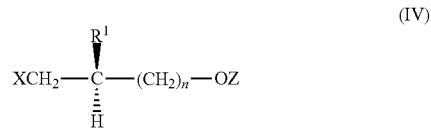

(IV)

wherein X is halo or $OR_x$, $R_x$ is a protective group; and Z is H or a protective group;

(c) purifying the compound of formula (IV) having a low enantiomeric purity under a lipase-catalyzed acetylation reaction condition to prepare a compound of formula (IV) having a enantiomeric excess (ee) of 99% or above; and (d) treating said compound of formula (IV) having a high enantiomeric purity (ee≥99%) under a reduction condition or a cross-coupling condition to prepare said compound of formula (I), wherein said compound of formula (I) has a high enantiomeric purity (ee≥99%).

In another aspect, the invention features a process of preparing a compound of formula (II)

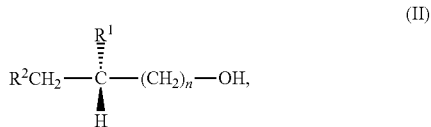

(II)

wherein
$R^1$ is alkyl, cycloalkyl-alkyl, cyclo(hetero)alkyl-alkyl, or aryl-alkyl;
$R^2$ is H, D, $CD_3$, $CH_2CD_3$, $CD_2CH_3$, $CD_2CD_3$, alkyl, cycloalkyl, cycloalkyl-alkyl, cyclo(hetero)alkyl-alkyl, aryl-alkyl, alkenyl, aryl, or heteroaryl, wherein each of alkyl, cycloalkyl, cycloalkyl-alkyl, cyclo(hetero)alkyl-alkyl, aryl-alkyl, alkenyl, aryl, and heteroaryl is optionally mono- or polysubstituted with substituents independently selected from halo, O-alkyl, cyano, amino, nitro, COOMe, and COOEt; and
n is 1-8;
the process comprising treating a compound of formula (V) having a high enantiomeric purity (ee≥99%):

$$XCH_2\underset{H}{\overset{R^1}{-\overset{|}{C}-}}(CH_2)_n-OZ \quad (V)$$

wherein X is halo or $OR_x$, $R_x$ is a protective group; and Z is H or a protective group; under a reduction condition or a cross-coupling condition to prepare said compound of formula (I), wherein said compound of formula (I) has a high enantiomeric purity (ee≥99%).

In some embodiments, the compound of formula (V) is prepared by (a) treating a compound of formula (III)

$$\overset{}{\diagup\!\!\!\diagdown}\!\!\diagdown_n\!\!\diagup^{OZ} \quad (III)$$

under a Zr-catalyzed asymmetric carboalumination condition to prepare intermediate (II)

(b) treating said intermediate (II) with a reagent to prepare said compound of formula (V) having a low enantiomeric purity (ee<99%); and (c) purifying the compound of formula (V) having a low enantiomeric purity under a lipase-catalyzed acetylation reaction condition to prepare said compound of formula (V) having a high enantiomeric purity (ee≥99%)

In some embodiments, the reduction condition comprises $LiAlH_4$. In other embodiments, the reduction condition comprises $LiAlD_4$.

In some embodiments, the cross-coupling condition is a Cu-, Ni-, or Pd-catalyzed cross-coupling reaction.

In some embodiments, the cross-coupling condition is a Cu-catalyzed cross-coupling reaction with an alkylmagnesium halide reagent. In some embodiments, the cross-coupling condition comprises MeMgBr and $Li_2CuCl_4$. In some embodiments, the cross-coupling condition comprises $CD_3MgBr$ and $Li_2CuCl_4$. In other embodiments, the cross-coupling condition comprises EtMgCl, $CuCl_2$, and 1-phenylpropyne. In some embodiments, the cross-coupling condition comprises $CD_3CH_2MgCl$, $CuCl_2$, and 1-phenylpropyne. In some embodiments, the cross-coupling condition comprises $CD_3CD_2MgCl$, $CuCl_2$, and 1-phenylpropyne. In some embodiments, the cross-coupling condition comprises $CH_3CD_2MgCl$, $CuCl_2$, and 1-phenylpropyne.

In some embodiments, the cross-coupling condition is a Pd-catalyzed Negishi coupling reaction condition. In certain embodiments, the Pd-catalyzed Negishi coupling condition comprises vinyl bromide and $Pd(DPEphos)Cl_2$.

In some embodiments, the Zr-catalyzed asymmetric carboalumination condition comprises a trialkylaluminium reagent, an aluminoxane, and $(-)-(NMI)_2ZrCl_2$ in a solvent. In some embodiments, the aluminoxane is methylaluminoxane. In some embodiments, the trialkylaluminium is $Me_3Al$. In other embodiments, the aluminoxane is isobutylaluminoxane. In certain embodiments, the trialkylaluminium is $Et_3Al$ or $^nPr_3Al$. In some embodiments, the solvent is $CH_2Cl_2$.

In some embodiments, the lipase-catalyzed acetylation reaction condition comprises a lipase and vinyl acetate in a solvent. In some embodiments, the lipase is Amano PS lipase or Amano AK lipase. In certain embodiments, the lipase is Amano AK lipase. In some embodiments, the solvent is an organic solvent or a inorganic solvent, or a combination thereof. In certain embodiments, the solvent is $CH_2Cl_2$, $CH_2ClCH_2Cl$, THF, or $H_2O$. In some embodiments, the solvent is a combination of THF and $H_2O$.

In some embodiments, the reagent in step (b) of the process is an iodinolysis reagent. In other embodiments, the reagent in step (b) of the process is an oxidation reagent. In certain embodiments, the oxidation reagent comprises $O_2$.

In some embodiments, n is 1. In some embodiments, X is iodo. In some embodiments, Z is H. In some embodiments, $R^1$ is alkyl. In certain embodiments, $R^1$ is methyl, ethyl, or n-propyl. In some embodiments, $R^2$ is H, alkyl, or alkenyl.

In some embodiments, n is 2-4. In some embodiments, X is $OR_x$. In certain embodiments, $OR_x$ is OH. In some embodiments, Z is TBS. In some embodiments, $R^1$ is alkyl. In certain embodiments, $R^1$ is methyl, ethyl, or n-propyl. In some embodiments, $R^2$ is H, alkyl, cycloalkyl, cyclo(hetero)alkyl-alkyl, alkenyl, or aryl. In other embodiments, $R^2$ is H, alkyl, cyclohexyl, or p-methylphenyl.

In some embodiments, the process further comprises treating said compound of formula (V) under a tosylation condition or an iodination condition prior to the cross coupling reaction.

In some embodiments, said compound of formula (II) is (S)-2-ethylbutan-4,4,4-$d_3$-1-ol; or
(S)-5-propyloctan-7,7,8,8,8-$d_5$-1-ol.

In some embodiments, said compound of formula (II) is selected from
(S)-2-methylbutan-1-ol;
(S)-2-methylpentan-1-ol;
(S)-2-ethylhexan-1-ol;
(S)-2-propylhexan-1-ol;
(S)-2-propyloctan-1-ol;
(R)-3-methylpentan-1-ol;
(S)-3-ethylhexan-1-ol;
(R)-4-methylheptan-1-ol;
(R)-4-ethylheptan-1-ol;
(S)-4-propyloctan-1-ol;
(R)-6-methyl-4-propylheptan-1-ol;
(R)-4-(4-methylbenzyl)heptan-1-ol;
(R,E)-ethyl-8-hydroxy-5-propyloct-2-enoate;
(R)-5-methyloctan-1-ol;
(R)-5-ethyloctan-1-ol;
(R)-5-ethyloctan-1-ol;
(R)-7-eethyl-5-propyloctan-1-ol;
(R)-7,7-eimethyl-5-propyloctan-1-ol;
(R)-5-(cyclohexylmethyl)octan-1-ol; and
(R)-8-(1,3-dioxan-2-yl)-5-propyloctan-1-ol.

In another aspect, the invention features a process of preparing a compound of formula (II)

$$R^2CH_2\underset{H}{\overset{R^1}{-\overset{|}{C}-}}(CH_2)_n-OH, \quad (II)$$

wherein $R^1$ is alkyl, cycloalkyl-alkyl, cyclo(hetero)alkyl-alkyl, or aryl-alkyl;

$R^2$ is H, D, $CD_3$, $CH_2CD_3$, $CD_2CH_3$, $CD_2CD_3$, alkyl, cycloalkyl, cycloalkyl-alkyl, cyclo(hetero)alkyl-alkyl, arylalkyl, alkenyl, aryl, or heteroaryl, wherein each of alkyl, cycloalkyl, cycloalkyl-alkyl, cyclo(hetero)alkyl-alkyl, arylalkyl, alkenyl, aryl, and heteroaryl is optionally mono- or polysubstituted with substituents independently selected from halo, O-alkyl, cyano, amino, nitro, COOMe, and COOEt; and n is 1-8;

the process comprising (a) treating a compound of formula (III)

(III)

under a Zr-catalyzed asymmetric carboalumination condition to prepare intermediate (II);

of various chiral 2-alkyl-1-alkanols, including those that have been otherwise very difficult to prepare, by exploitation of (i) generally facile purification of $ICH_2CH(R^1)CH_2OH$ (1) to the level of ≥99% ee owing to the high E factor associated with iodine proximal to the chiral center and (ii) full retention (>99%) of all carbon skeletal features of (S)-1 or (R)-2 in Pd- or Cu-catalyzed cross-coupling reactions. The desired chiral 2-alkyl-1-alkanols of ≥99% ee, even in cases where $R^1$ and $R^2CH_2$ lacking any proximal π-bonds or heterofunctional groups are structurally similar, have been readily prepared by substituting iodine with various primary, secondary and tertiary carbon groups via Pd- or Cu-catalyzed cross-coupling of (S)-1 or (R)-2 without epimerization (Scheme 1).

The general syntheses of feebly chiral 2-alkyl-1-alkanols are exemplified in Scheme 1.

Scheme 1: Synthesis of Feebly Chiral 2-Alkyl-1-Alkanols

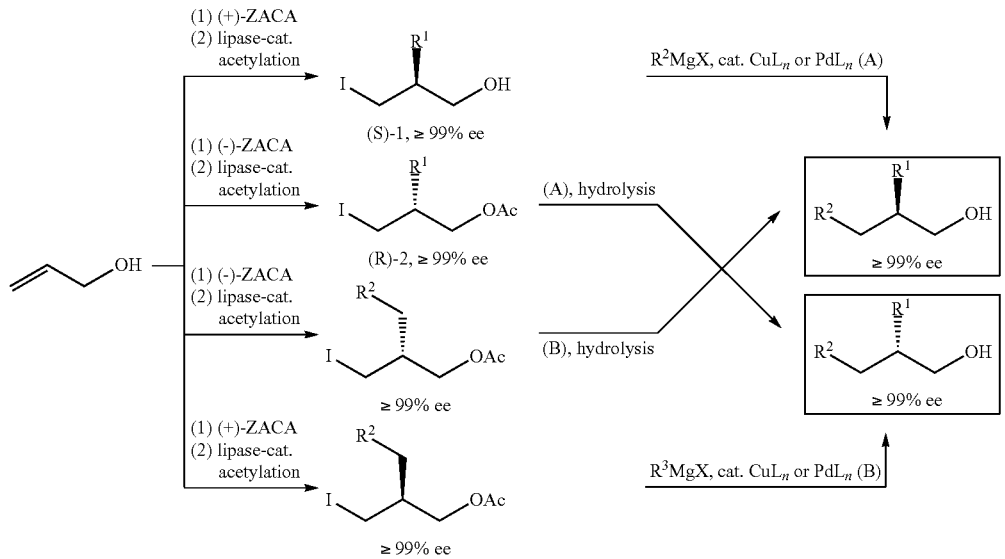

(b) treating said intermediate (II) with a reagent to prepare said compound of formula (V) having a low enantiomeric purity (ee<99%)

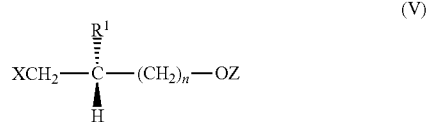

(V)

wherein X is halo or $OR_x$, $R_x$ is a protective group; and Z is H or a protective group;

(c) purifying the compound of formula (V) having a low enantiomeric purity under a lipase-catalyzed acetylation reaction condition to prepare a compound of formula (V) having a enantiomeric excess (ee) of 99% or above; and (d) treating said compound of formula (V) having a high enantiomeric purity (ee≥99%) under a reduction condition or a cross-coupling condition to prepare said compound of formula (II), wherein said compound of formula (I) has a high enantiomeric purity (ee≥99%).

The present invention provides a widely applicable and highly enantioselective (≥99% ee) process for the synthesis The process of the present invention can be used to prepare a compound of formula (I)

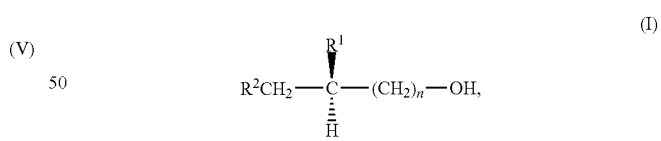

(I)

wherein $R^1$ is alkyl, cycloalkyl-alkyl, cyclo(hetero)alkyl-alkyl, or aryl-alkyl;

$R^2$ is H, D, $CD_3$, $CH_2CD_3$, $CD_2CH_3$, $CD_2CD_3$, alkyl, cycloalkyl, cycloalkyl-alkyl, cyclo(hetero)alkyl-alkyl, aryl-alkyl, alkenyl, aryl, or heteroaryl, wherein each of alkyl, cycloalkyl, cycloalkyl-alkyl, cyclo(hetero)alkyl-alkyl, aryl-alkyl, alkenyl, aryl, and heteroaryl is optionally mono- or polysubstituted with substituents independently selected from halo, O-alkyl, cyano, amino, nitro, COOMe, and COOEt; and n is 1-8.

In some embodiments, $R^1$ is alkyl or cycloalkyl-alkyl. In other embodiments, $R^1$ is aryl-alkyl. In certain embodiments, $R^1$ is alkyl. In other embodiments, $R^1$ is methyl, ethyl, or n-propyl. In some embodiments, $R^1$ is n-butyl or pentyl. In certain embodiments, $R^1$ is methyl or ethyl.

In some embodiments, $R^2$ is H or D. In some embodiments, $R^2$ is $CD_3$, $CH_2CD_3$, $CD_2CH_3$, or $CD_2CD_3$. In other embodiments, $R^2$ is alkyl, for example, methyl, ethyl, propyl, butyl, pentyl, or hexyl. In some embodiments, $R^2$ is cycloalkyl. In certain embodiments, $R^2$ is cyclohexyl. In some embodiments, $R^2$ is cycloalkyl-alkyl, cyclo(hetero) alkyl-alkyl, or aryl-alkyl. In some embodiments, $R^2$ is alkenyl, for example, vinyl. In other embodiments, $R^2$ is aryl or heteroaryl, for example, phenyl or tolyl.

In some embodiments, n is 1. In other embodiments, n is 2-6. In certain embodiments, n is 2-4. In some embodiments, n is 2 or 3.

According to an aspect of the invention, a compound of formulas (IV) and formula (V) can be prepared by (a) treating a compound of formula (III)

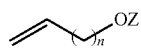
(III)

wherein Z is H or a protective group; under a Zr-catalyzed asymmetric carboalumination condition to prepare an intermediate.

The Zr-catalyzed asymmetric carboalumination condition comprises a trialkylaluminium reagent, an aluminoxane, and $(+)-(NMI)_2ZrCl_2$ or $(-)-(NMI)_2ZrCl_2$ in a solvent. The trialkylaluminium reagent can be any trialkylaluminium known in the art, for example, $Me_3Al$, $Et_3Al$, and $^nPr_3Al$. The aluminoxane can include methylaluminoxane, isobutylaluminoxane, and any aluminoxane known in the art.

Treatment of a compound of formula (III) under a Zr-catalyzed asymmetric carboalumination condition would provide an intermediate, which can be treated with a reagent, for example, an iodinolysis reagent or an oxidizing agent, to provide a compound of formula (IV) or formula (V). When $(+)-(NMI)_2ZrCl_2$ is used in the reaction, a compound of formula (IV) is produced. When $(-)-(NMI)_2ZrCl_2$ is used in the reaction, a compound of formula (V) is obtained. In some embodiments, the obtained compound of formula (IV) or formula (V) after the iodonolysis has an enantiomeric excess of below 90%. In some embodiments, the obtained compound of formula (IV) or formula (V) has an enantiomeric excess of from about 80% to about 88%. For example, the asymmetric synthesis of (R)- and (S)-3-iodo-2-alkyl-1-alkanols (1) was achieved via ZACA reaction of allyl alcohol. Both (S)- and (R)-1a were prepared in 80% and 81% yields by treatment of allyl alcohol with $Me_3Al$ (2.5 equivalents), methylaluminoxane (MAO, 1 equivalent), and $(+)-(NMI)_2ZrCl_2$ or $(-)-(NMI)_2ZrCl_2$ (1-5 mol %) in $CH_2Cl_2$, followed by iodinolysis with $I_2$. Their enantiomeric purities were 82% ee and 84% ee, respectively (Table 1, entries 1 and 2). Similarly, the ZACA reaction of allyl alcohol with $Et_3Al$ or $^nPr_3Al$ was also performed. In these reactions, isobutylaluminoxane (IBAO) was used in place of MAO, and after iodinolysis with $I_2$, (S)-1b, (R)-1b, (S)-1c, and (R)-1c of enantiomeric purities ranging from 80-88% ee were obtained in 59-62% yields (Table 1, entries 3-6).

TABLE 1

Asymmetric synthesis of (R)- and (S)-3-iodo-2-alkyl-1-alkanols (1).

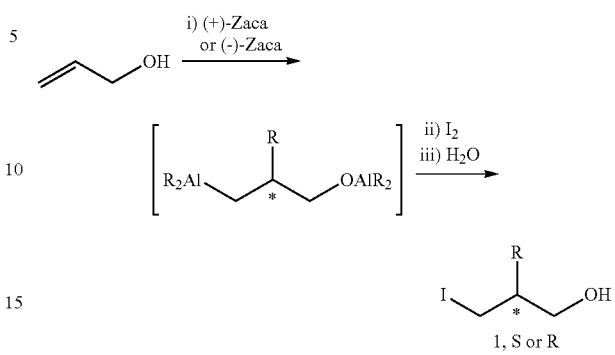

| Entry | R | Protocol[a] | Product | Yield[b] (%) | Purity of 1 (% ee[c]) |
|---|---|---|---|---|---|
| 1 | Me | I | (S)-1a | 80 | 82 |
| 2 | Me | II | (R)-1a | 81 | 84 |
| 3 | Et | III | (S)-1b | 60 | 87 |
| 4 | Et | IV | (R)-1b | 62 | 88 |
| 5 | $^nPr$ | III | (S)-1c | 59 | 82 |
| 6 | $^nPr$ | IV | (R)-1c | 60 | 80 |

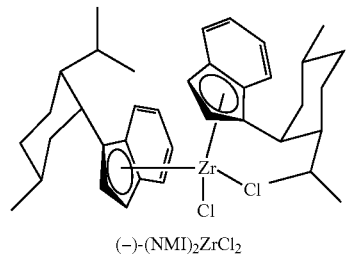

$(-)-(NMI)_2ZrCl_2$

[a]Protocol I: i) $Me_3Al$ (2.5 equiv), MAO (1 equiv), 5 mol % $(+)-(NMI)_2ZrCl_2$; ii) $I_2$ (2.5 equiv), THF. Protocol II: i) $Me_3Al$ (2.5 equiv), MAO (1 equiv), 5 mol % $(+)-(NMI)_2ZrCl_2$; ii) $I_2$ (2.5 equiv), THF. Protocol III: i) $R_3Al$ (3.0 equiv), IBAO (1 equiv), 5 mol % $(+)-(NMI)_2ZrCl_2$; ii) $I_2$ (6 equiv), $Et_2O$. Protocol IV: i) $R_3Al$ (3.0 equiv), IBAO (1 equiv), 5 mol % $(-)-(NMI)_2ZrCl_2$; ii) $I_2$ (6 equiv), $Et_2O$.
[b]Isolated yield.
[c]Enantiomeric excess determined by $^1H$ NMR analysis of Mosher esters.

According to the process of the present invention, the obtained compound of formula (IV) or formula (V) having a low enantiomeric purity, for example, below 90%, can be purified under a lipase-catalyzed acetylation reaction condition to prepare a compound of formula (IV) or formula (V) having a enantiomeric excess (ee) of 99% or above. The lipases purchased from Aldrich, for example, Amano PS lipase from *Pseudomonas cepacia* (Amano PS, purchase dfrom Aldrich) and Amano AK lipase from *Pseudomonas fluorescens* (Amano AK, purchased from Aldrich), are generally satisfactory for the purification of the compound of formula (IV) or formula (V) with a low enantiomeric purity (ee<99%). For example, the (S)-1a of ≥99% ee was prepared in 63% recovery by using Amano PS (Table 2, entry 1). In the purification of (S)-1b, Amano AK and Amano PS were comparatively effective (Table 2, entries 2 and 3). The (S)-1b of ≥99% ee was obtained in 60% recovery yield by using Amano AK (Table 2, entry 4).

Several commercially available lipases were tested for enantiomeric purification of (S)-1c (Table 2, entries 5-10). Amano AK was be the most satisfactory reagent for the purification of (S)-1c, producing (S)-1c of ≥99% ee in 58% recovery yield (Table 2, entry 7). Amano PS lipase was effective in providing (S)-1c of 92% ee in 74% recovery yield (Table 2, entry 8). (S)-1a, (S)-1b, and (S)-1c are now readily obtainable as enantiomerically pure compounds of ≥99% ee in 50%, 36%, and 34% yields over two steps from allyl alcohol in a highly enantioselective, efficient, and satisfactory manner.

TABLE 2

Lipase-catalyzed acetylation of (S)-1.

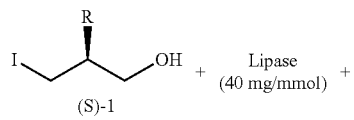

R = Me (1a),
Et (1b), $^n$Pr (1c)

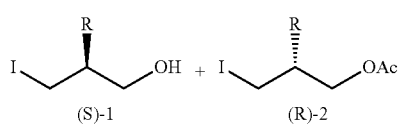

| Entry | Substrate | Initial purity of (S)-1 (% ee) | Lipase | Conversion (%)[a] | Recovery of (S)-1 (%) | Purity of (S)-1 (% ee)[b] |
|---|---|---|---|---|---|---|
| 1 | (S)-1a | 82 | Amano PS | 33 | 63 | >99 |
| 2 | (S)-1b | 87 | Amano PS | 23 | 72 | 96 |
| 3 | (S)-1b | 87 | Amano AK | 22 | 74 | 96 |
| 4 | (S)-1b | 87 | Amano AK | 37 | 60 | >99 |
| 5 | (S)-1c | 82 | PPL | 62 | 35 | 85 |
| 6 | (S)-1c | 82 | Amano AK | 24 | 74 | 94 |
| 7 | (S)-1c | 82 | Amano AK | 39 | 58 | >99 |
| 8 | (S)-1c | 82 | Amano PS | 22 | 74 | 92 |
| 9 | (S)-1c | 82 | Lipase from *Rhizomucor Miehei* | 63 | 34 | 80 |
| 10 | (S)-1c | 82 | Lipase from *Candida rugosa* | 37 | 59 | 83 |

[a]% conversion determined by $^1$H NMR.
[b]Enantiomeric excess determined by $^1$H NMR analysis of Mosher esters.

The results of lipase-catalyzed purification of (R)-1 are summarized in Table 3. (R)-2a of ≥99% ee was prepared in 60% yield by using Amano PS (Table 3, entry 1). (R)-2b of 99% ee was obtained in 52% yield from a 94/6 mixture (88% ee) of (R)-1b and (S)-1b (Table 3, entry 2). Additionally, the (R)-2b of ≥99% ee was also obtained by two rounds of lipase-catalyzed purification in 62% overall yield. Thus, (R)-2b of 96% ee was obtained in 81% yield (Table 3, entry 4). Hydrolysis of acetate (R)-2b (96% ee) without isolation, followed by the second round of lipase-catalyzed acetylation provided the (R)-2b of ≥99% ee (Table 3, entry 5).

Similarly, the acetate of (R)-1c of ≥99% ee was obtained in 50% yield from a 90/10 mixture (80% ee) of (R)-1c and (S)-1c (Table 3, entry 6). (R)-2c of ≥99% ee was also obtained by two rounds of lipase-catalyzed purification in 60% overall yield (Table 3, entries 8 and 9). As summarized in Table 3, (R)-2a, (R)-2b, and (R)-2c were all readily purified to 99% ee in 49%, 38%, and 36% overall yields from allyl alcohol.

TABLE 3

Lipase-catalyzed acetylation of (R)-1.

R = Me (1a), Et (1b), $^n$Pr (1c)

| Entry | Substrate | Initial purity of (R)-1 (% ee) | Lipase | Conversion (%)[b] | Yield of (R)-2 (%) | Purity of (R)-2 (% ee)[e] |
|---|---|---|---|---|---|---|
| 1 | (R)-1a | 84 | Amano PS | 62 | 60 | >99 |
| 2 | (R)-1b | 88 | Amano PS | 56 | 52 | >99 |
| 3 | (R)-1b | 88 | Amano PS | 67 | 64 | 98 |
| 4 | (R)-1b | 88 | Amano PS | 84 | 81 | 96 |
| 5 | (R)-1b | 96 | Amano PS | 82 | 62[c] | >99 |
| 6 | (R)-1c | 80 | Amano AK[a] | 53 | 50 | >99 |
| 7 | (R)-1c | 80 | Amano AK[a] | 63 | 60 | 98 |
| 8 | (R)-1c | 80 | Amano AK[a] | 82 | 79 | 94 |
| 9 | (R)-1c | 94 | Amano AK[a] | 83 | 60[d] | >99 |

[a]Toluene was used in place of THF.
[b]% conversion determined by $^1$H NMR.
[c]Overall yield in two rounds of lipase-catalyzed purification (entry 4 + 5).
[d]Overall yield in two rounds of lipase-catalyzed purification (entry 8 + 9).
[e]Enantiomeric excess determined by $^1$H NMR analysis of Mosher esters.

According to another aspect of the present invention, a compound of formula (IV) or formula (V) can be treated under a reduction condition or a cross-coupling condition to prepare a compound of formula (I), wherein said compound of formula (I) has a high enantiomeric purity (ee≥99%).

The reduction reaction can be carried out by numerous reducing agents known in the art to convert a halo group, such as an iodo group, to a hydrogen atom. In some embodiments, the reduction condition is a catalytic hydrogenation. In other embodiments, the reduction condition comprises LiAlH.

The cross-coupling condition can be a Cu-, Ni-, or Pd-catalyzed cross-coupling reaction. A Cu-catalyzed cross-coupling condition includes a Grignard reagent, such as alkyl- or aryl-magnesium halides. For example, the Grignard reagent can be an alkylmagnesium halide reagent, for example, MeMgBr, CD$_3$MgBr, EtMgCl, CD$_3$CH$_2$MgCl, CD$_3$CD$_2$MgCl, CH$_3$CD$_2$MgCl, or other suitable Grignard reagents for the cross coupling reaction. The catalyst for the Cu-catalyzed cross-coupling condition can be CuCl$_2$ or Li$_2$CuCl$_4$, or others known in the art.

The cross-coupling condition can be a Pd-catalyzed condition. For example, a Pd-catalyzed Negishi coupling reaction condition. In some embodiments, the condition comprises vinyl bromide and Pd(DPEphos)Cl$_2$.

As exemplified in Schemes 2 and 3, a compound of formula (I) or formula (II) can be prepared by cross-coupling reaction of a compound of formula (IV) or formula (V) with a high enantiomeric excess. For example, (S)- and (R)-chiral tertiary alkyl-containing alcohols of high enantiomeric purity were achieved by the Pd- or Cu-catalyzed cross-coupling reactions of several intermediates, e.g., (S)-1a, (S)-1b, (S)-1c, (R)-2a, (R)-2b, and (R)-2c of ≥99% ee.

The cross-coupling reaction of (S)-1a with methylmagnesium bromide (3 equivalents) in the presence of 1 mol % of Li$_2$Cua$_4$ gave (R)-2-methyl-1-butanol (3) of ≥99% ee in 77% yield. Thus, a highly selective and efficient route to the synthesis of (R)-2-methyl-1-butanol (3) (≥99% ee) in 39% yield has been developed from allyl alcohol over three steps via ZACA-lipase-catalyzed acetylation-Cu-catalyzed cross-coupling.

Treatment of (S)-1a with TBSCl followed by Negishi coupling catalyzed by 5 mol % of Pd(DPEphos)Cl$_2$ with vinyl bromide, and subsequent desilylation with tetrabutylammonium fluoride (TBAF), provided (R)-4 in 85% yield over three steps.

Synthesis of (S)-5 was achieved in 70% yield by Cu-catalyzed cross-coupling of (R)-2a with ethylmagnesium chloride (2 equivalents) in the presence of 5 mol % of CuCl$_2$ and 15 mol % of 1-phenylpropyne followed by hydrolysis of the acetate with KOH. All of these three chiral alkanols were obtained with high enantiomeric purity of ≥99% ee.

Scheme 2: Synthesis of chiral tertiary alkyl-containing 1-alcohols from (S)-1a and (R)-2a.

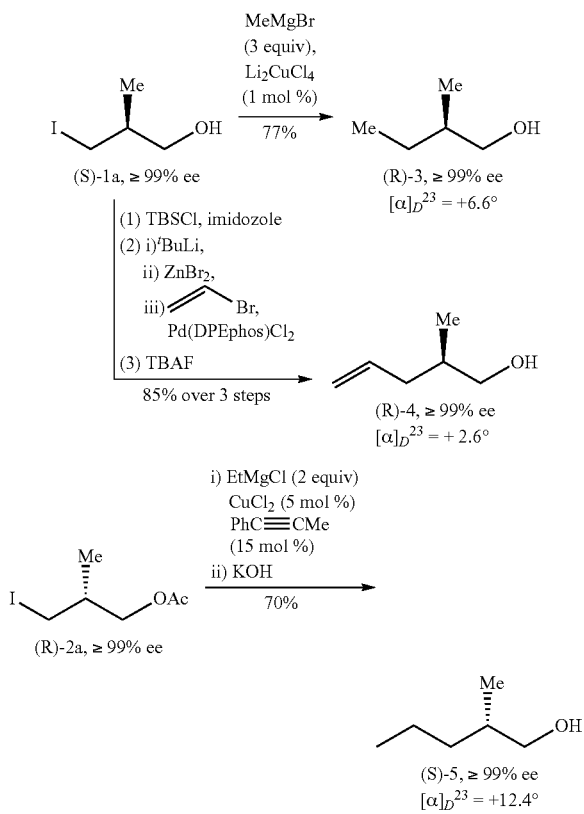

Scheme 3: Synthesis of chiral tertiary alkyl-containing 1-alcohols from (S)-1b and (R)-2b.

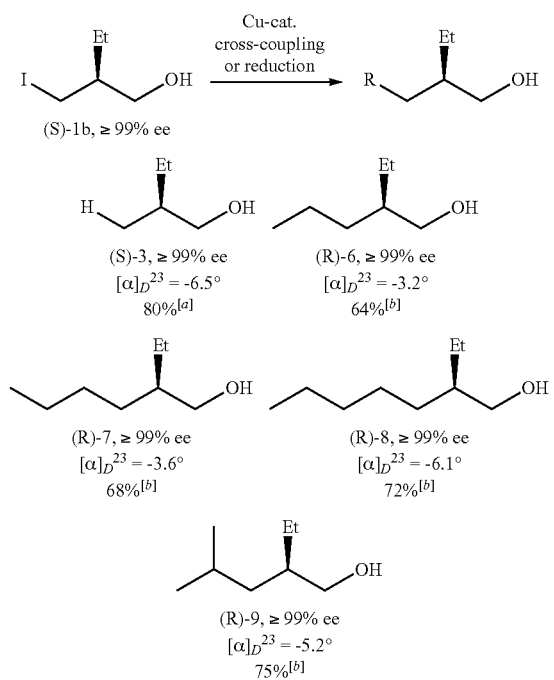

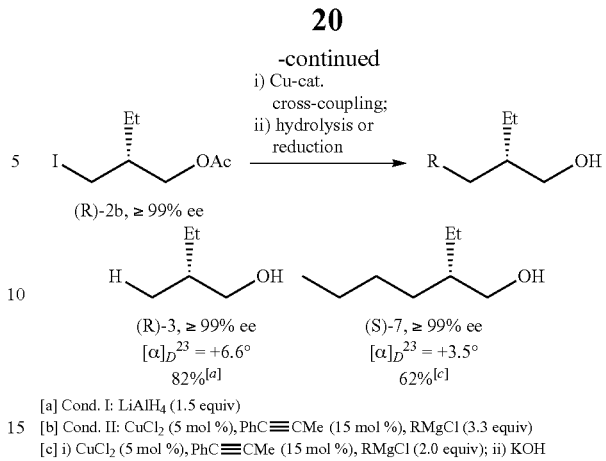

[a] Cond. I: LiAlH$_4$ (1.5 equiv)
[b] Cond. II: CuCl$_2$ (5 mol %), PhC≡CMe (15 mol %), RMgCl (3.3 equiv)
[c] i) CuCl$_2$ (5 mol %), PhC≡CMe (15 mol %), RMgCl (2.0 equiv); ii) KOH (S)-1b of ≥99% ee was converted to (S)-3, (R)-6, (R)-7, (R)-8, and (R)-9 of ≥99% ee by either reduction with LiAlH$_4$ or a Cu-catalyzed cross-coupling in 64-80% yields as shown in Scheme 3. (R)-2-Methyl-1-butanol (3) of ≥99% ee was also obtained by reduction of (R)-2b with LiAlH$_4$ (1.5 equivalents) in 82% yield. (S)-7 of ≥99% ee was prepared from (R)-2b in 62% yield via Cu-catalyzed cross-coupling and subsequent hydrolysis.

The preparation of (S)-6 and (R)-10 were achieved by cross-coupling reactions of (S)-1c with methylmagnesium chloride (3.3 equivalents) and n-propylmagnesium chloride (3.3 equivalents) in the presence of 5 mol % of CuCl$_2$ and 15 mol % of 1-phenylpropyne in 80% and 70% yields as shown in Scheme 4. Secondary and tertiary Grignard reagents can also be used under similar reaction conditions providing (R)-12 and (R)-13 in 70% and 68% yields, respectively. Acetylation of (S)-1c with Ac$_2$O, followed by treatment with 3 mol % of Li$_2$Cua$_4$, N-methylpyrrolidone (NMP, 4 equivalents) and n-pentylmagnesium bromide (2 equivalents), and subsequent hydrolysis with KOH, provided (R)-11 of ≥99% ee in 76% yield over three steps. (S)-11 of ≥99% ee was also obtained in 80% yield over two steps from (R)-2c. The preparation of (R)-14 of ≥99% ee was carried out by TBS-protection of (S)-1c, Pd(DPEphos)Cl$_2$-catalyzed Negishi coupling, and TBAF desilylation in 82% yield over three steps. Reduction of (R)-2c with LiAlH$_4$ (1.5 equivalents) gave (R)-5 in 86% yield. The preparation of (R)-6, (S)-10, and (S)-13 were performed by similar Cu-catalyzed cross-coupling and subsequent hydrolysis from (R)-2c in 69%, 64%, and 70% yields, respectively.

The enantiomeric purity of alcohols 3, 4, and 5 can be readily determined by $^1$H NMR analysis of their corresponding Mosher Esters. In the cases where the two alkyl branches at the chiral carbon are closely similar to each other, as in the cases of 6, 7, 9, 10, 11, and 13, the chemical shifts of the diastereomeric Mosher esters were not sufficiently separated to allow quantitative determination of the enantiomeric purity by $^1$H NMR. The enantiomeric purities of these compounds were therefore determined by chiral GC.

Scheme 4: Synthesis of chiral tertiary alkyl-containing 1-alcohols from (S)-1c and (R)-2c

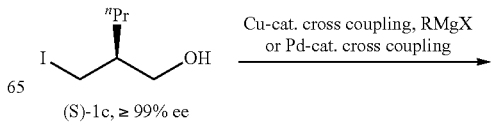

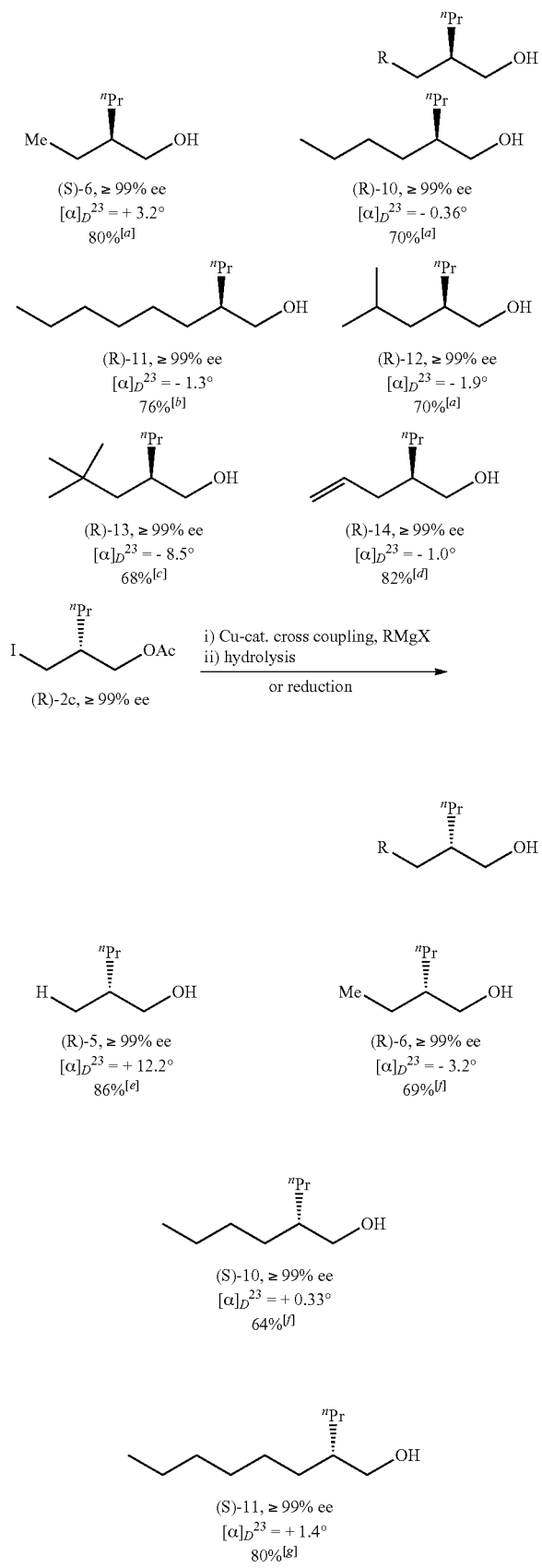

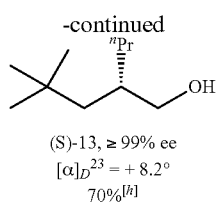

(S)-13, ≥ 99% ee
$[\alpha]_D^{23} = +8.2°$
70%[h]

[a] Cond. I: CuCl₂ (5 mol %), PhC≡CMe (15 mol %), RMgCl (3.3 equiv)
[b] (1) Ac₂O; (2) Li₂CuCl₄ (3 mol %), NMP (4 equiv), ⁿPentMgBr (2 equiv); (3) KOH/MeOH
[c] (1) Ac₂O; (2) CuCl₂ (5 mol %), PhC≡CMe (15 mol %), RMgCl (3 equv); (3) KOH/MeOH
[d] (1) TBSCl; (2) i) ᵗBuLi; ii) ZnBr₂; iii) ⌇Br, Pd(DPEphos)Cl₂; (3) TBAF
[e] LiAlH₄ (1.5 equiv)
[f] i) Li₂CuCl₄ (5 mol %), RMgCl (3 equiv); ii) KOH/MeOH
[g] i) Li₂CuCl₄ (3 mol %), NMP (4 equiv), ⁿPentMgBr ( 2 equiv); ii) KOH/MeOH
[h] i) CuCl₂ (5 mol %), PhC≡CMe (15 mol %), RMgCl (3 equiv); ii) KOH/MeOH The present invention provides a highly enantioselective and widely applicable route to various chiral 2-alkyl-1-alkanols, especially those of feeble chirality (defined as optical rotation <10°), by ZACA-Pd- or Cu-catalyzed cross-coupling. Either enantiomer of such alcohols can be obtained in high enantioselectivity from the (R)- or (S)-enantiomer of (1). With advances in Pd-, Ni-, or Cu-catalyzed cross-coupling of alkyl halide with a wide variety of alkyl (primary, secondary, and tertiary), cyclic alkyl, vinyl, and aryl Grignard reagents, organozincs, or organoboron compounds, the present invention would provide a widely applicable, convenient, and efficient procedure for the synthesis of a very broad range of enantiomerically pure (≥99% ee) chiral tertiary alkyl-containing alcohols.

It will be appreciated in the art that chiral 2-alkyl-1-alkanols can be readily transformed into their corresponding optically active aldehydes, carboxylic acids, and other classes of compounds. For example, the present invention can be used to prepare both (R)- and (S)-arundic acids. As shown in Scheme 5, (R)- and (S)-11 of ≥99% ee, prepared by ZACA-lipase-catalyzed purification-Cu-catalyzed cross-coupling tandem reactions (Scheme 4), were transformed into the corresponding (R)- and (S)-arundic acids in 98% yield by oxidation with NaClO₂ in the presence of catalytic amounts of NaClO and 2,2,6,6-tetramethylpiperidin-1-yloxyl (TEMPO). A highly enantioselective and efficient synthesis of (R)- and (S)-arundic acids was achieved in 25% and 28% over five steps, respectively, from allyl alcohol.

Scheme 5: Synthesis of (R)- and (S)-arundic acids.

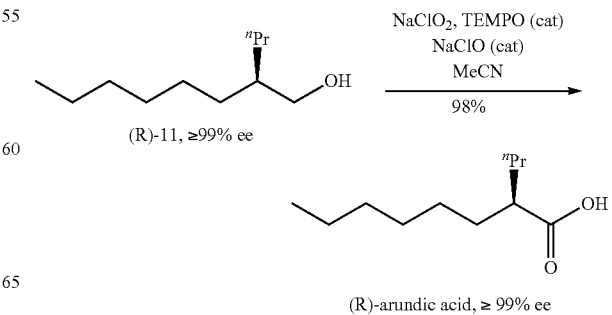

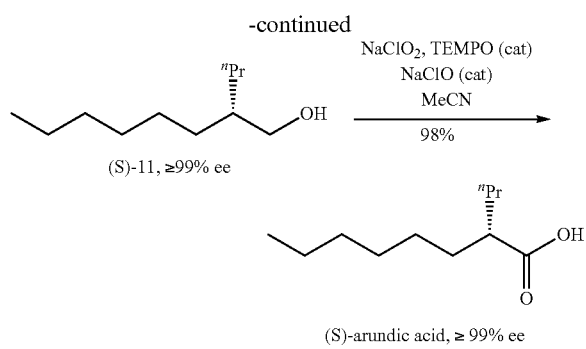

For the synthesis of γ- and more-remotely chiral alcohols of high enantiomeric purity, the alkylalane intermediates prepared by ZACA reaction of TBS-protected ω-alkene-1-ols are to be subjected to in situ oxidation with $O_2$ to introduce OH group of α,ω-dioxyfunctional chiral intermediates (15) (Scheme 6). The strategies shown in the specification illustrate the versatility of ZACA representing by the organoaluminum functionality of the initially formed ZACA products.

The introduction of the OH group by oxidation of initially formed alkylalane intermediates in Scheme 6 is based on two considerations: (i) the close proximity of the OH group to stereogenic carbon center is required for lipase-catalyzed acetylation to provide the ultrapure (≥99% ee) difunctional intermediates, and (ii) the versatile OH group can be further transformed to a wide range of carbon groups by tosylation or iodination and Cu- or Pd-catalyzed cross-coupling. The OTBS group serves a source of OH group in the final desired alkanols, and as a proximal heterofunctional group leading to higher enantioselectivity in lipase-catalyzed acetylation. As long as the α,ω-dioxyfunctional chiral intermediates (R)-15 and (S)-16 can be readily prepared as enantiomerically pure (≥99% ee) substances, their subsequent Cu- or Pd-catalyzed cross-coupling with retention of all carbon skeletal features would produce a wide range of enantiomerically ally pure γ- and more-remotely chiral alcohols in high enantiomeric purity.

The features of the ZACA reaction include (i) catalytic asymmetric C—C bond forming reaction, (ii) one-point-binding without requiring any other functional groups, and (iii) many potential transformations of initially formed alkylalane intermediates. The preparation of α,ω-dioxyfunctional key intermediates (15) by ZACA reaction of different TBS-protected ω-alkene-1-ols is summarized in Table 4. Commercially available 3-buten-1-ol, 4-penten-1-ol, and 5-hexen-1-ol were protected with TBSCl and imidazole and subjected to the ZACA reaction using $Et_3Al$ or $^nPr_3Al$ (2 equiv), isobutylaluminoxane (IBAO, 1 equiv) (14,15), and a catalytic amount of (−)-bis-(neomenthylindenyl)zirconium dichloride [(−)-$(NMI)_2ZrCl_2$] or (+)-bis-(neomenthylindenyl)zirconium dichloride [(+)-$(NMI)_2ZrCl_2$] (16,17), and followed by in situ oxidation with $O_2$. The crude alcohols (15) were obtained in 68-78% yields, and the enantiomeric purities ranged from 80-86% ee.

TABLE 4

ZACA reaction of TBS-protected ω-alkene-1-ols.

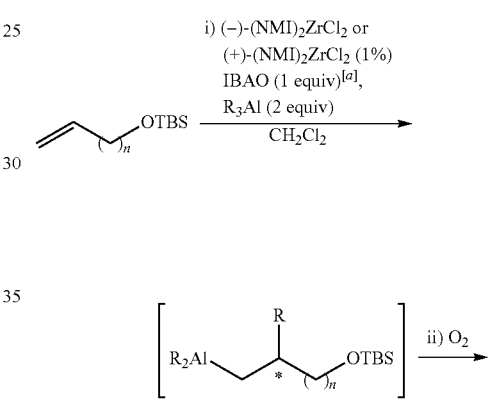

Scheme 6. Synthesis of γ- and more-remotely chiral 1-alkanols

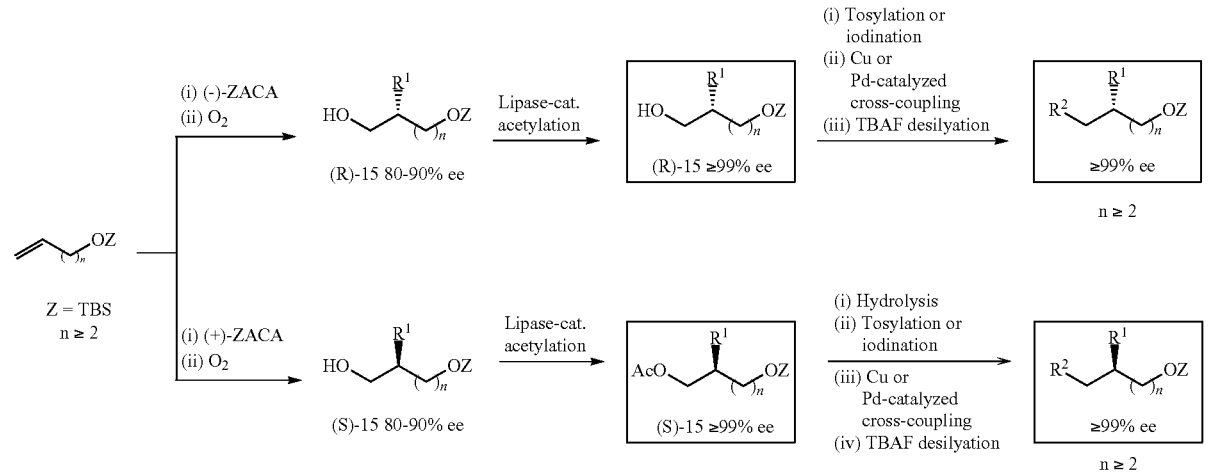

a) ZACA: Zirconium-catalyzed Asymmetric Carboalumination of Alkenes
b) $R^1$ = alkyl group, $R^2$ = alkyl, alkenyl, alkynyl, or aryl group

TABLE 4-continued

HO~*~OTBS (chain with R substituent)
15, R or S

| Entry | n | (NMI)$_2$ZrCl$_2$ | R | Product | Yield (%) | Purity of 15 (% ee)[b] |
|---|---|---|---|---|---|---|
| 1 | 2 | (−) | Et | (R)-15a | 78 | 86 |
| 2 | 3 | (−) | $^n$Pr | (R)-15b | 72 | 82 |
| 3 | 3 | (+) | $^n$Pr | (R)-15b | 69 | 85 |
| 4 | 4 | (−) | $^n$Pr | (R)-15c | 68[c] | 80 |

[a]IBAO (isobutylaluminoxane): prepared by mixing equimolar quantities of $^i$Bu$_3$Al and H$_2$O.
[b]Enantiomeric excess determined by chiral GC or $^1$H NMR analysis of Mosher esters
[c]3 mol % (−)-(NMI)$_2$ZrCl$_2$ was used.

Enantiomeric purification of α,ω-dioxyfunctional intermediates (15) of 80-86% ee obtained by the ZACA reaction was carried out, and the results are summarized in Table 5. Amano PS lipase from *Pseudomonas cepacia* (Aldrich) was generally superior to Amano AK lipase from *Pseudomonas fluorescens* (Aldrich) in the purification of (R)-15a and 15b (Table 5, entries 1-2 and 5-6). 1,2-dichlroethane proved to be a more suitable solvent than THF in the purification of (R)-15a and 15b (Table 5, entries 2-3 and 6-7). (R)-15a, 15b and 15c were readily purified to the level of ≥99% ee by Amano PS lipase-catalyzed acetylation with vinyl acetate in 60-73% recovery yields. Further, Amano PS lipase-catalyzed acetylation of (S)-15b of 85% ee provided acetate (S)-16b which was hydrolyzed with KOH to form (S)-15b of 97.6% ee in 82% recovery. (S)-15b of 97.6% ee was further subjected to a second round of lipase-catalyzed acetylation/hydrolysis to give (S)-15b of ≥99% ee in 85% recovery (Table 5, entries 10). These results clearly indicate that the present invention provides a very favorable route to a wide range of both (R) and (S)-α,ω-dioxyfunctional alcohols in high enantiomeric purity, which would be able to serve as potentially versatile difunctional chiral synthons.

TABLE 5

Enantiomerical purification of (15) by lipase-catalyzed acetylation.

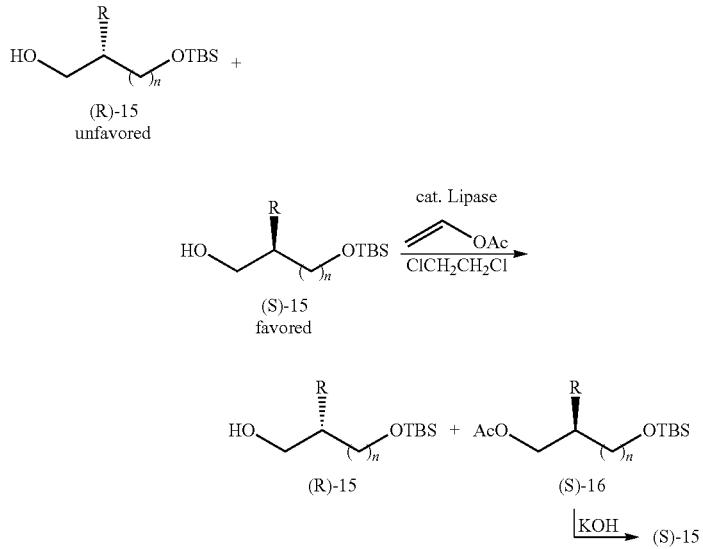

| Entry | Substrate | Initial purity of 3 (% ee$_0$) | Lipase[b] | Conversion (%) | Recovery of 3 (%) | Purity of 3 (% ee)[c] |
|---|---|---|---|---|---|---|
| 1 | (R)-15a[a] | 86 | Amano AK | 30 | 67 | 95 |
| 2 | (R)-15a[a] | 86 | Amano PS | 22 | 77 | 98 |
| 3 | (R)-15a | 86 | Amano PS | 18 | 80 | 98 |
| 4 | (R)-15a | 86 | Amano PS | 25 | 73 | ≥99 |
| 5 | (R)-15b[a] | 82 | Amano AK | 36 | 62 | 93 |
| 6 | (R)-15b[a] | 82 | Amano PS | 33 | 65 | ≥99 |
| 7 | (R)-15b | 82 | Amano PS | 28 | 69 | ≥99 |
| 8 | (R)-15c | 80 | Amano PS | 39 | 60 | ≥99 |
| 9 | (R)-15b[d] | 85 | Amano PS | 85 | 82 | 97.6 |
| 10 | (R)-15b[d] | 97.6 | Amano PS | 88 | 85 | ≥99 |

[a]THF was used instead of 1,2-dichloroethane
[b]Lipase-catalyzed acetylation is S-selective. The acetylation rate of (S)-15 is faster than that of (R)-15
[c]Enantiomeric excess determined by chiral GC or $^1$H NMR analysis of Mosher esters.
[d]Lipase-catalyzed acetylation was followed by hydrolysis of (S)-16b to give (S)-15b.

The present invention can be used to synthesize a wide range of γ- and more-remotely chiral alcohols of high enantiomeric purity, most of which have never been synthesized before, via key intermediates (15) by Cu- or Pd-catalyzed cross-coupling reactions. (R)-15a of ≥99% ee was converted to tosylate (R)-17. (R)-18 and (S)-19 of ≥99% ee were then synthesized by further transformation of (R)-17 via reduction with LiAlH$_4$ (1.5 equivalents) or CuCl$_2$-catalyzed cross-coupling with ethylmagnesium chloride (2 equivalents) and 15 mol % of 1-phenylpropyne (13), followed by removal of the TBS group with TBAF, in 75% and 80% yields over three steps, respectively (Scheme 7).

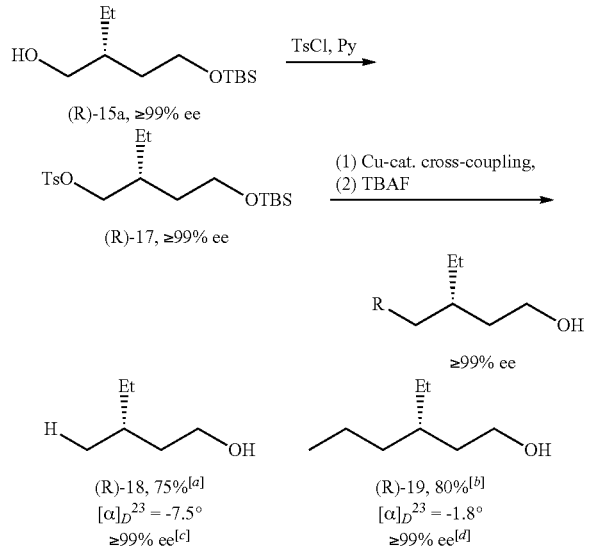

[a] (1) LiAlH$_4$ (1.5 equiv); (2) TBAF
[b] (1) CuCl$_2$ (5 mol %), PhC≡CMe (15 mol %), EtMgCl (2 equiv); (2) TBAF
[c] Enantiomeric excess determined by $^1$H NMR analysis of Mosher esters
[d] Enantiomeric excess determined by chiral GC For the synthesis of chiral 4-alkyl-1-alknols of ≥99% ee, (R)-15b was first transformed to the corresponding tosylate (R)-20a or iodide (R)-20b. The preparation of (R)-21 was performed by the reduction of tosylate (R)-20a with LiAlH$_4$ followed by TBAF desilylation in 80% yield over three steps. Tosylate (R)-20a was also subjected to the Cu-catalyzed cross-coupling reactions with different alkylmagnesium halide reagents to provide (R)-22, (S)-23, and (R)-24 in 77-84% yields. Aryl and alkenyl groups can also be introduced by Pd-catalyzed to Negishi coupling. The preparation of (R)-25 and (R)-26 of ≥99% ee was carried out by zincation of iodide (R)-20b, Pd-catalyzed Negishi coupling with substituted aryl or alkenyl halides, and TBAF desilylation in 60% and 58% yields over three steps, respectively (Scheme 8).

Scheme 8. Synthesis of chiral 4-alkyl-1-alcohols from (R)-15b

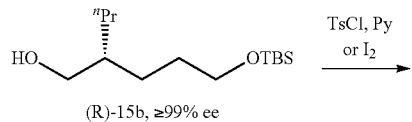

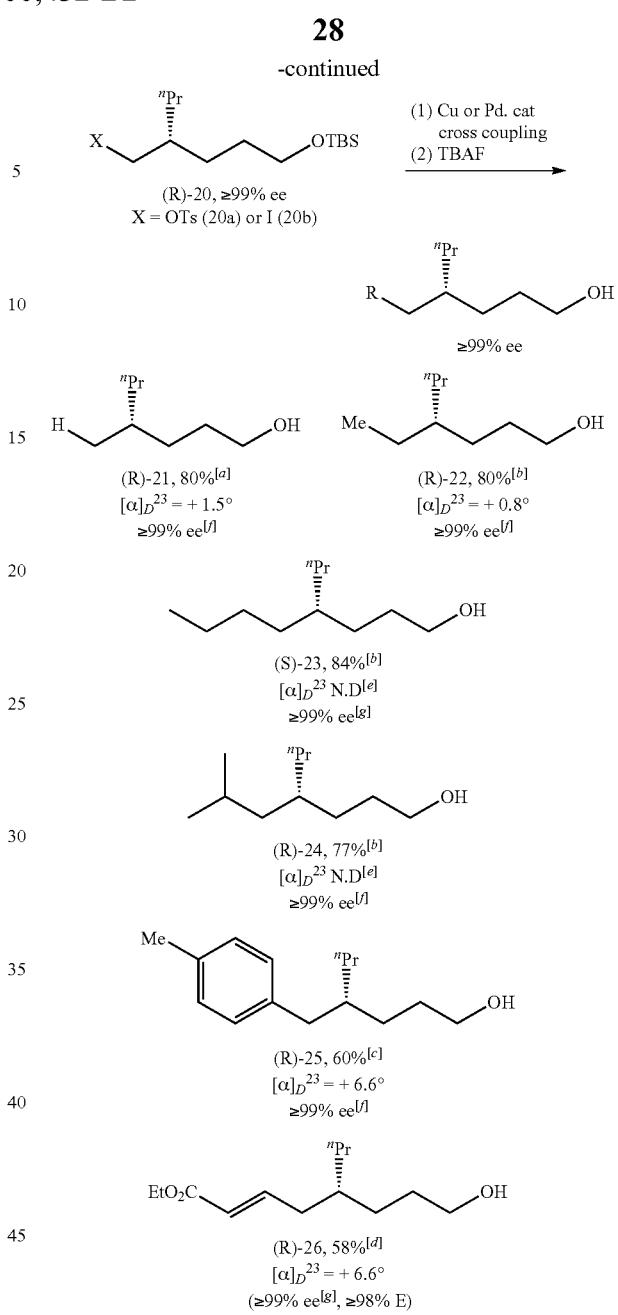

[a] (1) LiAlH$_4$ (1.5 equiv); (2) TBAF
[b] (1) CuCl$_2$ (5 mol%), PhC≡CMe (15 mol%), RMgCl (2 equiv); 2) TBAF
[c] (1) $^t$BuLi, ii) ZnBr$_2$, iii) Pd($^t$Bu$_3$P)$_2$ (5 mol%), RI; (2) TBAF
[d] (1) $^t$BuLi, ii) ZnBr$_2$, iii) PEPPSI-IPr (5 mol%), RBr, (2) TBAF
[e] [α]$_D^{23}$ is too small to be determined
[f] Enantiomeric excess determined by chiral GC
[g] Enantiomeric excess determined by $^1$H NMR analysis of 2-methoxy-2-(1-naphthyl)propionic acid esters (S)-15b was also employed as a key intermediate in the synthesis of chiral 4-alkyl-1-alcohols (S)-22, (S)-24, and (S)-27 by tosylation, CuCl$_2$/1-phenylpropyne-catalyzed cross-coupling with alkylmagnesium halide reagents and TBAF desilylation in 70-73% yields over three steps, respectively. (R)-28 was synthesized by the cross-coupling reaction of iodide (S)-20b in the presence of N-methylpyrrolidone (NMP, 4 equivalents) as an enantiomerically pure compound of ≥99% ee in 67% yield over three steps (Scheme 9).

Scheme 9. Synthesis of chiral 4-alkyl-1-alcohols from (S)-15b

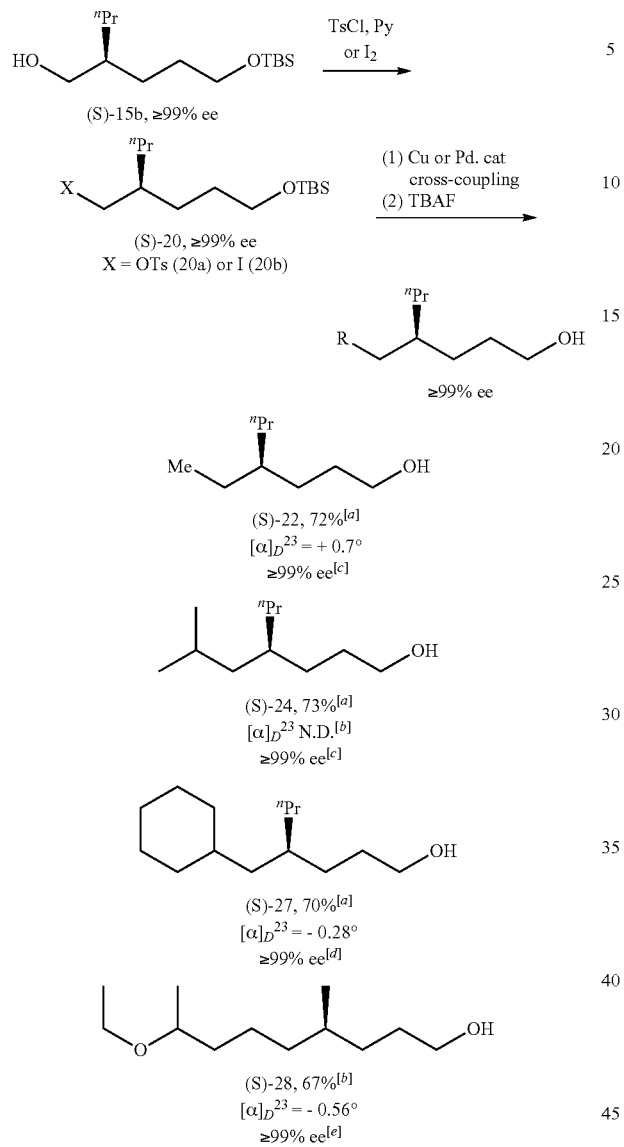

Scheme 10. Synthesis of chiral 4-alkyl-1-alcohols from (R)-15c.

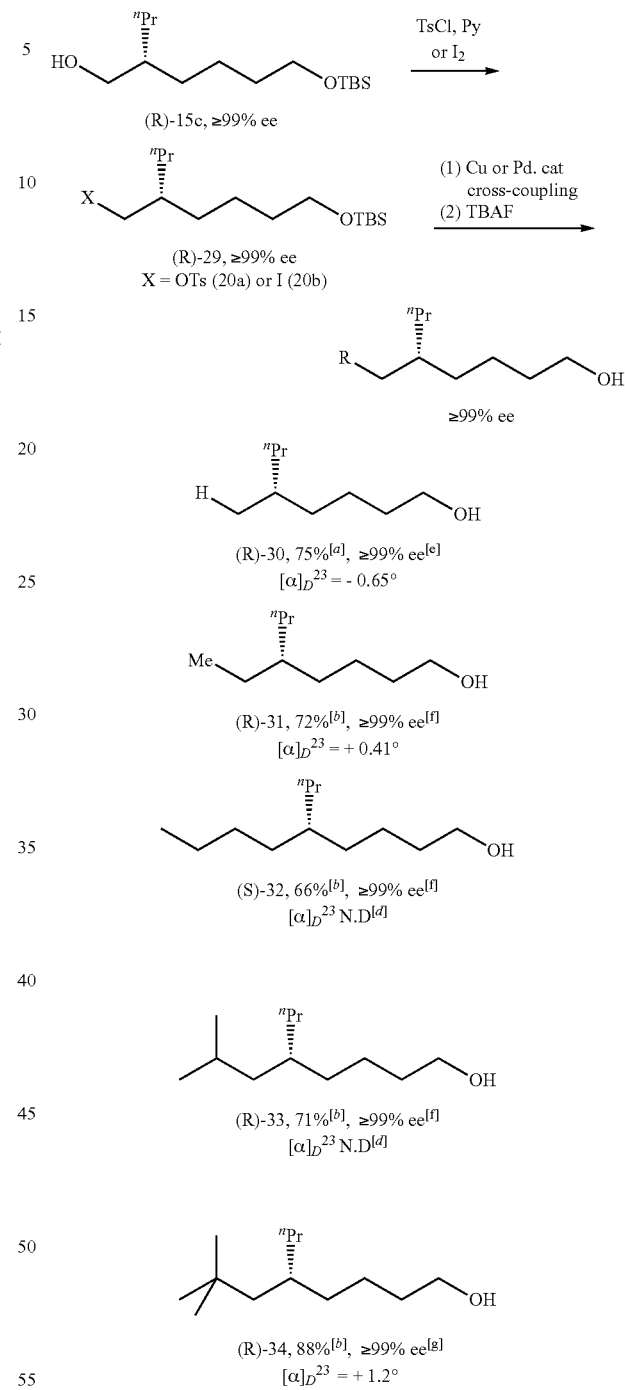

[a] (1) CuCl$_2$ (5 mol%), PhC≡CMe (15 mol%), RMgX (2 equiv): 2) TBAF
[b] (1) CuCl$_2$ (5 mol%), PhC≡CMe (15 mol%), NMP (4 equiv), RMgX (2 equiv); 2) TBAF
[c] Enantiomeric excess determined by chiral GC
[d] Enantiomeric excess determined by $^1$H NMR analysis of Mosher esters
[e] Enantiomeric excess determined by $^1$H NMR analysis of 2-methoxy-2-(1-naphthyl)propionic acid esters A similar synthetic strategy was employed in the synthesis of chiral 5-alkyl-1-alknols of ≥99% ee from the intermediate (R)-15c. Reduction of tosylate (R)-29a with LiAlH$_4$ followed by TBAF desilylation provided (R)-30 in 75% yield. Cu-catalyzed cross-coupling reactions of tosylate (R)-29a or iodide (R)-29b with different alkyl (primary, secondary, tertiary, cyclic) Grignard reagents, even with functional groups, proceeded smoothly to form a wide range of enantiomerically pure (≥99% ee) chiral 5-alkyl-1-alknols 31-36 after deprotection of TBS group (Scheme 10).

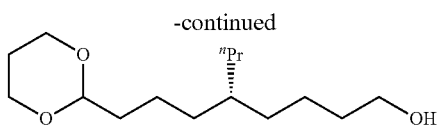

(R)-36, 61%[b], ≥99% ee[f]
[α]$_D^{23}$ = +0.63°

[a] (1) LiAlH$_4$ (1.5 equiv): (2) TBAF
[b] (1) CuCl$_2$ (5 mol%), PhC≡CMe (15 mol%), RMgX (2 equiv); 2) TBAF
[c] (1) CuCl$_2$ (5 mol%), PhC≡CMe (15 mol%), NMP (4 equiv), RMgX (2 equiv): 2) TBAF
[d] [α]$_D^{23}$ is too small to be determined
[e] Enantiomeric excess determined by $^1$H NMR analysis of Mosher esters
[f] Enantiomeric excess determined by $^1$H NMR analysis of 2-methoxy-2-(1-naphthyl)propionic acid esters
[g] Enantiomeric excess determined by chiral GC The determination of the enantiomeric purities of the chiral alkanols prepared by the processes of the present invention proved to be challenging. For most of alkanols where the stereogenic center generated was in the γ or δ position relative to OH group, such as compounds 19, 21, 22, 24, and 25, enantiomeric purities of ≥99% ee were successfully determined by chiral gas chromatography. The attempts to determine the enantiomeric excess in the more demanding cases, such as 5-alkyl-1-alcohols 31, 32, 33, 35, 36 and 4-alkyl-1-alcohols 23, 28, using chiral GC, HPLC chromatography and α-methoxy-α-(trifluoromethyl) phenylacetic acid (MTPA) ester analysis, were ineffective.

NMR spectroscopy is a convenient tool for the determination of enantiomeric purity and absolute configuration of chiral compounds, which is based on transformation of the chiral substrate with a suitable chiral derivatizing agent (CDA) to two different diastereoisomers or conformers that can be differentiated by NMR spectroscopy. Many CDAs including MTPA, 2-methoxy-2-phenylacetic acid (MPA), 2-methoxy-2-(1-naphthyl)acetic acid (NMA), 2-methoxy-2-(2-naphthyl)acetic acid (2NMA), 2-(9-anthryl)-2-methoxyacetic acid (9AMA), and 2-methoxy-2-(1-naphthyl)propionic acid (MαNP) have been developed for determining the absolute configurations or enantiomeric excess of secondary alcohols.

In the determination of the enantiomeric purities of the chiral alkanols, the challenges in dealing with primary alcohols stem from the fact that: (i) the distance between groups R$^1$/R$^2$ of primary alcohols and the aryl ring of CDA is greater than that in secondary alcohols, and thus leads to weaker shielding effect, and (ii) additional C—C bonds between the stereogenic center and CDA reduces the conformational preference by increasing the rotational freedom (FIG. 1). MTPA and SAMA were reported to be applied to assignment of absolute configuration or determination of enantiomeric excess of only β-chiral primary alcohols (Finamore, et al. *J. Org. Chem.* 1991, 56, 1146-1153; Ciminiello, et al. *Tetrahedron*, 2001, 57, 8189-8192). In cases where the two alkyl branches of β-chiral primary alcohols at the stereogenic center are closely similar to each other, such as C$_4$H$_9$(C$_3$H$_7$)CHCH$_2$OH, the chemical shifts of the diastereomeric MTPA esters were not sufficiently separated to allow quantitative determination of the enantiomeric purity by $^1$H NMR or $^{19}$F NMR analysis. Thus, development of a more efficient method for determination of the enantiomeric purity of γ- and more-remotely chiral primary alcohols is particularly in need.

The present invention provides a method for determination of the enantiomeric purity of γ- and more-remotely chiral primary alcohols by NMR analysis of MαNP esters.

Figure 2:
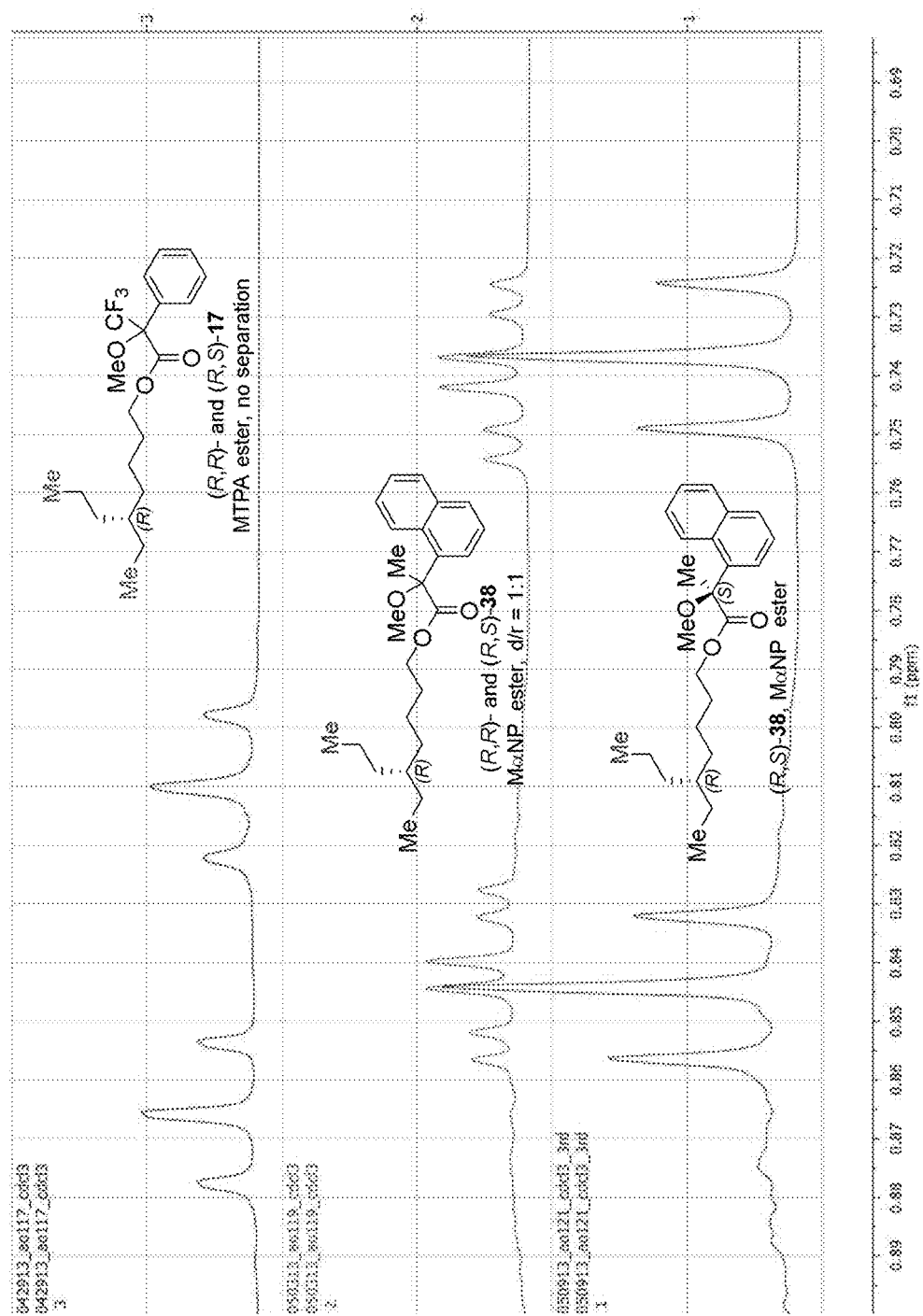
FIG. 2 depicts methyl resonances in the $^1$H NMR spectra (CDCl$_3$, 600 MHz) of MTPA ester and MαNP ester derived from (R)-19.

The MαNP acid is a very powerful CDA used in determination of the absolute configuration of chiral secondary alcohols. The MαNP esters contain very important features: (i) the naphthyl ring exerts greater anisotropic differential shielding effects on substituents than phenyl group; (ii) syn-syn conformation is taken as the stable and preferred conformation of MαNP esters (FIG. 1); and (iii) MαNP acid contains a chiral quaternary carbon, thus does not racemize during the derivatization reaction. Indeed, the terminal methyl groups of the diastereomeric MαNP ester (R,R)- and (S,R)-38, derived from alcohol (R)-31, showed completely separate $^1$H NMR signals, while the diastereomeric MTPA ester 37 had no separation (FIG. 2). The MαNP ester analysis was also successfully applied to determine enantiomeric excess of other δ- and ε-chiral primary alcohols 23, 26, 28, 32, 33, 35 and 36, which demonstrated surprising long-range anisotropic differential shielding effects. The diastereotopic chemical shift differences of MαNP esters were affected by NMR solvent and resonance frequency (MHz) of NMR. d-acetonitrile, d-acetone, d-methanol and/or CDCl$_3$ are suitable solvents. The higher the resonance frequency and the better discrimination of chemical shifts obtained. In some embodiments, for determination of the enantiomeric purity of a compound prepared by the process of the present invention, the compound can be converted into an MNPA ester. For example, for the compound of (R)-4-propylheptan-6,6,7,7,7-d$_5$-1-ol, the present invention provides a MNPA esters of formula (VI)

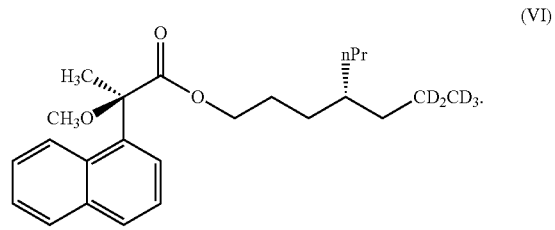

(VI)

Definitions

At various places in the present specification, substituents of compounds of the invention are disclosed in groups or in ranges. It is specifically intended that the invention include each and every individual subcombination of the members of such groups and ranges.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

In some embodiments, the term "alkyl" is meant to refer to a saturated hydrocarbon group which is straight-chained or branched. Example alkyl groups include methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like. An alkyl group can contain from 1 to about 20, from 2 to about 20, from 1 to about 10, from 1 to about 8, from 1 to about 6, from 1 to about 4, or from 1 to about 3 carbon atoms.

In some embodiments, the term "aryl" refers to monocyclic or polycyclic (e.g., having 2, 3 or 4 fused rings) aromatic hydrocarbons such as, for example, phenyl, naphthyl, anthracenyl, phenanthrenyl, and the like. In some embodiments, an aryl group has from 6 to about 20 carbon atoms.

In some embodiments, the term "cycloalkyl" refers to non-aromatic carbocycles including cyclized alkyl, alkenyl, and alkynyl groups. Cycloalkyl groups can include mono- or polycyclic (e.g., having 2, 3 or 4 fused rings) ring systems, including spirocycles. In some embodiments, cycloalkyl groups can have from 3 to about 20 carbon atoms, 3 to about 14 carbon atoms, 3 to about 10 carbon atoms, or 3 to 7 carbon atoms. Cycloalkyl groups can further have 0, 1, 2, 3 or more double bonds and/or 0, 1, 2 or more triple bonds. Also included in the definition of cycloalkyl are moieties that have one or more aromatic rings fused (i.e., having a bond in common with) to the cycloalkyl ring, for example, benzo derivatives of cyclopentane, cyclopentene, cyclohexane, and the like. A cycloalkyl group having one or more fused aromatic rings can be attached through either the aromatic or non-aromatic portion. One or more ring-forming carbon atoms of a cycloalkyl group can be oxidized, for example, having an oxo or sulfido substituent. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, adamantyl, and the like.

In some embodiments, the term "heteroaryl" refers to an aromatic heterocycle having at least one heteroatom ring member such as sulfur, oxygen, or nitrogen. Heteroaryl groups include monocyclic and polycyclic (e.g., having 2, 3, 4 or more fused rings) systems. Any ring-forming N atom in a heteroaryl group can also be oxidized to form an N-oxo moiety. Examples of heteroaryl groups include without limitation, pyridyl, N-oxopyridyl, pyrimidinyl, pyrazinyl, pyridazinyl, triazinyl, furyl, quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, indolinyl, and the like. In some embodiments, the heteroaryl group has from 1 to about 20 carbon atoms, and in further embodiments from about 3 to about 20 carbon atoms. In some embodiments, the heteroaryl group contains 3 to about 14, 3 to about 7, or 5 to 6 ring-forming atoms. In some embodiments, the heteroaryl group has 1 to about 4, 1 to about 3, or 1 to 2 heteroatoms.

In some embodiments, the term "cycloheteroalkyl" or "heterocycloalkyl" refers to a non-aromatic heterocycle where one or more of the ring-forming atoms is a heteroatom such as an O, N, or S atom. Cycloheteroalkyl or heterocycloalkyl groups can include mono- or polycyclic (e.g., having 2, 3 or 4 fused rings) ring systems as well as spirocycles. Example cycloheteroalkyl or heterocycloalkyl groups include morpholino, thiomorpholino, piperazinyl, tetrahydrofuranyl, tetrahydrothienyl, 2,3-dihydrobenzofuryl, 1,3-benzodioxole, benzo-1,4-dioxane, piperidinyl, pyrrolidinyl, isoxazolidinyl, isothiazolidinyl, pyrazolidinyl, oxazolidinyl, thiazolidinyl, imidazolidinyl, and the like. Also included in the definition of cycloheteroalkyl or heterocycloalkyl are moieties that have one or more aromatic rings fused (i.e., having a bond in common with) to the nonaromatic heterocyclic ring, for example phthalimidyl, naphthalimidyl, and benzo derivatives of heterocycles. A cycloheteroalkyl or heterocycloalkyl group having one or more fused aromatic rings can be attached though either the aromatic or non-aromatic portion. Also included in the definition of cycloheteroalkyl or heterocycloalkyl are moieties where one or more ring-forming atoms are substituted by 1 or 2 oxo or sulfido groups. In some embodiments, the cycloheteroalkyl or heterocycloalkyl group has from 1 to about 20 carbon atoms, and in further embodiments from about 3 to about 20 carbon atoms. In some embodiments, the cycloheteroalkyl or heterocycloalkyl group contains 3 to about 20, 3 to about 14, 3 to about 7, or 5 to 6 ring-forming atoms. In some embodiments, the cycloheteroalkyl or heterocycloalkyl group has 1 to about 4, 1 to about 3, or 1 to 2 heteroatoms. In some embodiments, the cycloheteroalkyl or heterocycloalkyl group contains 0 to 3 double bonds. In some embodiments, the cycloheteroalkyl or heterocycloalkyl group contains 0 to 2 triple bonds.

In some embodiments, the tem "halo" or "halogen" includes fluoro, chloro, bromo, and iodo.

In some embodiments, the term "substituted" refers to the replacement of a hydrogen moiety with a non-hydrogen moiety in a molecule or group. The term "mono-substituted" or "poly-substituted" means substituted with one or more than one substituent up to the valence of the substituted group. For example, a mono-substituted group can be substituted with 1 substituent, and a poly-substituted group can be substituted with 2, 3, 4, or 5 substituents. Generally when a list of possible substituents is provided, the substituents can be independently selected from that group.

Compounds of the invention can also include all isotopes of atoms occurring in the intermediates or final compounds. Isotopes include those atoms having the same atomic number but different mass numbers. For example, isotopes of hydrogen include tritium and deuterium.

Preparation of compounds of the invention can involve the protection and deprotection of various chemical groups. The need for protection and deprotection, and the selection of appropriate protecting groups can be readily determined by one skilled in the art. The chemistry of protecting groups can be found, for example, in T. W. Green and P. G. M. Wuts, *Protective Groups in Organic Synthesis,* 3rd. Ed., Wiley & Sons, Inc., New York (1999).

The invention will be further illustrated with reference to the following illustrative examples, which are not intended to limit the scope of the invention in any manner.

EXAMPLES

Example 1: Synthesis of (S)-3-iodo-2-methylpropan-1-ol ((S)-1a). Representative Procedure A

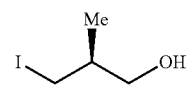

To a solution of allyl alcohol (0.68 mL, 10 mmol) in $CH_2Cl_2$ (5 mL) was added dropwise $Me_3Al$ (1.5 mL, 15 mmol) at −78° C., and the mixture was warmed to 23° C. and stirred for 1 h. To a solution of $Me_3Al$ (1.0 mL, 10 mmol) in $CH_2Cl_2$ (5 mL) was added dropwise $H_2O$ (0.18 mL, 10 mmol) at −78° C. under argon, and the mixture was stirred at 23° C. for 1 h to give a clear solution of MAO in $CH_2Cl_2$. To another solution of (+)-$(NMI)_2ZrCl_2$ (334 mg, 0.5 mmol) in $CH_2Cl_2$ (5 mL) were treated consecutively with $Me_3Al$ (1.0 mL, 10 mmol), MAO (10 mmol) prepared above, and the pretreated allyl alcohol solution prepared as described above at 0° C. After stirring overnight, the solvent and excess $Me_3Al$ were evaporated in vacuo. The residue was dissolved in THF (10 mL) and treated with $I_2$ (6.35 g, 25 mmol) in THF (10 mL) for 2 h at 0° C. The resultant mixture was quenched with water, extracted with Et₂O, washed with brine, dried, filtered, concentrated, and purified by column chromatography (silica gel, 20% ethyl acetate in hexanes) to afford the title product (1.6 g, 80% yield, 82% ee) as a pale-yellow oil. ¹H NMR (300 MHz, CDCl₃) δ 0.98 (d, J=6.4 Hz, 3H), 1.55-1.7 (m, 1H), 3.2-3.35 (m, 3H), 3.4-3.6 (m, 2H); ¹³C NMR (75 MHz, CDCl₃) δ 13.4, 17.1, 36.7, 66.3.

Example 2: Lipase-catalyzed Purification of (S)-3-Iodo-2-methyl-1-propanol ((S)-1a)

To a solution of (S)-1a (200 mg, 10 mmol, 82% ee) were added THF/H₂O (6 mL/6 μL), Amano PS (40 mg), and vinyl acetate (0.9 mL, 10 mmol), and the mixture was stirred for 4 h at 23° C. The reaction mixture was diluted with ether, filtered, concentrated, and purified by column chromatography (silica gel, 20% ethyl acetate in hexanes) to afford (S)-1a (126 mg, 63%). The optical purity was determined by Mosher ester analysis, ≥99% ee. [α]$_D^{23}$=+3.5° (c 1.0, CHCl₃).

Example 3: Synthesis of (R)-3-iodo-2-methylpropan-1-ol ((R)-1a)

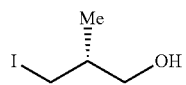

The title compound was prepared according to Representative Procedure A except (−)-(NMI)₂ZrCl₂ was used instead of (+)-(NMI)₂ZrCl₂. Yield: 81% with 84% ee determined by Mosher ester analysis. ¹H NMR (300 MHz, CDCl₃) δ 0.98 (d, J=6.4 Hz, 3H), 1.55-1.7 (m, 1H), 3.2-3.35 (m, 3H), 3.4-3.6 (m, 2H); ¹³C NMR (75 MHz, CDCl₃) δ 13.4, 17.1, 36.7, 66.3.

Example 4: Synthesis of (R)-3-iodo-2-methylpropyl acetate ((R)-2a)

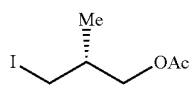

To a solution of (R)-1a (200 mg, 1.0 mmol, 84% ee) were added THF/H₂O (6 mL/6 μL), Amano PS (40 mg), and vinyl acetate (0.9 mL, 10 mmol), and the mixture was stirred for 5 h at 23° C. The resultant mixture was diluted with ether, filtered, concentrated, and purified by column chromatography (silica gel, 5% ethyl acetate in hexanes) to afford (R)-2a (145 mg, 60%) as a colorless oil. The optical purity was determined by Mosher ester analysis, ≥99% ee. [α]$_D^{23}$=−6.4° (c 1.0, CHCl₃). ¹H NMR (300 MHz, CDCl₃) δ 1.01 (d, J=6.3 Hz, 3H), 1.81-1.92 (m, 1H), 2.06 (s, 3H), 3.15-3.30 (m, 2H), 3.92 (m, 1H), 4.03 (m, 1H); ¹³C NMR (75 MHz, CDCl₃) δ 11.6, 17.1, 20.5, 33.7, 67.4, 170.1; HRMS calcd for C₆H₁₁IO₂ [M+H]⁺: 242.9882. found 242.9884.

Example 5: Synthesis of (S)-2-(Iodomethyl)pentan-1-ol ((S)-1c). Representative Procedure B

To a solution of allyl alcohol (0.68 mL, 10 mmol) in CH₂Cl₂ (5 mL) was added dropwise ⁿPr₃Al (2.9 mL, 15 mmol) at −78° C. under argon atmosphere, and the resultant solution was stirred at 23° C. for 1 h. To a solution of i-Bu₃Al (2.5 mL, 10 mmol) in CH₂Cl₂ (10 mL) was added dropwise H₂O (0.18 mL, 10 mmol) at −78° C. under argon, and the mixture was stirred at 23° C. for 1 h to give a clear solution of IBAO in CH₂Cl₂. To a solution of (+)-(NMI)₂ZrCl₂ (334 mg, 0.5 mmol) in CH₂Cl₂ (5 mL) at 0° C. were added consecutively ⁿPr₃Al (2.9 mL, 15 mmol), the IBAO solution prepared above, and the pretreated solution of allyl alcohol. The reaction mixture was warmed to 23° C. and stirred overnight. The solvents were evaporated in vacuo. The residue was dissolved in Et₂O (50 mL), and I₂ (15.3 g, 60 mmol) was introduced in three portions at 0° C. The resultant mixture was stirred for 2 h at 23° C., refluxed for additional 6 h. The reaction mixture was quenched with ice water, extracted with ether, washed with aq. Na₂S₂O₅, dried over anhydrous MgSO₄, filtered, concentrated, and purified by column chromatography (silica gel, 20% ethyl acetate in hexanes) to afford the title product (1.4 g, 59% yield, 82% ee) as a pale-yellow oil.

Example 6: Lipase-catalyzed Purification of (S)-2-(Iodomethyl)pentan-1-ol ((S)-1c)

To a solution of (S)-1c (228 mg, 1.0 mmol, 82% ee) were added THF/H₂O (6 mL/6 μL), Amano AK lipase (40 mg), and vinyl acetate (0.9 mL, 10 mmol), and the mixture was stirred for 12 h at 23° C. The resultant mixture was diluted with ether, filtered, concentrated, and purified by column chromatography (silica gel, 20% ethyl acetate in hexanes) to afford (S)-1c (132 mg, 58%). The optical purity was determined by Mosher ester analysis, ≥99% ee. [α]$_D^{23}$=−3.9° (c 1.4, CHCl₃). ¹H NMR (300 MHz, CDCl₃) δ 0.93 (t, J=6.6 Hz, 3H), 1.2-1.4 (m, 6H), 3.30 (dd, J=9.6, 5.1 Hz, 1H), 3.43 (dd, J=10.2, 4.2 Hz, 1H), 3.4-3.5 (m, 1H), 3.6-3.7 (m, 1H); ¹³C NMR (75 MHz, CDCl₃) δ 12.7, 14.0, 19.6, 32.9, 40.8, 64.9. HRMS calcd for C₆H₃IO [M]⁺: 228.0011. Found: 228.0015.

Example 7: Synthesis of (R)-2-(Iodomethyl)pentan-1-ol ((R)-1c)

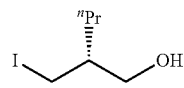

The title compound was prepared according to Representative Procedure B except (−)-(NMI)₂ZrCl₂ was used instead of (+)-(NMI)₂ZrCl₂. Yield: 60% with 80% ee determined by Mosher ester analysis. ¹H NMR (300 MHz, CDCl₃) δ 0.93 (t, J=6.6 Hz, 3H), 1.2-1.4 (m, 6H), 3.30 (dd, J=9.6, 5.1 Hz, 1H), 3.43 (dd, J=10.2, 4.2 Hz, 1H), 3.4-3.5 (m, 1H), 3.6-3.7

(m, 1H); $^{13}$C NMR (75 MHz, CDCl$_3$) δ 12.7, 14.0, 19.6, 32.9, 40.8, 64.9. HRMS calcd for C$_6$H$_3$IO [M]$^+$: 228.0011. Found: 228.0015.

Example 8: Synthesis of (R)-2-(iodomethyl)pentyl acetate ((R)-2c)

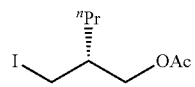

To a solution of (R)-1c (228 mg, 1.0 mmol, 80% ee) were added toluene (6 mL), Amano AK lipase (40 mg), and vinyl acetate (0.9 mL, 10 mmol), and the mixture was stirred for 2 h at 23° C. The resultant mixture was diluted with ether, filtered, concentrated, and purified by column chromatography (silica gel, 5% ethyl acetate in hexanes) to afford (R)-2c (132 mg, 50%) as a colorless oil. The optical purity was determined by Mosher ester analysis, ≥99% ee. $[α]_D^{23}$=−7.2° (c 1.6, acetone). $^1$H NMR (300 MHz, CDCl$_3$) δ 0.93 (m, 3H), 1.2-1.4 (m, 4H), 1.58-1.65 (m, 1H), 2.07 (s, 3H), 3.23-3.35 (m, 2H), 3.91 (dd, J=11.1, 7.5 Hz, 1H), 4.11 (dd, J=11.4, 4.8 Hz, 1H); $^{13}$C NMR (75 MHz, CDCl$_3$) δ 11.1, 14.0, 19.6, 20.9, 33.3, 38.1, 66.6, 170.8. HRMS calcd for C$_8$H$_{15}$IO$_2$[M]$^+$: 270.0117. Found: 270.0119.

Example 9: Synthesis of (S)-2-(iodomethyl)butan-1-ol ((S)-1b)

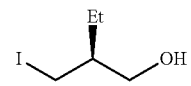

The title compound was prepared according to Representative Procedure B except Et$_3$Al was used instead of $^n$Pr$_3$Al. Yield: 60% with 87% ee determined by Mosher ester analysis. $^1$H NMR (300 MHz, CDCl$_3$) δ 0.94 (t, J=6.9 Hz, 3H), 1.2-1.4 (m, 3H), 1.82 (s, 1H), 3.31 (dd, J=9.6, 4.8 Hz, 1H), 3.42 (dd, J=9.9, 3.9 Hz, 1H), 3.50 (dd, J=11.1, 6.3 Hz, 1H), 3.64 (dd, J=10.8, 4.5 Hz, 1H); $^{13}$C NMR (75 MHz, CDCl$_3$) δ 11.1, 12.1, 23.8, 42.8, 64.8. HRMS calcd for C$_5$H$_{11}$IO [M]$^+$: 213.9855. Found: 213.9858.

Example 10: Lipase-catalyzed Purification of (S)-2-(Iodomethyl)pentan-1-ol ((S)-1b)

To a solution of (S)-1b (214 mg, 10 mmol, 87% ee) were added THF/H$_2$O (6 mL/6 μL), Amano AK lipase (40 mg), and vinyl acetate (0.9 mL, 10 mmol), and the mixture was stirred for 8 h at 23° C. The resultant mixture was diluted with ether, filtered, concentrated, and purified by column chromatography (silica gel, 20% ethyl acetate in hexanes) to afford (S)-1b (128 mg, 60%). The optical purity was determined by Mosher ester analysis, ≥99% ee. $[α]_D^{23}$=−4.9° (c 1.1, CHCl$_3$).

Example 11: Synthesis of (R)-2-(iodomethyl)butan-1-ol ((R)-1b)

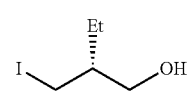

The title compound was prepared according to Representative Procedure B except Et$_3$Al and (−)-(NMI)$_2$ZrCl$_2$ was used instead of $^n$Pr$_3$Al and (+)-(NMI)$_2$ZrCl$_2$. Yield: 62% with 88% ee determined by Mosher ester analysis. $^1$H NMR (300 MHz, CDCl$_3$) δ 0.94 (t, J=6.9 Hz, 3H), 1.2-1.4 (m, 3H), 1.82 (s, 1H), 3.31 (dd, J=9.6, 4.8 Hz, 1H), 3.42 (dd, J=9.9, 3.9 Hz, 1H), 3.50 (dd, J=11.1, 6.3 Hz, 1H), 3.64 (dd, J=10.8, 4.5 Hz, 1H); $^{13}$C NMR (75 MHz, CDCl$_3$) δ 11.1, 12.1, 23.8, 42.8, 64.8. HRMS calcd for C$_5$H$_{11}$IO [M]$^+$: 213.9855. Found: 213.9858.

Example 12: Synthesis of (R)-2-(iodomethyl)butyl acetate ((R)-2b)

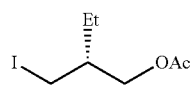

To a solution of (R)-1b (214 mg, 10 mmol, 88% ee) were added THF/H$_2$O (6 mL/6 μL), Amano PS (40 mg), and vinyl acetate (0.9 mL, 10 mmol), and the mixture was stirred for 10 h at 23° C. The resultant mixture was diluted with ether, filtered, concentrated, and purified by column chromatography (silica gel, 5% ethyl acetate in hexanes) to afford (R)-2b (133 mg, 52%) as a colorless oil. The optical purity was determined by Mosher ester analysis, ≥99% ee. $[α]_D^{23}$=−6.2° (c 1.2, acetone). $^1$H NMR (300 MHz, CDCl$_3$) δ 0.92 (t, J=7.5 Hz, 3H), 1.3-1.6 (m, 3H), 2.06 (s, 3H), 3.24-3.35 (m, 2H), 3.92 (dd, J=11.1, 7.2 Hz, 1H), 4.11 (dd, J=11.4, 4.8 Hz, 1H); $^{13}$C NMR (75 MHz, CDCl$_3$) δ 10.4, 10.9, 20.8, 24.2, 40.0, 66.4, 170.8. HRMS calcd for C$_7$H$_{13}$IO$_2$[M]$^+$: 255.9960. Found: 255.9963.

Example 13: Synthesis of (R)-2-methylbutan-1-ol ((R)-3) from (S)-1a

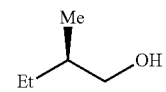

To a solution of (S)-1a (100 mg, 0.5 mmol), Li$_2$CuCl$_4$ (0.1 M in THF, 0.05 mL, 0.005 mmol) in THF (3 mL) was slowly added methylmagnesium chloride (3 M in ether, 0.5 mL, 3.0 mmol) at 0° C., and the resultant solution was stirred for 2 h at 0° C. and additional 1 h at 23° C. The reaction was then quenched with NH$_4$Cl (sat. aq.), extracted with Et$_2$O, dried over anhydrous MgSO$_4$, and concentrated carefully. The crude product was purified by column chromatography (silica gel, 25% Et$_2$O in pentane) to give the title product (34 mg, 77%) as a colorless oil. The optical purity was determined by Mosher ester analysis, ≥99% ee. $[α]_D^{23}$=+6.6° (c 1.3, CHCl$_3$), lit.[31] $[α]_D^{23}$=+5.85° (c 0.9, MeOH). $^1$H NMR (300 MHz, CDCl$_3$): δ 0.88-0.94 (m, 6H), 1.1-1.2 (m, 1H), 1.31 (s, 1H) 1.4-1.7 (m, 2H), 3.40-3.54 (m, 2H); $^{13}$C NMR (75 MHz, CDCl$_3$): δ 11.6, 16.4, 26.0, 37.6, 68.0.

Example 14: Synthesis of (R)-2-methylbutan-1-ol ((R)-3) from (R)-2b. Representative Procedure C

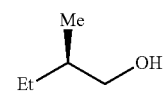

To a solution of (R)-2b (128 mg, 0.5 mmol) in THF (2 mL) was added LiAlH$_4$ (1 M in THF, 0.75 mL, 0.75 mmol) at 0° C., and the resultant solution was stirred for 2 h at 23° C. The reaction was quenched with NaOH (10% aq.) at 0° C., extracted with Et$_2$O, dried over MgSO$_4$, concentrated carefully, and purified by column chromatography (silica gel, 25% Et$_2$O in pentane) to give the title product (35 mg, 82%) as a colorless oil. The optical purity was determined by Mosher ester analysis, ≥99% ee. $[\alpha]_D^{23}$=+6.6° (c 1.3, CHCl$_3$), lit.[3] $[\alpha]_D^{23}$=+5.85° (c 0.9, MeOH). $^1$H NMR (300 MHz, CDCl$_3$): δ 0.88-0.94 (m, 6H), 1.1-1.2 (m, 1H), 1.31 (s, 1H) 1.4-1.7 (m, 2H), 3.40-3.54 (m, 2H); $^{13}$C NMR (75 MHz, CDCl$_3$): δ 11.6, 16.4, 26.0, 37.6, 68.0.

Example 15: Synthesis of (S)-2-methylbutan-1-ol ((S)-3)

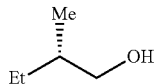

The title compound was prepared according to Representative Procedure C except (S)-2b was used instead of (R)-2b. Yield: 80% with 99% ee determined by Mosher ester analysis. $[\alpha]_D^{23}$=−6.5° (c 0.9, CHCl$_3$), lit.[4] $[\alpha]_D^{23}$=−6.58° (c 1.0, EtOH). $^1$H NMR (300 MHz, CDCl$_3$): δ 0.88-0.94 (m, 6H), 1.1-1.2 (m, 1H), 1.31 (s, 1H) 1.4-1.7 (m, 2H), 3.40-3.54 (m, 2H); $^{13}$C NMR (75 MHz, CDCl$_3$): δ 11.6, 16.4, 26.0, 37.6, 68.0.

Example 16: Synthesis of (R)-2-methylpent-4-en-1-ol ((R)-4). Representative Procedure D

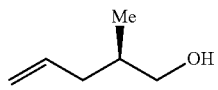

To a solution of (S)-1a (200 mg, 1.0 mmol) in DMF (1.5 mL) were added imidazole (172 mg, 2.5 mmol) and TBSCl (196 mg, 13 mmol) at 0° C., and the resultant solution was stirred for 12 h at 23° C., quenched with saturated NaHCO$_3$, extracted with Et$_2$O, dried over anhydrous MgSO$_4$, filtered, concentrated, and simply purified by a short silica gel column. The above product was dissolved in Et$_2$O (5 mL), and cooled to −78° C., $^t$BuLi (1.7 M in pentane, 1.2 ml, 2.0 mmol) was added. The resultant solution was stirred for 30 min at −78° C. Then, a solution of ZnBr$_2$ (225 mg, 1.0 mmol) in THF (3 mL) was introduced via canula at −78° C. and the resultant solution was warmed up to 0° C. and stirred for 30 min. Then, a solution of PdCl$_2$(DPEphos) (36 mg, 0.05 mmol) and vinyl bromide (0.44 mL, 8 mmol) in THF (1 mL) was added. The resultant mixture was stirred for 12 h at 23° C. The reaction was then quenched with NH$_4$Cl (sat. aq.), extracted with Et$_2$O, dried over anhydrous MgSO$_4$, concentrated. The crude product was dissolved in THF (2 mL) and TBAF (1 M in THF, 1.5 mL, 1.5 mmol) was added. The reaction was stirred for 2 h at 23° C., quenched with water, extracted with Et$_2$O, dried over anhydrous MgSO$_4$, concentrated, and purified by column chromatography (silica gel, 5% ethyl acetate in hexanes) to afford the title compound (85 mg, 85%) as a colorless oil. The optical purity was determined by Mosher ester analysis, ≥99% ee. $[\alpha]_D^{23}$=+2.3° (c 0.7, CH$_2$Cl$_2$), lit.[5] $[\alpha]_D^{23}$=+2.5° (c 1.5, CHCl$_3$). $^1$H NMR (300 MHz, CDCl$_3$) δ 0.91 (t, J=6.9 Hz, 3H), 1.65-1.8 (m, 1H), 1.85-2.0 (m, 1H), 2.1-2.3 (m, 1H), 3.4-3.55 (m, 2H), 4.9-5.1 (m, 2H), 5.7-5.9 (m, 1H); $^{13}$C NMR (75 MHz, CDCl$_3$) δ 16.3, 35.5, 37.8, 67.8, 116.0, 136.9.

Example 17: Synthesis of (S)-2-methylpentan-1-ol ((S)-5). Representative Procedure E

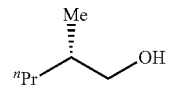

To a solution of (R)-2a (121 mg, 0.5 mmol), CuCl$_2$ (2 mg, 0.015 mmol), and 1-phenylpropyne (9.4 μL, 0.075 mmol) in THF (2 mL) was slowly added ethylmagnesium chloride (2 M in ether, 0.5 mL, 1.0 mmol) at 0° C., and the resultant solution was stirred for 2 h at 0° C. The reaction was then quenched with NH$_4$Cl (sat. aq.), extracted with Et$_2$O, dried over anhydrous MgSO$_4$, and concentrated carefurely. The crude product was dissolved in MeOH (0.2 mL), and KOH (3 M aq., 0.5 mL) was added. The reaction mixture was stirred at 23° C. for 1 h, diluted with a mixture of ether and NH$_4$Cl (sat. aq.), extracted with Et$_2$O, dried over anhydrous MgSO$_4$, concentrated and purified by column chromatography (silica gel, 20% ethyl acetate in hexanes) to give the title product (35 mg, 70%). The optical purity was determined by Mosher ester analysis, ≥99% ee. $[\alpha]_D^{23}$=−12.4° (c 1.0, CHCl$_3$), lit.[6] $[\alpha]_D^{23}$=−13.2° (c 2.0, MeOH). $^1$H NMR (300 MHz, CDCl$_3$): δ 0.89-0.92 (m, 6H), 1.0-1.1 (m, 1H), 1.2-1.4 (m, 3H), 1.50-1.65 (m, 1H), 3.41 (dd, J=10.5, 6.6 Hz, 1H), 3.51 (dd, J=10.5, 6.0 Hz, 1H); $^{13}$C NMR (75 MHz, CDCl$_3$): δ 14.3, 16.5, 20.0, 35.4 (2 C), 68.2.

Example 18: Synthesis of (R)-2-methylpentan-1-ol ((R)-5)

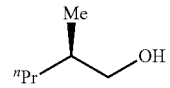

The title compound was prepared according to Representative Procedure C except (R)-2c was used instead of (R)-2b. Yield: 86% with 99% ee determined by Mosher ester analysis. $[\alpha]_D^{23}$=+12.2° (c 1.1, CHCl$_3$), lit.[6] $[\alpha]_D^{23}$=+12.3° (c 1.68, MeOH). $^1$H NMR (300 MHz, CDCl$_3$): δ 0.89-0.92 (m, 6H), 1.0-1.1 (m, 1H), 1.2-1.4 (m, 3H), 1.50-1.65 (m, 1H), 3.41 (dd, J=10.5, 6.6 Hz, 1H), 3.51 (dd, J=10.5, 6.0 Hz, 1H); $^{13}$C NMR (75 MHz, CDCl$_3$): δ 14.3, 16.5, 20.0, 35.4 (2 C), 68.2.

Example 19: (R)-2-ethylpentan-1-ol ((R)-6) from (S)-1b. Representative Procedure F

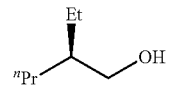

To a solution of (S)-1b (107 mg, 0.5 mmol), CuCl$_2$ (2 mg, 0.015 mmol), and 1-phenylpropyne (9.4 μL, 0.075 mmol) in THF (2 mL) was slowly added ethylmagnesium chloride (2 M in ether, 0.75 mL, 1.5 mmol) at 0° C., and the resultant solution was stirred for 2 h at 0° C. The reaction was then quenched with NH$_4$Cl (sat. aq.), extracted with Et$_2$O, dried over anhydrous MgSO$_4$, concentrated, and purified by column chromatography (silica gel, 20% ethyl acetate in hexanes) to give the title product (41 mg, 70%). $[\alpha]_D^{23}$=+3.2° (c 1.5, CHCl$_3$), lit.[7] $[\alpha]_D^{23}$=+3.36° (neat). $^1$H NMR (300 MHz, CDCl$_3$): δ 0.85-0.95 (m, 6H), 1.15 (m, 1H), 1.22-1.45 (m, 7H), 3.55 (dd, J=5.4, 5.4 Hz, 2H); $^{13}$C NMR (75 MHz, CDCl$_3$): δ 11.1, 14.5, 20.0, 23.3, 32.7, 41.7, 65.2. The optical purity of 99.7% ee was determined by Chiral GC analysis, CP-Chirasil-Dex CB capillary column (25 m×0.25 mm, 0.39 μM film). Test conditions: carrier gas 8 psi H$_2$, oven program (60° C. for 8 min, then 2° C./min to 90° C. for 20 min, then 20° C./min to 190° C. for 2 min), detector FID 200° C. Retention times (min): $t_R$ 24.8 (major); $t_S$ 25.4 (minor).

Example 20: Synthesis of (R)-2-ethylpentan-1-ol ((R)-6) from (R)-2c. Representative Procedure G

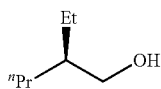

To a solution of (R)-2c (270 mg, 1.0 mmol) in THF (8 mL) were added consecutively Li$_2$CuCl$_4$ (0.1 M in THF, 0.5 mL, 0.05 mmol), and methylmagnesium chloride (3 M in ether, 1.1 mL, 3.3 mmol) at 0° C., and the resultant solution was stirred for 2 h at 0° C. The reaction was then quenched with NH$_4$Cl (sat. aq.), extracted with Et$_2$O, dried over MgSO$_4$, and concentrated. The crude product was dissolved in MeOH (0.5 mL) and aq. KOH (3 M, 1.0 mL) was added. After 1 h stirring, MeOH was evaporated via rotavapor and the residue was diluted with a mixture of ether and sat. NH$_4$Cl, extracted with Et$_2$O, dried over MgSO$_4$, concentrated and purified by column chromatography (silica gel, 20% ethyl acetate in hexanes) to give the title product (79 mg, 69%). $[\alpha]_D^{23}$=+3.2° (c 1.5, CHCl$_3$), lit.[7] $[\alpha]_D^{23}$=+3.36° (neat). $^1$H NMR (300 MHz, CDCl$_3$): δ 0.85-0.95 (m, 6H), 1.15 (m, 1H), 1.22-1.45 (m, 7H), 3.55 (dd, J=5.4, 5.4 Hz, 2H); $^{13}$C NMR (75 MHz, CDCl$_3$): δ 11.1, 14.5, 20.0, 23.3, 32.7, 41.7, 65.2.

Example 21: Synthesis of (R)-2-ethylhexan-1-ol ((R)-7)

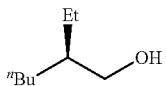

The title compound was prepared according to Representative Procedure F except n-propylmagnesium chloride was used instead of ethylmagnesium chloride. 72% yield with 99.7% ee determined by chiral GC analysis, CP-Chirasil-Dex CB capillary column (25 m×0.25 mm, 0.39 μM film). Test conditions: carrier gas 8 psi H$_2$, oven program (60° C. for 8 min, then 2° C./min to 90° C. for 20 min, then 20° C./min to 190° C. for 2 min), detector FID 200° C. Retention times (min): $t_R$ 32.2 (major); $t_S$ 33.1 (minor). $[\alpha]_D^{23}$=−3.6° (c 0.9, CHCl$_3$), lit.[8] $[\alpha]_D^{23}$=−3.3°. $^1$H NMR (300 MHz, CDCl$_3$): δ 0.85-0.92 (m, 6H), 1.22-1.45 (m, 10H), 3.54 (d, J=5.1 Hz, 2H); $^{13}$C NMR (75 MHz, CDCl$_3$): δ 10.9, 14.0, 23.0, 23.2, 29.0, 30.0, 41.8, 65.0.

Example 22: Synthesis of (S)-2-ethylhexan-1-ol ((S)-7)

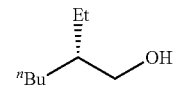

To a solution of (R)-2b (128 mg, 0.5 mmol), CuCl$_2$ (2 mg, 0.015 mmol), and 1-phenylpropyne (9.4 μL, 0.075 mmol) in THF (2 mL) was slowly added n-propylmagnesium chloride (2 M in ether, 0.75 mL, 1.5 mmol) at 0° C., and the resultant solution was stirred for 2 h at 0° C. The reaction was then quenched with NH$_4$Cl (sat. aq.), extracted with Et$_2$O, dried over anhydrous MgSO$_4$, concentrated. The crude product was dissolved in MeOH (0.2 mL) and aq. KOH (3 M, 0.5 mL) was added. After 1 h stirring at 23° C., MeOH was evaporated via rotavapor and the residue was diluted with a mixture of ether and sat. NH$_4$Cl, extracted with Et$_2$O, dried over MgSO$_4$, concentrated and purified by column chromatography (silica gel, 20% ethyl acetate in hexanes) to give the title product (45 mg, 70%). The optical purity of 99.3% ee was determined by chiral GC analysis, CP-Chirasil-Dex CB capillary column (25 m×0.25 mm, 0.39 μM film). Test conditions: carrier gas 8 psi H$_2$, oven program (60° C. for 8 min, then 2° C./min to 90° C. for 20 min, then 20° C./min to 190° C. for 2 min), detector FID 200° C. Retention times (min): $t_R$ 32.6 (minor); $t_S$ 33.3 (major). $[\alpha]_D^{23}$=+3.5° (c 0.8, CHCl$_3$), lit.[8] $[\alpha]_D^{23}$=+2.6°. $^1$H NMR (300 MHz, CDCl$_3$): δ 0.85-0.92 (m, 6H), 1.22-1.45 (m, 10H), 3.54 (d, J=5.1 Hz, 2H); $^{13}$C NMR (75 MHz, CDCl$_3$): δ 10.9, 14.0, 23.0, 23.2, 29.0, 30.0, 41.8, 65.0.

Example 23: Synthesis of (R)-2-ethylheptan-1-ol ((R)-8)

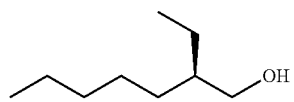

The title compound was prepared according to Representative Procedure F except n-butylmagnesium chloride was used instead of ethylmagnesium chloride. 75% yield with 99.8% ee determined by chiral GC analysis, CP-Chirasil-Dex CB capillary column (25 m×0.25 mm, 0.39 μM film). Test conditions: carrier gas 8 psi H$_2$, oven program (60° C. for 8 min, then 2° C./min to 90° C. for 20 min, then 20° C./min to 190° C. for 2 min), detector FID 200° C. Retention times (min): $t_R$ 44.3 (major); $t_S$ 44.7 (minor). $[\alpha]_D^{23}$=−6.2° (c 0.7, CHCl$_3$). $^1$H NMR (300 MHz, CDCl$_3$): δ 0.85-0.92 (m, 6H), 1.2-1.46 (m, 12H), 3.53 (d, J=5.1 Hz, 2H); $^{13}$C NMR (75 MHz, CDCl$_3$): δ 11.1, 14.0, 22.6, 23.3, 26.5, 30.4, 32.2, 42.0, 65.3.

Example 24: Synthesis of (S)-2-propyloctan-1-ol ((S)-9). Representative Procedure H

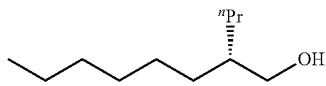

To a solution of (R)-2c (500 mg, 1.85 mmol) in THF (10 mL) were added consecutively N-methylpyrrolidone (0.72 mL, 7.4 mmol), Li$_2$CuCl$_4$ (0.1 M in THF, 0.55 mL, 0.055 mmol), and n-pentylmagnesium bromide (2 M in ether, 1.85 mL, 3.7 mmol) at 0° C., and the resultant solution was stirred for 2 h at 0° C. The reaction was then quenched with NH$_4$Cl (sat. aq.), extracted with Et$_2$O, dried over anhydrous MgSO$_4$, and concentrated. The crude product was dissolved in MeOH (1 mL), and KOH (3 M, 1.85 mL) was added. The reaction mixture was stirred at 23° C. for 1 h. The solvents were evaporated in vacuo and the residue was diluted with a mixture of ether and NH$_4$Cl (sat. aq.), extracted with Et$_2$O, dried over anhydrous MgSO$_4$, concentrated and purified by column chromatography (silica gel, 20% ethyl acetate in hexanes) to give the title product (254 mg, 80%). $[\alpha]_D^{23}=+1.5°$ (c 1.3, CHCl$_3$). $^1$H NMR (300 MHz, CDCl$_3$): δ 0.85-0.95 (m, 6H), 1.1-1.2 (m, 1H), 1.2-1.4 (m, 14H), 1.4-1.5 (m, 1H), 3.54 (d, J=5.1 Hz, 2H); $^{13}$C NMR (75 MHz, CDCl$_3$): δ 14.0, 14.4, 19.9, 22.6, 26.8, 29.7, 30.9, 31.9, 33.2, 40.2, 65.4. HRMS calcd for C$_{11}$H$_{24}$O [M]$^+$: 172.1827. Found: 172.1824. The optical purity of 99.5% ee was determined by chiral GC analysis, CP-Chirasil-Dex CB capillary column (25 m×0.25 mm, 0.39 μM film). Test conditions: carrier gas 8 psi H$_2$, oven program (60° C. for 8 min, then 2° C./min to 90° C. for 20 min, then 20° C./min to 190° C. for 2 min), detector FID 200° C. Retention times (min): t$_R$ 47.1 (minor); t$_S$ 47.2 (major).

Example 25: Synthesis of (R)-2-propyloctan-1-ol ((R)-9)

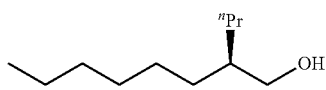

The title compound was prepared according to Representative Procedure H except (S)-2c was used instead of (R)-2c. 76% yield with 99.5% ee determined by chiral GC analysis, CP-Chirasil-Dex CB capillary column (25 m×0.25 mm, 0.39 μM film). Test conditions: carrier gas 8 psi H$_2$, oven program (60° C. for 8 min, then 2° C./min to 90° C. for 20 min, then 20° C./min to 190° C. for 2 min), detector FID 200° C. Retention times (min): t$_R$ 47.1 (major); t$_S$ 47.2 (minor). $[\alpha]_D^{23}=-1.6°$ (c 1.1, CHCl$_3$). $^1$H NMR (300 MHz, CDCl$_3$): δ 0.85-0.95 (m, 6H), 1.1-1.2 (m, 1H), 1.2-1.4 (m, 14H), 1.4-1.5 (m, 1H), 3.54 (d, J=5.1 Hz, 2H); $^{13}$C NMR (75 MHz, CDCl$_3$): δ 14.0, 14.4, 19.9, 22.6, 26.8, 29.7, 30.9, 31.9, 33.2, 40.2, 65.4. HRMS calcd for C$_{11}$H$_{24}$O [M]$^+$: 172.1827. Found: 172.1824.

Example 26: Synthesis of (R)-2-propylpent-4-en-1-ol ((R)-10)

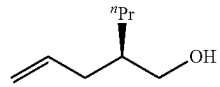

The title compound was prepared according to Representative Procedure D except (S)-1c was used instead of (S)-1a. 82% yield. $[\alpha]_D^{23}=+1.0°$ (c 0.8, acetone). $^1$H NMR (300 MHz, CDCl$_3$): δ 0.91 (t, J=6.9 Hz, 3H), 1.2-1.4 (m, 5H), 1.5-1.6 (m, 1H), 2.12 (dd, J=1.2, 6.3 Hz, 2H), 3.55 (dd, J=2.7, 6.0 Hz, 2H), 4.9-5.1 (m, 2H), 5.7-5.9 (m, 1H); $^{13}$C NMR (75 MHz, CDCl$_3$): δ 14.4, 20.1, 32.9, 35.8, 40.1, 65.6, 116.2, 137.2. HRMS calcd for C$_8$H$_{16}$O [M]$^+$: 128.1201. Found: 128.1204.

Example 27: Synthesis of (S)-2-propylhexan-1-ol ((S)-11)

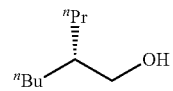

The title compound was prepared according to Representative Procedure G except n-propylmagnesium chloride was used instead of methylmagnesium chloride. 64% yield with 99.5% ee determined by chiral GC analysis, CP-Chirasil-Dex CB capillary column (25 m×0.25 mm, 0.39 μM film). Test conditions: carrier gas 8 psi H$_2$, oven program (60° C. for 8 min, then 2° C./min to 90° C. for 20 min, then 20° C./min to 190° C. for 2 min), detector FID 200° C. Retention times (min): t$_R$ 41.6 (minor); t$_S$ 42.4 (major). $[\alpha]_D^{23}=+0.36°$ (c 1.1, CHCl$_3$). $^1$H NMR (300 MHz, CDCl$_3$): δ 0.8-0.9 (m, 6H), 1.2-1.5 (m, 12H), 3.54 (dd, J=5.7 Hz, 2H); $^{13}$C NMR (75 MHz, CDCl$_3$): δ 14.3, 14.5, 20.0, 23.1, 29.1, 30.6, 33.2, 40.3, 65.7. HRMS calcd for C$_9$H$_{20}$O [M]$^+$: 144.1514. Found: 144.1518.

Example 28: Synthesis of (R)-2-propyloctanoic acid. (R)-Arundic acid. Representative Procedure I

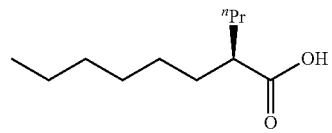

To a solution of (R)-9 (86 mg, 0.5 mmol), TEMPO (2,2,6,6-tetramethyl-1-piperidinyloxy free radical) (5.5 mg, 0.035 mmol) in CH$_3$CN (2.5 mL) and 0.67M sodium phosphate buffer (pH 6.7, 1.9 mL) were added consecutively a solution of NaClO$_2$ (90 mg, 1.0 mmol) in H$_2$O (0.5 mL), and a solution of dilute NaOCl, prepared by diluting 5.25% NaOCl (13 μL) with H$_2$O (0.25 mL). The mixture was stirred at 35° C. for 7 h and was cooled to 0° C. 1 M HCl (3.0 mL) was added to pH 3. The mixture was extracted with Et$_2$O, dried over anhydrous MgSO$_4$. After removing the volatiles in vacuo, the title product (88 mg, 95%) was as colorless oil. $[\alpha]_D^{23}=-6.4°$ (c 2.2, EtOH), lit.[10] $[\alpha]_D^{23}=-6.1°$ (c 2, EtOH); $^1$H NMR (300 MHz, CDCl$_3$): δ 0.8-0.9 (m, 6H), 1.2-1.5 (m, 12H), 1.5-1.6 (m, 2H), 2.3-2.4 (m, 1H); $^{13}$C NMR (75 MHz, CDCl$_3$): δ 13.9, 14.0, 20.5, 22.6, 27.3, 29.2, 31.7, 32.2, 34.3, 45.4, 183.5. The optical purity of 99.5% ee was determined by chiral GC analysis of the corresponding alcohol by reduction with LiAlH$_4$. CP-Chirasil-Dex CB capillary column (25 m×0.25 mm, 0.39 µM film). Test conditions: carrier gas 8 psi H$_2$, oven program (60° C. for 8 min, then 2° C./min to 90° C. for 20 min, then 20° C./min to 190° C. for 2 min), detector FID 200° C. Retention times (min): $t_R$ 47.1 (major); $t_S$ 47.2 (minor).

Example 29: Synthesis of (S)-2-propyloctanoic acid. (S)-Arundic acid

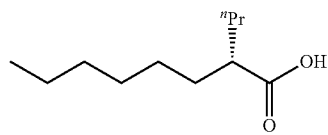

The title compound was prepared according to Representative Procedure I except (S)-9 was used instead of (R)-9. 95% yield with 99.5% ee determined by chiral GC analysis of the corresponding alcohol by reduction with LiAlH$_4$. CP-Chirasil-Dex CB capillary column (25 m×0.25 mm, 0.39 µM film). Test conditions: carrier gas 8 psi H$_2$, oven program (60° C. for 8 min, then 2° C./min to 90° C. for 20 min, then 20° C./min to 190° C. for 2 min), detector FID 200° C. Retention times (min): $t_R$ 47.1 (minor); $t_S$ 47.2 (major). $[\alpha]_D^{23}=+6.5°$ (c 2.2, EtOH), lit.[10] $[\alpha]_D^{23}=+6.6°$ (c 0.54, EtOH); $^1$H NMR (300 MHz, CDCl$_3$): δ 0.8-0.9 (m, 6H), 1.2-1.5 (m, 12H), 1.5-1.6 (m, 2H), 2.3-2.4 (m, 1H); $^{13}$C NMR (75 MHz, CDCl$_3$): δ 13.9, 14.0, 20.5, 22.6, 27.3, 29.2, 31.7, 32.2, 34.3, 45.4, 183.5.

Example 30: Synthesis of (S)-2-Ethylpentan-1-ol (6)

To a solution of (S)-1c (92 mg, 0.4 mmol, ≥99% ee), CuCl$_2$ (2.8 mg, 0.02 mmol), and 1-phenylpropyne (7.9 µL, 0.06 mmol) in THF (2 mL) was slowly added methylmagnesium chloride (3 M in THF, 0.44 mL, 1.32 mmol) at 0° C., and the resultant solution was stirred for 2 h at 0° C. The reaction was then quenched with aqueous NH$_4$Cl, extracted with Et$_2$O, dried over anhydrous MgSO$_4$, concentrated, and purified by column chromatography (silica gel, 20% ethyl acetate in hexanes) to give (S)-2-ethylpentan-1-ol (S)-6 (37 mg, 80%). The optical purity was determined by chiral GC analysis, ≥99% ee. $[\alpha]_D^{23}=+3.2°$ (c 1.2, CH$_2$Cl$_2$). $^1$H NMR (300 MHz, CDCl$_3$): δ 0.85-0.95 (m, 6H), 1.15 (m, 1H), 1.22-1.45 (m, 7H), 3.55 (dd, J=5.4, 5.4 Hz, 2H); $^{13}$C NMR (75 MHz, CDCl$_3$): δ 11.1, 14.5, 20.0, 23.3, 32.7, 41.7, 65.2. The optical purity of 99.3% ee was determined by Chiral GC analysis, CP-Chirasil-Dex CB capillary column (25 m×0.25 mm, 0.39 µM film). Test conditions: carrier gas 8 psi H$_2$, oven program (60° C. for 8 min, then 2° C./min to 90° C. for 20 min, then 20° C./min to 190° C. for 2 min), detector FID 200° C. Retention times (min): $t_R$ 25.18 (minor); $t_S$ 25.25 (major).

Example 31: (R)-5-((tert-Butyldimethylsilyl)oxy)-2-propylpentan-1-ol ((R)-15b). Representative Procedure J

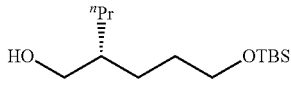

To a solution of $^i$Bu$_3$Al (5.0 mL, 20 mmol) in CH$_2$Cl$_2$ (20 mL) was added dropwise H$_2$O (0.36 mL, 20 mmol) at −78° C. under argon, and the mixture was slowly warmed to 23° C. and stirred for 2 h to give a clear solution of IBAO in CH$_2$Cl$_2$. To another solution of (−)-(NMI)$_2$ZrCl$_2$ (134 mg, 0.2 mmol) in CH$_2$Cl$_2$ (30 mL) were added consecutively $^n$Pr$_3$Al (8.4 mL, 44 mmol) and the IBAO solution prepared above. The mixture was cooled to 0° C. with an ice bath, and tert-butyldimethyl(pent-4-en-1-yloxy)silane (4.0 g, 20 mmol) was added dropwise. The resultant solution was stirred for 18 h at 0° C. The reaction mixture was treated with a vigorous stream of oxygen bubbled through it for 15 h at 0° C. The reaction was then quenched with 3M aqueous NaOH solution, extracted with Et$_2$O three times, washed by saturated aqueous NH$_4$Cl solution and brine, dried over anhydrous MgSO$_4$, concentrated, and purified by column chromatography (silica gel, 0 to 20% gradient ethyl acetate in hexanes) to afford the title product (3.75 g, 72% yield, 82% ee). $^1$H NMR (300 MHz, CDCl$_3$): δ 0.05 (s, 6H), 0.87-0.93 (m, 12H), 1.22-1.65 (m, 10H), 3.54 (dd, J=5.7, 2.7 Hz, 2H), 3.61 (t, J=6.3 Hz, 2H); $^{13}$C NMR (MHz, CDCl$_3$) δ −5.44 (2 C), 14.32, 18.21, 19.85, 25.83 (3 C), 26.73, 29.66, 33.13, 39.83, 63.51, 65.08. The optical purity of 82% ee was determined by Chiral GC analysis, CP-Chirasil-Dex CB capillary column (25 m×0.25 mm, 0.39 µM film). Test conditions: carrier gas 8 psi H$_2$, oven program (110° C. for 20 min, then 4° C./min to 150° C. for 11 min, then 20° C./min to 200° C. for 2 min), detector FID 200° C. Retention times (min): $t_R$35.93 (major); $t_S$ 36.28 (minor).

Example 32: Lipase-catalyzed purification of (R)-5-((tert-butyldimethylsilyl)oxy)-2-propylpentan-1-ol ((R)-15b)

To a solution of (R)-15b (260 mg, 1.0 mmol, 82% ee) were added anhydrous 1,2-dichloroethane (6 mL), Amano PS (40 mg), and vinyl acetate (0.9 mL, 10 mmol), and the mixture was stirred for 28 h at 23° C. The reaction mixture was diluted with ether, filtered, concentrated, and purified by column chromatography (silica gel, 20% ethyl acetate in hexanes) to afford (R)-15b (180 mg, 69%). The optical purity of ≥99% ee was determined by Chiral GC analysis. The optical purity of 82% ee was determined by Chiral GC analysis, CP-Chirasil-Dex CB capillary column (25 m×0.25 mm, 0.39 µM film). Test conditions: carrier gas 8 psi H$_2$, oven program (110° C. for 20 min, then 4° C./min to 150° C. for 11 min, then 20° C./min to 200° C. for 2 min), detector FID 200° C. Retention times (min): $t_R$35.92 (major); $t_S$ 36.28 (minor). $[\alpha]_D^{23}=+0.6°$ (c 5, CH$_2$Cl$_2$).

Example 33: (R)-4-((tert-Butyldimethylsilyl)oxy)-2-ethylbutan-1-ol ((R)-15a)

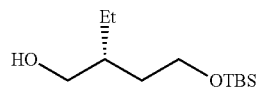

The title compound was prepared according to Representative Procedure J except Et$_3$Al and (but-3-en-1-yloxy)(tert-butyl)dimethylsilane were used instead of $^n$Pr$_3$Al and tert-butyldimethyl(pent-4-en-1-yloxy)silane.[2] Yield: 75% with 86% ee determined by Mosher ester analysis. $^1$H NMR (300 MHz, CDCl$_3$) δ 0.08 (s, 6H), 0.82-0.93 (m, 12H), 1.23-1.69 (m, 5H), 3.23-3.29 (m, 1H), 3.40-3.50 (m, 1H), 3.55-3.69 (m, 2H), 3.73-3.81 (m, 1H); $^{13}$C NMR (75 MHz, CDCl$_3$) δ −5.66 (2 C), 11.33, 18.04, 24.11, 25.69 (3 C), 34.86, 40.78, 61.72, 65.30.

Example 34: Lipase-catalyzed purification of (R)-4-((tert-butyldimethylsilyl)oxy)-2-ethylbutan-1-ol ((R)-15a)

To a solution of (R)-15a (232 mg, 10 mmol, 86% ee) were added anhydrous 1,2-dichloroethane (6 mL), Amano PS (40 mg), and vinyl acetate (0.9 mL, 10 mmol), and the mixture was stirred for 28 h at 23° C. The reaction mixture was diluted with ether, filtered, concentrated, and purified by column chromatography (silica gel, 20% ethyl acetate in hexanes) to afford (R)-15a (180 mg, 69%). The optical purity of ≥99% ee was determined by Mosher ester analysis. [α]$_D^{23}$=+4.4° (c 4.25, CH$_2$Cl$_2$).

Example 35: (S)-5-((tert-Butyldimethylsilyl)oxy)-2-propylpentan-1-ol ((S)-15b)

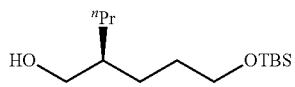

The title compound was prepared according to Representative Procedure J except (+)-(NMI)$_2$ZrCl$_2$ was used instead of (−)-(NMI)$_2$ZrCl$_2$. Yield: 67% with 85% ee determined by Chiral GC analysis, CP-Chirasil-Dex CB capillary column (25 m×0.25 mm, 0.39 μM film). Test conditions: carrier gas 8 psi H$_2$, oven program (110° C. for 20 min, then 4° C./min to 150° C. for 11 min, then 20° C./min to 200° C. for 2 min), detector FID 200° C. Retention times (min): t$_R$35.01 (minor); t$_S$ 35.19 (major). $^1$H NMR (300 MHz, CDCl$_3$): δ 0.05 (s, 6H), 0.87-0.93 (m, 12H), 1.22-1.65 (m, 10H), 3.54 (dd, J=5.7, 2.7 Hz, 2H), 3.61 (t, J=6.3 Hz, 2H); $^{13}$C NMR (MHz, CDCl$_3$) δ −5.44 (2 C), 14.32, 18.21, 19.85, 25.83 (3 C), 26.73, 29.66, 33.13, 39.83, 63.51, 65.08.

Example 36: Lipase-catalyzed purification of (S)-5-((tert-butyldimethylsilyl)oxy)-2-propylpentan-1-ol ((S)-15b)

To a solution of (S)-3b (651 mg, 2.5 mmol, 85% ee) in anhydrous 1,2-dichloroethane (15 mL) were added Amano PS lipase (100 mg) and vinyl acetate (2.3 mL, 25 mmol), and the mixture was stirred for 36 h at 23° C. The resultant mixture was diluted with ether, filtered, concentrated, and purified by column chromatography (silica gel, 20% ethyl acetate in hexanes). The purified product was added MeOH (6 mL) and KOH (168 mg, 3 mmol). The reaction mixture was stirred for 4 h at 23° C. The resultant mixture was concentrated, then extracted with Et$_2$O three times, washed by saturated aqueous NH$_4$Cl solution and brine, dried over anhydrous MgSO$_4$, concentrated to afford (S)-15b (534 mg, 82% yield, 97.6% ee). The same procedure above was repeated for further purification of obtained compound, then (S)-15b (435 mg, 70% yield, 99.6% ee) was obtained. [α]$_D^{23}$=−0.59° (c 4.01, CH$_2$Cl$_2$). The optical purity of 99.6% ee was determined by Chiral GC analysis, CP-Chirasil-Dex CB capillary column (25 m×0.25 mm, 0.39 μM film). Test conditions: carrier gas 8 psi H$_2$, oven program (110° C. for 20 min, then 4° C./min to 150° C. for 11 min, then 20° C./min to 200° C. for 2 min), detector FID 200° C. Retention times (min): t$_R$35.01 (minor); t$_S$ 35.19 (major).

Example 37: (R)-6-((tert-Butyldimethylsilyloxy)-2-propylhexan-1-ol ((R)-15c)

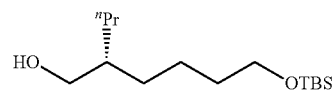

The title compound was prepared according to Representative Procedure J except tert-butyl(hex-5-en-1-yloxy)dimethylsilane and 3 mol % (−)-(NMI)$_2$ZrCl$_2$ were used instead of tert-butyldimethyl(pent-4-en-1-yloxy)silane and 1 mol % (−)-(NMI)$_2$ZrCl$_2$. Yield: 68% with 80% ee determined by Chiral GC analysis, CP-Chirasil-Dex CB capillary column (25 m×0.25 mm, 0.39 μM film). Test conditions: carrier gas 8 psi H$_2$, oven program (140° C. for 20 min, then 1° C./min to 150° C. for 0 min, then 20° C./min to 200° C. for 7.5 min), detector FID 200° C. Retention times (min): t$_R$ 27.33 (major); t$_S$ 27.83 (minor). $^1$H NMR (400 MHz, CDCl$_3$) δ −0.06 (s, 6H), 0.79 (s, 9H), 1.02-1.29 (m, 9H), 1.34-1.45 (m, 3H), 3.25 (s, 1H), 3.36 (d, J=5.6 Hz, 2H), 3.50 (t, J=6.4 Hz, 2H); $^{13}$C NMR (101 MHz, CDCl$_3$) δ −5.54 (2 C), 14.25, 18.07, 19.77, 22.77, 25.72 (3 C), 30.44, 32.98, 33.02, 40.01, 62.90, 64.91.

Example 38: Lipase-catalyzed purification of (R)-6-((tert-butyldimethylsilyl)oxy)-2-propylhexan-1-ol ((R)-15c)

To a solution of (R)-15c (824 mg, 3.0 mmol, 80% ee) was added anhydrous 1,2-dichloroethane (18 mL), Amano PS lipase (120 mg), and vinyl acetate (2.8 mL, 30 mmol) at 0° C., and the mixture was stirred for 39 h at 0° C. The resultant mixture was diluted with ether, filtered, concentrated, and purified by column chromatography (silica gel, 20% ethyl acetate in hexanes) to afford (R)-3c (496 mg, 60% yield, >99% ee). The optical purity was determined by Chiral GC analysis, CP-Chirasil-Dex CB capillary column (25 m×0.25 mm, 0.39 μM film). Test conditions: carrier gas 8 psi H$_2$, oven program (140° C. for 20 min, then 1° C./min to 150° C. for 0 min, then 20° C./min to 200° C. for 7.5 min), detector FID 200° C. Retention times (min): t$_R$ 27.33 (major); t$_S$ 27.83 (minor). [α]$_D^{23}$=+0.39° (c 7.3, CH$_2$Cl$_2$).

Example 39: (R)-4-((tert-Butyldimethylsilyl)oxy)-2-ethylbutyl 4-methylbenzenesulfonate ((R)-17). Representative Procedure K

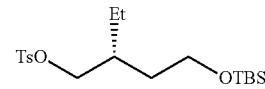 [SMILES: CC[C@H](CCO[Si](C)(C)C(C)(C)C)COS(=O)(=O)c1ccc(C)cc1]

To a solution of (R)-15a (442 mg, 1.9 mmol, ≥99% ee) and triethylamine (0.53 mL, 3.8 mmol) in CH$_2$Cl$_2$ (2 mL)

was slowly added a solution of tosyl chloride (546 mg, 2.9 mmol) and N,N-dimethylaminopyridine (47 mg, 0.38 mmol) in CH$_2$Cl$_2$ at 0° C., and the resultant solution was stirred overnight. The reaction was then quenched with aqueous NH$_4$Cl, extracted with EtOAc, washed by brine, dried over anhydrous MgSO$_4$, concentrated, and purified by column chromatography (silica gel, 2% ethyl acetate in hexanes) to give title product (705 mg, 95%). $[\alpha]_D^{23}$=−3.9° (c 2.6, CH$_2$Cl$_2$). $^1$H NMR (300 MHz, CDCl$_3$) δ −0.01 (s, 6H), 0.77-0.88 (m, 12H), 1.25-1.79 (m, 5H), 2.44 (s, 3H), 3.51-3.57 (m, 2H), 3.89-4.02 (m, 2H), 7.33 (d, J=8.4 Hz, 2H), 7.78 (d, J=8.4 Hz, 2H); $^{13}$C NMR (75 MHz, CDCl$_3$) δ −5.65 (2 C), 10.59, 17.97, 21.40, 23.11, 25.69 (3 C), 32.99, 35.92, 60.28, 72.28, 127.69 (2 C), 129.63 (2 C), 132.84, 144.46.

Example 40: (R)-3-Methylpentan-1-ol ((R)-18). Representative Procedure L

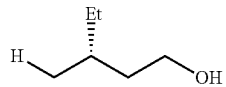

To a solution of (R)-17 (193 mg, 0.5 mmol) in THF (2 mL) was added LiAlH$_4$ (1 M in THF, 0.75 mL, 0.75 mmol) at 0° C., and the resultant solution was stirred for 2 h at 23° C. The reaction was quenched with NaOH (10% aq.) at 0° C., extracted with Et$_2$O, dried over MgSO$_4$, concentrated. The residue was dissolved in THF (1 mL), and TBAF (1 M in THF, 1 mL, 1 mmol) was added at 0° C., and the resulting solution was stirred for 3 h at 23° C. The reaction mixture was then quenched with brine, extracted with Et$_2$O, dried with MgSO$_4$, concentrated carefully, and purified by column chromatography (silica gel, 25% Et$_2$O in pentane) to give the title product (40 mg, 78%) as a colorless oil. The optical purity was determined by Mosher ester analysis, ≥99% ee. $[\alpha]_D^{23}$=−7.5° (c 0.5, CH$_2$Cl$_2$). $^1$H NMR (300 MHz, CDCl$_3$): δ 0.82-0.92 (m, 6H), 1.10-1.22 (m, 1H), 1.28-1.65 (m, 5H), 3.58-3.73 (m, 2H); $^{13}$C NMR (75 MHz, CDCl$_3$): δ 11.14, 19.00, 29.49, 30.98, 39.34, 60.83.

Example 41: (S)-3-Ethylhexan-1-ol ((S)-19). Representative Procedure M

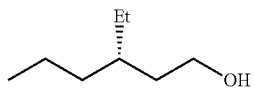

To a solution of (R)-17 (116 mg, 0.3 mmol), CuCl$_2$ (2 mg, 0.015 mmol), 1-phenyl-1-propyne (5.9 μL, 0.045 mmol) in THF (2 mL) was slowly added EtMgCl (2 M in ether, 0.3 mL, 0.6 mmol) at 0° C., and the resulting solution was stirred for 1 h at 23° C., and was stirred further for 4 h at 70° C. The reaction mixture was then quenched with aqueous NH$_4$Cl, extracted with Et$_2$O, washed by brine, dried with MgSO$_4$, and concentrated. The residue was dissolved in THF (1 mL), and TBAF (1 M in THF, 0.6 mL, 0.6 mmol) was added at 0° C., and the resulting solution was stirred for 3 h at 23° C. The reaction mixture was then quenched with ice water, extracted with Et$_2$O, washed by brine, dried with MgSO$_4$, concentrated, and purified by column chromatography (silica gel, 20% ethyl acetate in hexanes) to afford the title product (32 mg, 83%). $^1$H NMR (300 MHz, CDCl$_3$) δ 0.8-0.9 (m, 6H), 1.15-1.45 (m, 14H), 1.5-1.6 (m, 2H), 3.62 (t, J=6.3 Hz, 2H); $^{13}$C NMR (75 MHz, CDCl$_3$) δ 14.1, 14.5, 19.7, 23.1, 28.8, 29.5, 29.9, 33.2, 35.9, 36.9, 63.5. The optical purity was determined by chiral GC analysis, ≥99% ee. $[\alpha]_D^{23}$=+1.8° (c 1.2, CH$_2$Cl$_2$). $^1$H NMR (300 MHz, CDCl$_3$): δ 0.82-0.92 (m, 6H), 1.18-1.56 (m, 10H), 3.66 (d, J=7.2, 2 H); $^{13}$C NMR (75 MHz, CDCl$_3$): δ 10.68, 14.43, 19.71, 25.94, 35.38, 35.57, 36.47, 61.28. The optical purity of 99.7% ee was determined by Chiral GC analysis, CP-Chirasil-Dex CB capillary column (25 m×0.25 mm, 0.39 μM film). Test conditions: carrier gas 8 psi H$_2$, oven program (80° C. for 35 min, then 2° C./min to 90° C. for 5 min, then 30° C./min to 200° C. for 1 min), detector FID 200° C. Retention times (min): t$_R$ 39.95 (major); t$_S$ 41.04 (minor).

Example 42: (R)-5-((tert-Butyldimethylsilyl)oxy)-2-propylpentyl 4-methylbenzenesulfonate ((R)-20a)

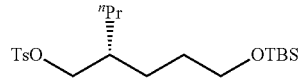

The title compound was prepared according to Representative Procedure K except (R)-15b was used instead of (R)-15a. Yield: 98%. $[\alpha]_D^{23}$=+0.72° (c 5.2, CH$_2$Cl$_2$). $^1$H NMR (300 MHz, CDCl$_3$): δ 0.02 (s, 6H), 0.79-0.92 (m, 12H), 1.15-1.43 (m, 8H), 1.58-1.68 (m, 1H), 2.44 (s, 3H), 3.52 (t, J=6.0 Hz, 2H), 3.91 (d, J=6.0 Hz, 2H), 7.34 (d, J=7.8 Hz, 2H), 7.78 (d, J=7.8 Hz, 2H); $^{13}$C NMR (75 MHz, CDCl$_3$) δ 144.42, 132.86, 129.60 (2 C), 127.66 (2 C), 72.53, 62.82, 36.93, 32.58, 29.42, 26.58, 25.74 (3 C), 21.39, 19.37, 18.07, 13.98, −5.52 (2 C).

Example 43: (R)-tert-Butyl((4-(iodomethyl)heptyl)oxy)dimethylsilane ((R)-20b). Representative Procedure N

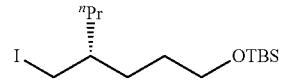

To a solution of 89 mg (1.3 mmol) of imidazole and 288 mg (1.1 mmol) of PPh$_3$ in CH$_2$Cl$_2$ (2 mL) was added 279 mg (1.1 mmol) of I$_2$ at 0° C. After stirring for 15 min at 0° C., (R)-15b (260 mg, 1.0 mmol, ≥99% ee) in CH$_2$Cl$_2$ (1 mL) was added to above solution. The mixture was stirred for 4 h at 23° C. The reaction mixture was then quenched with aqueous Na$_2$S$_2$O$_3$ and water, extracted with EtOAc, washed by brine, dried over MgSO$_4$, concentrated and purified by column chromatography (silica gel, 99/1 hexanes-EtOAc) to afford the title product (351 mg, 95% yield). $[\alpha]_D^{23}$=−2.3° (c 5, CH$_2$Cl$_2$). $^1$H NMR (300 MHz, CDCl$_3$): δ 0.06 (s, 6H), 0.87-0.94 (s, 9H, t, 3H), 1.10-1.65 (m, 9H), 3.28 (d, J=3.0 Hz, 2H), 3.61 (t, J=6.0 Hz, 2H); $^{13}$C NMR (MHz, CDCl$_3$) δ −5.12 (2 C), 14.26, 16.44, 18.41, 19.74, 26.05 (3 C), 29.78, 30.67, 36.67, 38.27, 63.14.

Example 44: (R)-4-Methylheptan-1-ol ((R)-21)

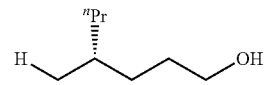

The title compound was prepared according to Representative Procedure L except (R)-20a was used instead of (R)-5. Yield: 82%. [α]$_D^{23}$=+1.5° (c 0.85, CH$_2$Cl$_2$). $^1$H NMR (300 MHz, CDCl$_3$): δ 0.84-0.92 (m, 6H), 1.05-1.59 (m, 10H), 3.58-3.73 (d, J=6.9 Hz, 2H); $^{13}$C NMR (75 MHz, CDCl$_3$): δ 14.30, 19.51, 20.04, 30.23, 32.28, 32.88, 39.22, 63.28. The optical purity of ≥99.1% ee was determined by Chiral GC analysis, CP-Chirasil-Dex CB capillary column (25 m×0.25 mm, 0.39 μM film). Test conditions: carrier gas 8 psi H$_2$, oven program (80° C. for 35 min, then 2° C./min to 90° C. for 5 min, then 30° C./min to 200° C. for 1 min), detector FID 200° C. Retention times (min): t$_S$ 39.10 (minor); t$_R$ 39.47 (major).

Example 45: (R)-4-Ethylheptan-1-ol ((R)-22)

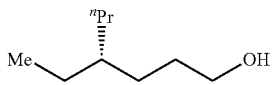

The title compound was prepared according to Representative Procedure M except (R)-20a and MeMgCl were used instead of (R)-5 and EtMgCl. Yield: 82%. [α]$_D^{23}$=−0.8° (c 0.8, CH$_2$Cl$_2$). $^1$H NMR (300 MHz, CDCl$_3$): δ 0.80-0.90 (m, 6H), 1.18-1.36 (m, 9H), 1.48-1.66 (m, 3H), 3.61 (t, J=6.9 Hz, 2H); $^{13}$C NMR (75 MHz, CDCl$_3$) δ 10.77, 14.47, 19.76, 25.77, 29.00, 29.92, 35.44, 38.39, 63.50. The optical purity of ≥99% ee was determined by Chiral GC analysis, CP-Chirasil-Dex CB capillary column (25 m×0.25 mm, 0.39 μM film). Test conditions: carrier gas 6 psi H$_2$, oven program (45° C. for 2 min, then 0.3° C./min to 65° C. for 0 min, then 0.1° C./min to 80° C. for 50 min, then 30° C./min to 200° C. for 3 min), detector FID 200° C. Retention times (min): t$_R$204 (major); t$_S$ 207 (minor).

Example 46: (S)-4-Propyloctan-1-ol ((S)-23)

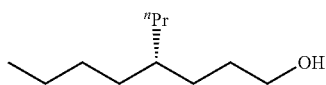

The title compound was prepared according to Representative Procedure M except (R)-20a and $^n$PrMgCl were used instead of (R)-17 and EtMgCl. Yield: 85%. [α]$_D^{23}$ is too small to be determined. $^1$H NMR (300 MHz, CDCl$_3$): δ 0.84-0.92 (m, 6H), 1.18-1.60 (m, 16H), 3.62 (t, J=6.6 Hz, 2H); $^{13}$C NMR (75 MHz, CDCl$_3$) δ 14.12, 14.47, 19.74, 23.11, 28.84, 29.48, 29.89, 33.22, 35.94, 36.93, 63.53. The optical purity of ≥99% ee was determined by $^1$H NMR analysis of 2-methoxy-2-(1-naphthyl)propionic acid ester.

Example 47: (R)-6-Methyl-4-propylheptan-1-ol ((R)-12)

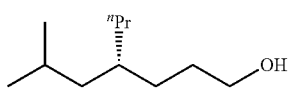

The title compound was prepared according to Representative Procedure M except (R)-20a and $^i$PrMgCl were used instead of (R)-17 and EtMgCl. Yield: 78%. [α]$_D^{23}$ is too small to be determined. $^1$H NMR (300 MHz, CDCl$_3$): δ 0.82-0.92 (m, 9H), 1.04-1.70 (m, 13H), 3.61 (t, J=6.6 Hz, 2H); $^{13}$C NMR (101 MHz, CDCl$_3$) δ 14.48, 19.53, 22.92 (2 C), 25.25, 29.66 (2 C), 34.48, 36.14, 43.69, 63.55. The optical purity of ≥99% ee was determined by Chiral GC analysis, CP-Chirasil-Dex CB capillary column (25 m×0.25 mm, 0.39 μM film). Test conditions: carrier gas 6 psi H$_2$, oven program (35° C. for 2 min, then 0.2° C./min to 60° C. for 840 min, then 30° C./min to 200° C. for 3 min), detector FID 200° C. Retention times (min): t$_R$791 (major); t$_S$ 804 (minor).

Example 48: (R)-4-(4-Methylbenzyl)heptan-1-ol ((R)-25)

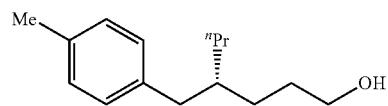

To a solution of (R)-tert-butyl((4-(iodomethyl)heptyl)oxy)dimethylsilane 20b (111 mg, 0.3 mmol) in Et$_2$O (1 mL) was added $^t$BuLi (1.7 M in pentane, 1.2 ml, 2.0 mmol) at −78° C. The resultant solution was stirred for 30 min at −78° C. Then a solution of ZnBr$_2$ (68 mg, 0.3 mmol) in THF (1 mL) was introduced via canula at −78° C. and the resultant solution was warmed up to 0° C. and stirred for 30 min. Then, a solution of Pd($^t$Bu$_3$P)$_2$ (7.6 mg, 0.015 mmol) and 4-iodotoluene (98 mg, 0.45 mmol) in DMF (1 mL) was added. The resultant mixture was stirred overnight at 23° C. The reaction was then quenched with aqueous NH$_4$Cl, extracted with EtOAc, washed by brine, dried over anhydrous MgSO$_4$, concentrated. The crude product was dissolved in THF (1 mL) and TBAF (1 M in THF, 0.6 mL, 0.6 mmol) was added. The reaction was stirred for 3 h at 23° C., quenched with water, extracted with EtOAc, washed by brine, dried over anhydrous MgSO$_4$, concentrated, and purified by column chromatography (silica gel, 20% ethyl acetate in hexanes) to afford the title compound (41 mg, 63%) as a colorless oil. [α]$_D^{23}$=++° (c++, CH$_2$Cl$_2$). $^1$H NMR (300 MHz, CDCl$_3$): δ 0.87 (t, J=6.9 Hz, 3H), 1.18-1.68 (m, 10 H), 2.32 (s, 3H), 2.43-2.58 (m, 2H), 3.59 (t, J=6.9 Hz, 2H), 7.01-7.09 (m, 4H); $^{13}$C NMR (75 MHz, CDCl$_3$) δ 138.19, 134.86, 128.89 (2 C), 128.70 (2 C), 63.36, 40.06, 39.30, 35.55, 29.84, 29.03, 21.06, 19.77, 14.47. The optical purity of 99.5% ee was determined by Chiral GC analysis, CP-Chirasil-Dex CB capillary column (25 m×0.25 mm, 0.39 μM film). Test conditions: carrier gas 8 psi H$_2$, oven program (100° C. for 20 min, then 1° C./min to 120° C. for 170 min, then 20° C./min to 200° C. for 5 min), detector FID 200° C. Retention times (min): t$_S$ 168.19 (minor); t$_R$ 169.79 (major).

Example 49: (R,E)-Ethyl 8-hydroxy-5-propyloct-2-enoate ((R)-26)

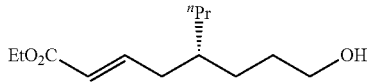

To a solution of (R)-tert-butyl((4-(iodomethyl)heptyl)oxy)dimethylsilane 20b (111 mg, 0.3 mmol) in Et$_2$O (1 mL) was added $^t$BuLi (1.7 M in pentane, 1.2 ml, 2.0 mmol) at −78° C. The resultant solution was stirred for 30 min at −78° C. Then a solution of ZnBr$_2$ (68 mg, 0.3 mmol) in THF (1 mL) was introduced via canula at −78° C. and the resultant solution was warmed up to 0° C. and stirred for 30 min. Then, a solution of PEPPSI-IPr (10 mg, 0.015 mmol) and (E)-ethyl 3-bromoacrylate (80 mg, 0.45 mmol) in THF (1 mL) was added. The resultant mixture was stirred overnight at 23° C. The reaction was then quenched with aqueous NH$_4$Cl, extracted with EtOAc, washed by brine, dried over anhydrous MgSO$_4$, concentrated. The crude product was dissolved in THF (1 mL) and TBAF (1 M in THF, 0.6 mL, 0.6 mmol) was added. The reaction was stirred for 3 h at 23° C., quenched with water, extracted with EtOAc, washed by brine, dried over anhydrous MgSO$_4$, concentrated, and purified by column chromatography (silica gel, 20% ethyl acetate in hexanes) to afford the title compound (42 mg, 61%) as a colorless oil. $[\alpha]_D^{23}$=+1.8° (c 0.67, CH$_2$Cl$_2$). $^1$H NMR (300 MHz, CDCl$_3$): δ 0.87 (t, J=6.9 Hz, 3H), 1.20-1.60 (m, 13H), 2.14-2.20 (m, 2H), 3.61 (t, J=6.6 Hz, 2H), 4.17 (q, J=6.9 Hz, 2H), 5.77-5.84 (m, 1H), 6.86-6.97 (m, 1H); $^{13}$C NMR (75 MHz, CDCl$_3$) δ 14.37 (2 C), 19.83, 29.60, 29.92, 35.81, 36.51, 36.94, 60.18, 63.17, 122.43, 147.88, 166.45. The optical purity of 99% ee was determined by $^1$H NMR analysis of 2-methoxy-2-(1-naphthyl)propionic acid ester.

Example 50: (S)-5-((tert-Butyldimethylsilyloxy)-2-propylpentyl 4-methylbenzenesulfonate ((S)-20a)

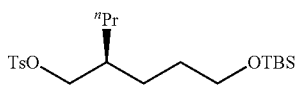

The title compound was prepared according to Representative Procedure K except (S)-15b was used instead of (R)-15a. Yield: 98%. $[\alpha]_D^{23}$=−0.75° (c 2.47, CH$_2$Cl$_2$). $^1$H NMR (300 MHz, CDCl$_3$): δ 0.02 (s, 6H), 0.79-0.92 (m, 12H), 1.15-1.43 (m, 8H), 1.58-1.68 (m, 1H), 2.44 (s, 3H), 3.52 (t, J=6.0 Hz, 2H), 3.91 (d, J=6.0 Hz, 2H), 7.34 (d, J=7.8 Hz, 2H), 7.78 (d, J=7.8 Hz, 2H); $^{13}$C NMR (75 MHz, CDCl$_3$) δ −5.52 (2 C), 13.98, 18.07, 19.37, 21.39, 25.74 (3 C), 26.58, 29.42, 32.58, 36.93, 62.82, 72.53, 127.66 (2 C), 129.60 (2 C), 132.86, 144.42.

Example 51: (S)-tert-Butyl((4-(iodomethyl)heptyl)oxy)dimethylsilane ((S)-20b)

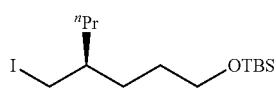

The title compound was prepared according to Representative Procedure N except (S)-15b was used instead of (R)-15a. Yield: 88%. $[\alpha]_D^{23}$=+2.21° (c 6.81, CH$_2$Cl$_2$). $^1$H NMR (300 MHz, CDCl$_3$): δ 0.06 (s, 6H), 0.87-0.94 (s, 9H, t, 3H), 1.10-1.65 (m, 9H), 3.28 (d, J=3.0 Hz, 2H), 3.61 (t, J=6.0 Hz, 2H); $^{13}$C NMR (MHz, CDCl$_3$) δ −5.12 (2 C), 14.26, 16.44, 18.41, 19.74, 26.05 (3 C), 29.78, 30.67, 36.67, 38.27, 63.14.

Example 52: (S)-4-Ethylheptan-1-ol ((S)-22)

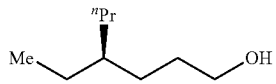

The title compound was prepared according to Representative Procedure M except (S)-20a and MeMgCl were used instead of (R)-17 and EtMgCl. Yield: 73%. $[\alpha]_D^{23}$=+0.7° (c 0.6, CH$_2$Cl$_2$). $^1$H NMR (300 MHz, CDCl$_3$): δ 0.80-0.90 (m, 6H), 1.18-1.36 (m, 9H), 1.48-1.66 (m, 3H), 3.61 (t, J=6.9 Hz, 2H); $^{13}$C NMR (75 MHz, CDCl$_3$) δ 10.77, 14.47, 19.76, 25.77, 29.00, 29.92, 35.44, 38.39, 63.50. The optical purity of ≥99% ee was determined by Chiral GC analysis, CP-Chirasil-Dex CB capillary column (25 m×0.25 mm, 0.39 μM film). Test conditions: carrier gas 6 psi H$_2$, oven program (45° C. for 2 min, then 0.3° C./min to 65° C. for 0 min, then 0.1° C./min to 80° C. for 50 min, then 30° C./min to 200° C. for 3 min), detector FID 200° C. Retention times (min): $t_R$ 207 (minor), $t_S$ 203 (major).

Example 53: (S)-6-Methyl-4-propylheptan-1-ol ((S)-24)

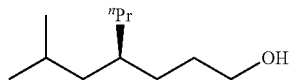

The title compound was prepared according to Representative Procedure M except (S)-20a and $^i$PrMgCl were used instead of (R)-17 and EtMgCl. Yield: 70%. $[\alpha]_D^{23}$ is too small to be determined. $^1$H NMR (300 MHz, CDCl$_3$): δ 0.82-0.92 (m, 9H), 1.04-1.70 (m, 13H), 3.61 (t, J=6.6 Hz, 2H); $^{13}$C NMR (101 MHz, CDCl$_3$) δ 14.48, 19.53, 22.92 (2 C), 25.25, 29.66 (2 C), 34.48, 36.14, 43.69, 63.55. The optical purity of ≥99% ee was determined by Chiral GC analysis, CP-Chirasil-Dex CB capillary column (25 m×0.25 mm, 0.39 μM film). Test conditions: carrier gas 6 psi H$_2$, oven program (35° C. for 2 min, then 0.2° C./min to 60° C. for 840 min, then 30° C./min to 200° C. for 3 min), detector FID 200° C. Retention times (min): $t_R$ 793 (minor); $t_S$ 804 (major). The optical purity of ≥99% ee was also determined by $^1$H NMR analysis of Mosher esters.

Example 54: (S)-4-(Cyclohexylmethyl)heptan-1-ol ((S)-27)

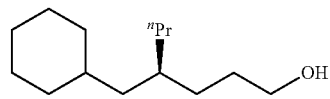

The title compound was prepared according to Representative Procedure M except (S)-20a and CyMgCl were used instead of (R)-17 and EtMgCl. Yield: 71%. $[\alpha]_D^{23}$=−0.28° (c 1.58, CH$_2$Cl$_2$). $^1$H NMR (300 MHz, CDCl$_3$): δ 0.87 (t, J=6.0 Hz, 3H), 1.00-1.75 (m, 22H), 3.61 (t, J=6.0 Hz, 2H); $^{13}$C NMR (101 MHz, CDCl$_3$) δ 14.39, 19.49, 26.33, 26.66, 29.64, 29.72, 33.65, 33.71, 34.86, 36.19, 42.08, 63.45. The optical purity of ≥99% ee was determined by $^1$H NMR analysis of Mosher esters.

Example 55: (R)-7-(1,3-Dioxan-2-yl)-4-propylheptan-1-ol ((R)-28). Representative Procedure O

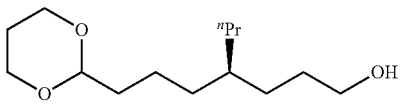

To a solution of (S)-tert-butyl((4-(iodomethyl)heptyl)oxy)dimethylsilane 20b (92 mg, 0.25 mmol), CuCl$_2$ (1.7 mg, 0.0125 mmol), 1-phenyl-1-propyne (4.7 µL, 0.0375 mmol), 1-methyl-2-pyrrolidinone (96 µL, 0.10 mmol) in THF (1.5 mL) was slowly added (2-(1,3-dioxan-2-yl)ethyl)magnesium bromide (0.5 M in THF, 1.0 mL, 0.50 mmol) at 0° C. The resultant solution was stirred at 0° C. for 2 h. The reaction mixture was then quenched with aqueous NH$_4$Cl, extracted with EtOAc, washed by brine, dried with MgSO$_4$, and concentrated. The residue was dissolved in THF (0.5 mL), and TBAF (1 M in THF, 0.5 mL, 0.5 mmol) was added at 0° C., and the resulting solution was stirred for 3 h at 23° C. The reaction mixture was then quenched with brine, extracted with EtOAc, dried with MgSO$_4$, concentrated, and purified by column chromatography (silica gel, 20% ethyl acetate in hexanes) to afford the title product (43 mg, 71% yield). $[\alpha]_D^{23}$=-0.56° (c 1.2, CH$_2$Cl$_2$). $^1$H NMR (300 MHz, CDCl$_3$): δ 0.85 (t, J=6.0 Hz, 3H), 1.14-1.40 (m, 12H), 1.42-1.75 (m, 5H), 1.95-2.15 (m, 1H), 3.58 (t, J=7.5 Hz, 2H), 3.74 (m, 2H), 4.08 (m, 2H), 4.49 (t, J=6.0 Hz, 1H); $^{13}$C NMR (75 MHz, CDCl$_3$) δ 14.35, 19.63, 20.91, 25.73, 29.30, 29.58, 29.78, 33.31, 35.51, 35.75, 36.82, 63.30, 66.78, 102.31. The optical purity of ≥99% ee was determined by $^1$H NMR analysis of 2-methoxy-2-(1-naphthyl)propionic acid ester.

Example 56: (R)-6-((tert-Butyldimethylsilyl)oxy)-2-propylhexyl 4-methylbenzenesulfonate ((R)-29a)

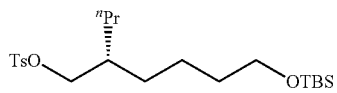

The title compound was prepared according to Representative Procedure K except (R)-15c was used instead of (R)-15a. Yield: 99%. $[\alpha]_D^{23}$=-0.52° (c 1.15, CH$_2$Cl$_2$). $^1$H NMR (400 MHz, CDCl$_3$) δ 0.03 (s, 6H), 0.81 (t, J=6.9 Hz, 3H), 0.88 (s, 9H), 1.15-1.30 (m, 8H), 1.35-1.47 (m, 2H), 1.60 (m, 1H), 2.43 (s, 3H), 3.54 (t, J=6.4 Hz, 2H), 3.90 (d, J=5.3 Hz, 2H), 7.33 (d, J=8.3 Hz, 2H), 7.77 (d, J=8.3 Hz, 2H); $^{13}$C NMR (101 MHz, CDCl$_3$) δ -5.50 (2 C), 13.97, 18.08, 19.38, 21.36, 22.48, 25.75 (3 C), 30.15, 32.56, 32.68, 37.16, 62.63, 72.55, 127.66 (2 C), 129.58 (2 C), 132.95, 144.39.

Example 57: (R)-tert-Butyl((5-(iodomethyl)octyl)oxy)dimethylsilane ((R)-29b)

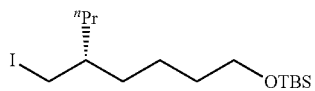

The title compound was prepared according to Representative Procedure N except (R)-15c was used instead of (R)-15b. Yield: 88%. %. $[\alpha]_D^{23}$=-7.1° (c 10.5, CH$_2$Cl$_2$). $^1$H NMR (400 MHz, CDCl$_3$) δ 0.04 (s, 6H), 0.82-0.95 (m, 12H), 1.09-1.19 (m, 1H), 1.19-1.40 (m, 8H), 1.43-1.56 (m, 2H), 3.24 (d, J=4.5 Hz, 2H), 3.59 (t, J=6.4 Hz, 2H); $^{13}$C NMR (101 MHz, CDCl$_3$) δ -5.28 (2 C), 14.13, 16.21, 18.25, 19.60, 22.65, 25.93 (3 C), 32.79, 34.09, 36.57, 38.30, 62.87.

Example 58: (R)-5-Methyloctan-1-ol ((R)-30)

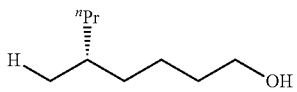

The title compound was prepared according to Representative Procedure L except (R)-29a was used instead of (R)-17. Yield: 76%. $[\alpha]_D^{23}$=-0.65° (c 0.9, CH$_2$Cl$_2$). $^1$H NMR (300 MHz, CDCl$_3$): δ 0.84 (d, J=6 Hz, 3H), 0.87 (t, J=6 Hz, 3H), 1.00-1.18 (m, 2H), 1.20-1.45 (m, 7H), 1.48-1.65 (m, 3H), 3.64 (t, J=7.5 Hz, 2H); $^{13}$C NMR (75 MHz, CDCl$_3$) δ 14.27, 19.47, 20.01, 23.10, 32.35, 33.03, 36.71, 39.21, 62.98. The optical purity of ≥99% ee was determined by $^1$H NMR analysis of Mosher esters.

Example 59: (R)-5-Ethyloctan-1-ol ((R)-31)

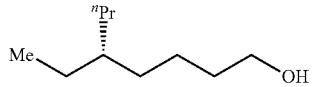

The title compound was prepared according to Representative Procedure M except (R)-29a and MeMgCl were used instead of (R)-17 and EtMgCl. Yield: 73%. $[\alpha]_D^{23}$=+0.4° (c 1.2, CH$_2$Cl$_2$). $^1$H NMR (300 MHz, CDCl$_3$): δ 0.82 (t, J=6 Hz, 3H), 0.87 (t, J=6 Hz, 3H), 1.10-1.40 (m, 11H), 1.45-1.60 (m, 2H), 3.63 (t, J=6 Hz, 2H); $^{13}$C NMR (75 MHz, CDCl$_3$) δ 10.72, 14.40, 19.73, 22.78, 25.70, 32.88, 33.16, 35.43, 38.50, 62.99. The optical purity of ≥99% ee was determined by $^1$H NMR analysis of 2-methoxy-2-(1-naphthyl)propionic acid esters.

Example 60: (S)-5-Propylnonan-1-ol ((S)-32)

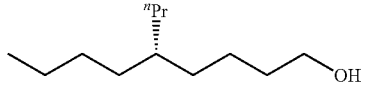

The title compound was prepared according to Representative Procedure M except (R)-29a and $^n$PrMgCl were used instead of (R)-17 and EtMgCl. Yield: 67%. $[\alpha]_D^{23}$=+0.10° (c 1.53, CH$_2$Cl$_2$). $^1$H NMR (400 MHz, CDCl$_3$) δ 0.78-0.94 (m, 6H), 1.10-1.40 (m, 14H), 1.43-1.63 (m, 3H), 3.63 (t, J=6.6 Hz, 2H); $^{13}$C NMR (101 MHz, CDCl$_3$) δ 14.13, 14.50, 19.79, 22.85, 23.13, 28.91, 33.27 (2 C), 33.49, 36.00, 37.13, 63.07. HRMS calcd for C$_6$H$_{11}$IO$_2$ [M+H]$^+$: 242.9882. found 242.9884. The optical purity of ≥99% ee was determined by $^1$H NMR analysis of 2-methoxy-2-(1-naphthyl)propionic acid esters.

Example 61: (R)-7-Methyl-5-propyloctan-1-ol ((R)-33)

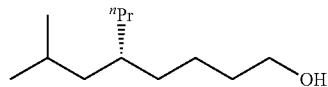

The title compound was prepared according to Representative Procedure M except (R)-29a and $^i$PrMgCl were used instead of (R)-17 and EtMgCl. Yield: 72%. $[\alpha]_D^{23}$ is too small to be determined. $^1$H NMR (400 MHz, CDCl$_3$) δ 0.80-0.95 (m, 9H), 1.06 (t, J=6.9 Hz, 2H), 1.13-1.44 (m, 9H), 1.46-1.72 (m, 3H), 3.64 (t, J=6.6 Hz, 2H); $^{13}$C NMR (101 MHz, CDCl$_3$) δ14.51, 19.57, 22.65, 22.94, 22.97, 25.28, 33.30, 33.71, 34.70, 36.19, 43.77, 63.10. The optical purity of ≥99% ee was determined by $^1$H NMR analysis of 2-methoxy-2-(1-naphthyl)propionic acid esters.

Example 62: (R)-7,7-Dimethyl-5-propyloctan-1-ol ((R)-34)

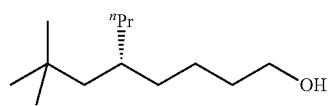

The title compound was prepared according to Representative Procedure M except (R)-29a and $^t$BuMgCl were used instead of (R)-17 and EtMgCl. Yield: 89%. The optical purity of ≥99% ee was determined by Chiral GC analysis, CP-Chirasil-Dex CB capillary column (25 m×0.25 mm, 0.39 μM film). Test conditions: carrier gas 8 psi H$_2$, oven program (80° C. for 2 min, then 0.5° C./min to 110° C. for 24 min, then 30° C./min to 200° C. for 1 min), detector FID 200° C. Retention times (min): $t_R$ 62.27 (major); $t_S$ 62.91 (minor). $[\alpha]_D^{23}$=+1.15° (c 1.62, CH$_2$Cl$_2$). $^1$H NMR (400 MHz, CDCl$_3$) δ 0.85-0.89 (m, 12H), 1.10 (d, J=4.2 Hz, 2H), 1.15-1.38 (m, 9H), 1.38-1.61 (m, 3H), 3.63 (t, J=6.7 Hz, 2H); $^{13}$C NMR (101 MHz, CDCl$_3$) δ 14.52, 19.90, 22.93, 29.96 (3 C), 31.11, 33.28, 33.67, 35.89, 38.40, 48.44, 63.07.

Example 63: (R)-5-(Cyclohexylmethyl)octan-1-ol ((R)-35)

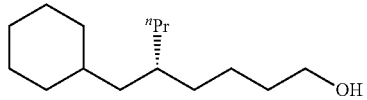

The title compound was prepared according to Representative Procedure M except (R)-29a and CyMgCl were used instead of (R)-17 and EtMgCl. Yield: 86%. $[\alpha]_D^{23}$=+0.57° (c 2.40, CH$_2$Cl$_2$). $^1$H NMR (400 MHz, CDCl$_3$) δ 0.74-0.95 (m, 5H), 0.97-1.44 (m, 15H), 1.46-1.77 (m, 8H), 3.63 (t, J=6.6 Hz, 2H); $^{13}$C NMR (101 MHz, CDCl$_3$) δ 14.51, 19.61, 22.68 (2 C), 26.43, 26.76, 33.28, 33.81 (3 C), 33.91, 34.98, 36.29, 42.21, 63.05. The optical purity of ≥99% ee was determined by $^1$H NMR analysis of 2-methoxy-2-(1-naphthyl)propionic acid esters.

Example 64: (R)-8-(1,3-Dioxan-2-yl)-5-propyloctan-1-ol ((R)-36)

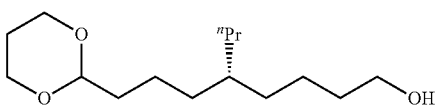

The title compound was prepared according to Representative Procedure O except (R)-29b was used instead of (S)-20b. Yield: 73%. $[\alpha]_D^{23}$=+0.63° (c 2.23, CH$_2$Cl$_2$). $^1$H NMR (400 MHz, CDCl$_3$) δ 0.86 (t, J=6.9 Hz, 3H), 1.14-1.42 (m, 14H), 1.48-1.64 (m, 4H), 1.96-2.16 (m, 1H), 3.64 (t, J=6.6 Hz, 2H), 3.70-3.81 (m, 2H), 4.05-4.15 (m, 2H), 4.51 (t, J=5.2 Hz, 1H); $^{13}$C NMR (101 MHz, CDCl$_3$) δ 14.43, 19.74, 21.00, 22.76, 25.80, 33.18, 33.30, 33.39, 35.61, 35.86, 37.08, 62.92, 66.85 (2 C), 102.40. The optical purity of ≥99% ee was determined by $^1$H NMR analysis of 2-methoxy-2-(1-naphthyl)propionic acid esters.

Summary of Feeble Chirality III

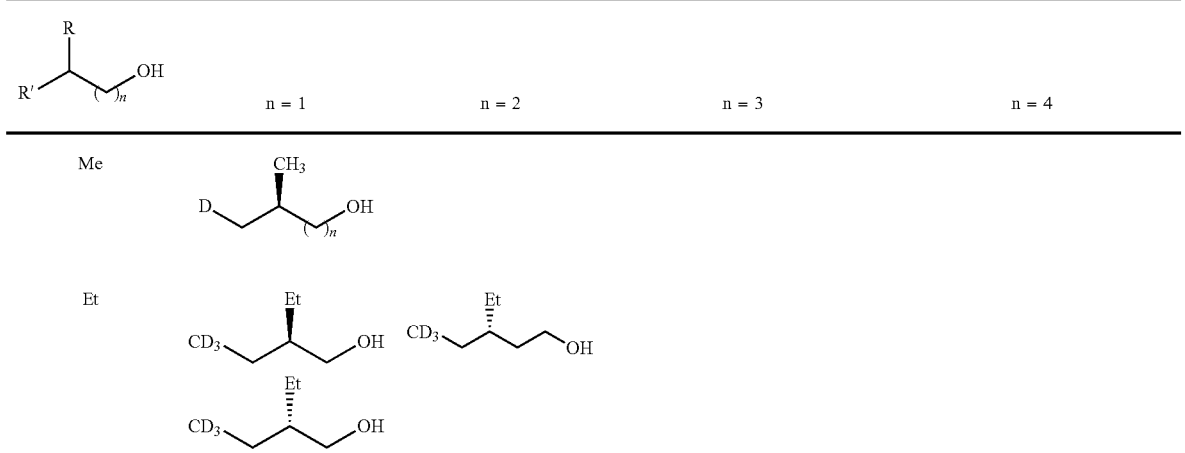

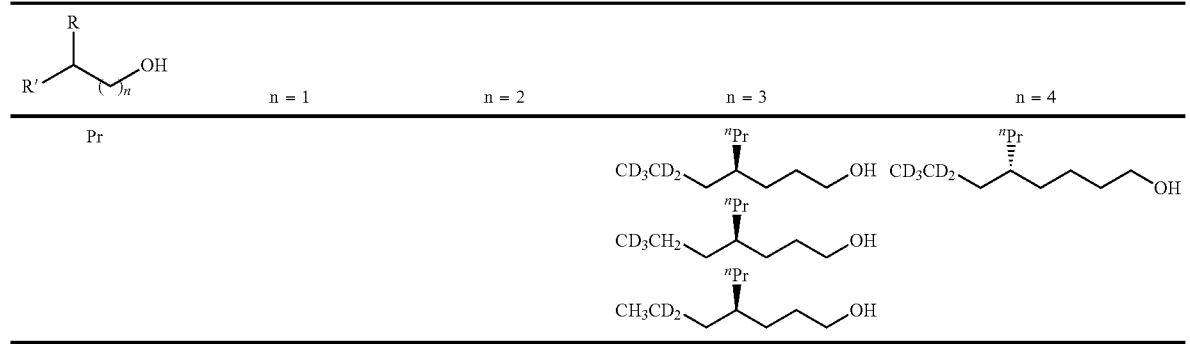

n=1 (Me)

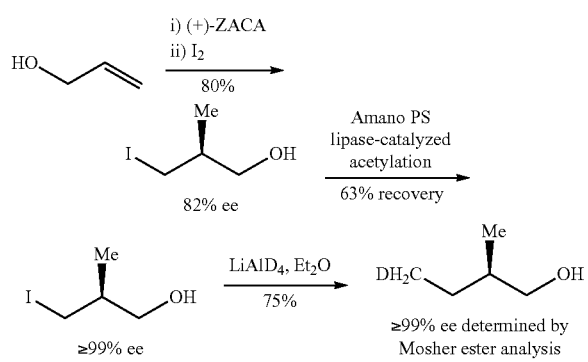

Example 65: (R)-2-methylpropan-3-$d_1$-1-ol

To a solution of (S)-3-iodo-2-methyl-1-propanol (200 mg, 1 mmol, ≥99% ee) in Et$_2$O (2 mL) was added LiAlD$_4$ (64 mg, 1.5 mmol) at 0° C., and the resultant solution was stirred for 2 h at 0° C., and additional 30 min at 23° C. The reaction was quenched with sat. Na$_2$SO$_4$ (3 drops) at 0° C., diluted with pentane, dried over Na$_2$SO$_4$, filtered. The filtrate was concentrated carefully at 0° C. to give the title product (56 mg, 75%) as a colorless oil. The optical purity was determined by Mosher ester analysis, ≥99% ee. In the analysis of $^1$H NMR, benzene-$d_6$ was used as a deuterated solvent. $^1$H NMR (300 MHz, CDCl$_3$): δ 0.88-0.94 (m, 5H), 1.36 (s, 1H), 1.70-1.82 (m, 1H), 3.41 (t, J=5.7, 2 H); $^{13}$C NMR (75 MHz, CDCl$_3$): δ 18.5, 18.9, 30.8, 69.7.

n=1 (Et)

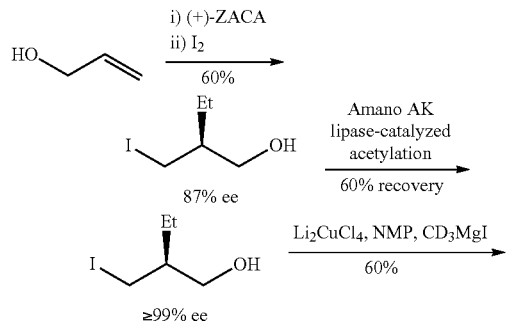

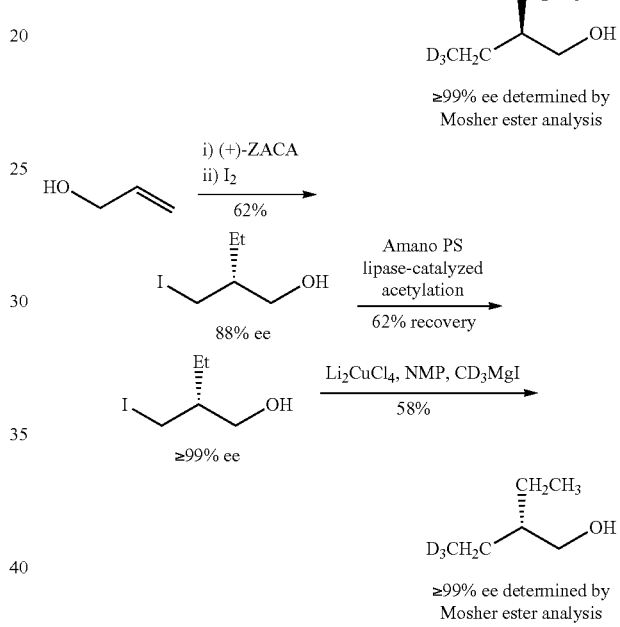

Example 66: (R)-2-ethylbutan-4,4,4-$d_3$-1-ol

To a solution of (S)-2-(iodomethyl)pentan-1-ol (64 mg, 0.3 mmol, ≥99% ee) in THF (1.5 mL) were added Li$_2$CuCl$_4$ (0.1 M in THF, 0.15 mL, 0.015 mmol), 1-methyl-2-pyrrolidinone (172 μL, 0.18 mmol) and CD$_3$MgI (1 M in ether, 0.99 mL, 0.99 mmol) at 0° C., and the resulting solution was stirred for 1 h at 0° C., and additional 2 h at 23° C. The reaction mixture was then quenched with aqueous NH$_4$Cl, extracted with Et$_2$O, washed by brine, dried with MgSO$_4$, concentrated and purified by column chromatography (silica gel, 20% Et$_2$O in pentane) to afford the title product (19 mg, 60%). The optical purity of ≥99% ee was determined by $^1$H NMR analysis of Mosher esters. In the analysis of $^1$H NMR, benzen-$d_6$ was used as a deuterated solvent. $^1$H NMR (300 MHz, CDCl$_3$) δ 0.89 (t, J=6.9 Hz, 3H), 1.20-1.42 (m, 6H), 3.55 (d, J=2.7 Hz, 2H); $^{13}$C NMR (75 MHz, CDCl$_3$) δ 10.4, 11.1, 22.6, 22.9, 43.4, 65.0.

n=2 (Et)

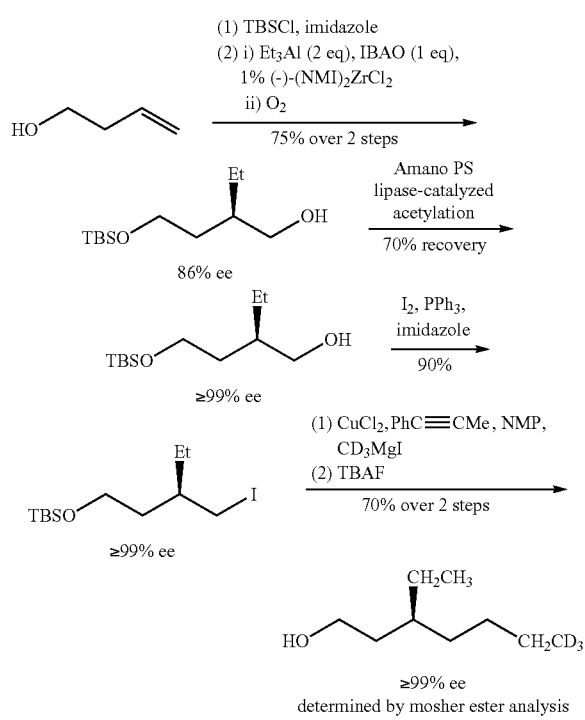

Example 67: (R)-tert-butyl((3-(iodomethyl)pentyl)oxy)dimethylsilane

To a solution of 89 mg (1.3 mmol) of imidazole and 288 mg (1.1 mmol) of PPh$_3$ in CH$_2$Cl$_2$ (2 mL) was added 279 mg (1.1 mmol) of I$_2$ at 0° C. After stirring for 15 min at 0° C., (R)-4-((tert-butyldimethylsilyl)oxy)-2-ethylbutan-1-ol (232 mg, 1.0 mmol, ≥99% ee) in CH$_2$Cl$_2$ (1 mL) was added to above solution. The mixture was stirred for 4 h at 23° C. The reaction mixture was then quenched with aqueous Na$_2$S$_2$O$_3$ and water, extracted with EtOAc, washed by brine, dried over MgSO$_4$, concentrated and purified by column chromatography (silica gel, 99/1 hexanes-EtOAc) to afford the title product (308 mg, 90% yield). $[\alpha]_D^{23}$=−10.1° (c 5, CH$_2$Cl$_2$). $^1$H NMR (300 MHz, CDCl$_3$) δ 0.05 (s, 6H), 0.85-0.91 (s, 12H), 1.24-1.57 (m, 5H), 3.26-3.37 (m, 2H), 3.64 (t, J=6.6 Hz, 2H); $^{13}$C NMR (75 MHz, CDCl$_3$) δ −5.19 (2 C), 10.93, 16.20, 18.33, 26.01 (3 C), 27.26, 37.00, 37.06, 60.60.

Example 68: (R)-2-ethylbutan-4,4,4-d$_3$-1-ol

To a solution of (R)-tert-butyl((3-(iodomethyl)pentyl)oxy)dimethylsilane (102 mg, 0.3 mmol, ≥99% ee), CuCl$_2$ (2 mg, 0.015 mmol), 1-phenyl-1-propyne (5.9 µL, 0.045 mmol), 1-methyl-2-pyrrolidinone (172 µL, 0.18 mmol) in THF (2 mL) was slowly added CD$_3$MgI (1 M in ether, 1.2 mL, 1.2 mmol) at 0° C. The resulting solution was stirred at 0° C. for 1 h, and additional 3 h at 23° C. The reaction mixture was then quenched with aqueous NH$_4$Cl, extracted with Et$_2$O, washed by brine, dried with MgSO$_4$, and concentrated. The residue was dissolved in THF (1 mL), and TBAF (1 M in THF, 0.6 mL, 0.6 mmol) was added at 0° C., and the resulting solution was stirred for 3 h at 23° C. The reaction mixture was then quenched with ice water, extracted with Et$_2$O, washed by brine, dried with MgSO$_4$, concentrated, and purified by column chromatography (silica gel, 20% ethyl acetate in hexanes) to afford the title product (22 mg, 70%). The optical purity of ≥99% ee was determined by $^1$H NMR analysis of Mosher esters. In the analysis of $^1$H NMR, acetonitrile-d$_3$ was used as a deuterated solvent. $^1$H NMR (300 MHz, CDCl$_3$) δ 0.85 (t, J=6.6 Hz, 3H), 1.24-1.38 (m, 6H), 1.48-1.56 (m, 2H), 3.66 (t, J=6.9 Hz, 2H); $^{13}$C NMR (75 MHz, CDCl$_3$) δ 10.01, 10.86, 25.32, 25.60, 36.17, 37.08, 61.34.

n=3 (Pr)

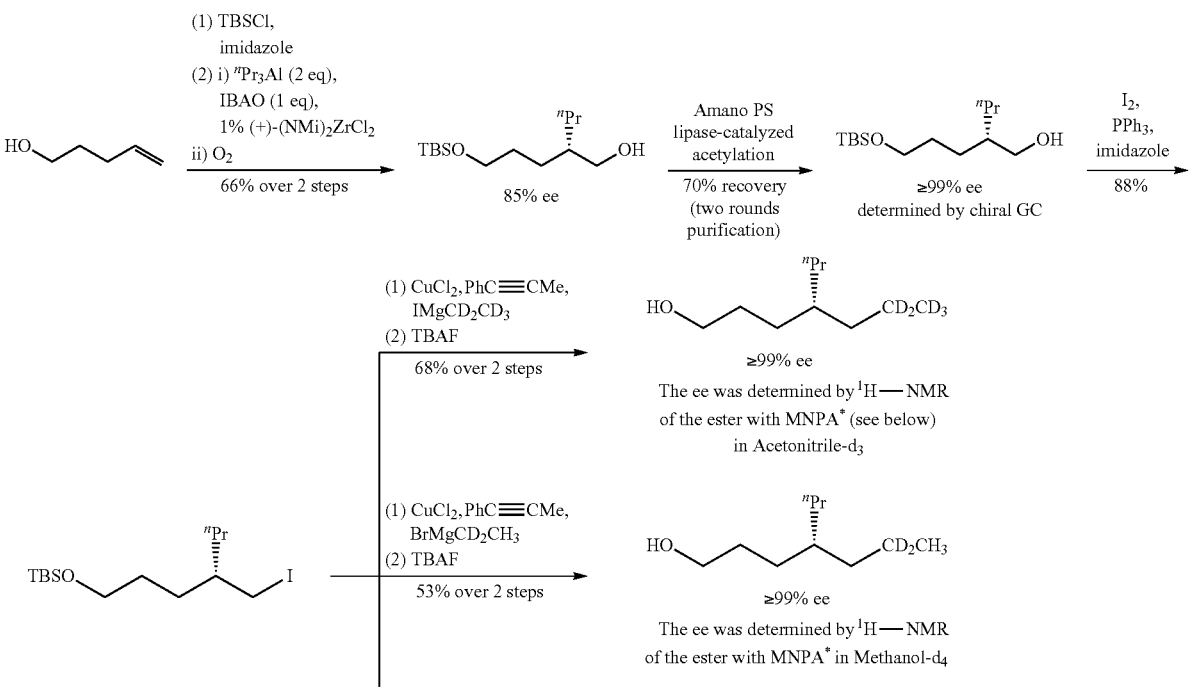

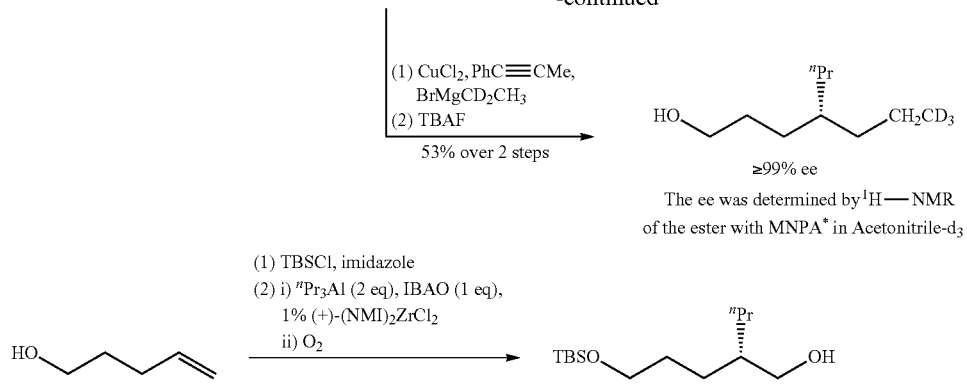

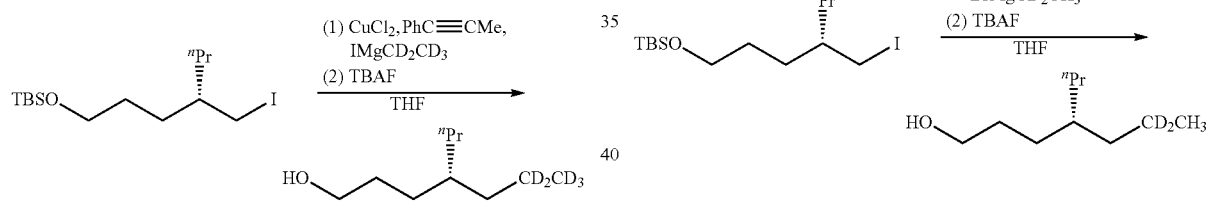

Example 69: tert-Butyldimethyl(pent-4-en-1-yloxy)silane

To a stirred solution of 4-penten-1-ol (11.4 mL, 110 mmol) in DMF (200 mL) were added imidazole (18.7 g, 275 mmol), and TBSCl (24.9 g, 165 mmol) at 0° C. The resultant mixture was stirred for 8 h at 23° C. The reaction mixture was then quenched with $H_2O$ and extracted with ethyl acetate three times, washed by $H_2O$ and Brine, dried with $MgSO_4$, concentrated, and purified by column chromatography (silica gel, hexanes) to afford the title product (21.6 g, 98% yield). $^1$H NMR (300 MHz, $CDCl_3$) δ 0.05 (s, 6H), 0.90 (s, 9H), 1.61 (m, 2H), 2.11 (m, 2H), 3.62 (t, J=6.0 Hz, 2H), 5.00 (m, 2H), 5.83 (m, 1H).

Example 70: (R)-4-Propylheptan-6,6,7,7,7-d$_5$-1-ol

To a stirred mixture of magnesium turnings (146 mg, 6.0 mmol) in dry diethyl ether (2.5 mL) was added dropwise iodoethane-d$_5$ (805 mg, 5.0 mmol) in dry diethyl ether (2.5 mL). The solution of iodoethane-d$_5$ was added at a rate that maintained moderate boiling of the solvent. After 2 hr refluxing the resulting 1 M solution of (ethyl-d$_5$)magnesium iodide was used directly.

To a solution of (S)-tert-butyl((4-(iodomethyl)heptyl)oxy)dimethylsilane (82 mg, 0.22 mmol), $CuCl_2$ (1.5 mg, 0.011 mmol), 1-phenyl-1-propyne (4.2 μL, 0.033 mmol), 1-Methyl-2-pyrrolidinone (170 μL, 1.8 mmol) in THF (1.5 mL) was slowly added 1 M solution of (ethyl-d$_5$)magnesium iodide (0.73 mL, 0.73 mmol) at −10° C., and the resultant solution was stirred for 2 h at 23° C. The reaction mixture was then quenched with aqueous saturated $NH_4Cl$ solution, extracted with ethyl ether, washed with Brine, dried over anhydrous $Na_2SO_4$, and concentrated. The residue was dissolved in THF (0.5 mL), and TBAF (1 M in THF, 0.33 mL, 0.33 mmol) was added at 23° C., and the resulting solution was stirred for 4 h. The reaction mixture was then quenched with $H_2O$, extracted with $Et_2O$, washed with Brine, dried over anhydrous $Na_2SO_4$, concentrated, and purified by column chromatography (silica gel, 0 to 15% gradient ethyl acetate in hexanes) to afford the title product (25 mg, 68%). $^1$H NMR (300 MHz, $CDCl_3$): δ 0.87 (t, J=7.5 Hz, 3H), 1.15-1.40 (m, 9H), 1.48-1.60 (m, 2H), 3.62 (t, J=6.0 Hz, 2H); $^{13}$C NMR (101 MHz, $CDCl_3$) δ 13.26, 14.39, 18.60, 19.66, 29.42, 29.83 35.59, 35.88, 36.63, 63.47. The optical purity of ≥99% ee was determined by $^1$H NMR analysis of the ester which was prepared by treating title product with α-Methoxy-α-methyl-1-naphthaleneacetic Acid (MNPA). In the analysis of $^1$H-NMR, acetonitrile-d$_3$ was used as a deuterated solvent.

Example 71: (R)-4-propylheptan-6,6-d$_2$-1-ol

To stirred mixture of magnesium turnings (146 mg, 6.0 mmol) in dry diethyl ether (2.5 mL) was added dropwise bromoethane-1,1-d$_2$ (555 mg, 5.0 mmol) in dry diethyl ether (2.5 mL). The solution of bromoethane-1,1-d$_2$ was added at a rate that maintained moderate boiling of the solvent. After 2 hr refluxing the resulting 1 M solution of (ethyl-1,1-d$_2$) magnesium was used directly.

To a solution of (S)-tert-butyl((4-(iodomethyl)heptyl)oxy) dimethylsilane (85 mg, 0.23 mmol), $CuCl_2$ (1.5 mg, 0.012 mmol), 1-phenyl-1-propyne (4.3 μL, 0.035 mmol), 1-Methyl-2-pyrrolidinone (177 μL, 1.8 mmol) in THF (1.5 mL) was slowly added 1 M solution of (ethyl-1,1-d$_2$) magnesium bromide (0.76 mL, 0.76 mmol) at 0° C., and the resultant solution was stirred for 2 h at 0° C. The reaction mixture was then quenched with aqueous saturated $NH_4Cl$ solution, extracted with ethyl ether, washed with Brine, dried over anhydrous $Na_2SO_4$, and concentrated. The residue was dissolved in THF (0.5 mL), and TBAF (1 M in THF, 0.35 mL, 0.35 mmol) was added at 23° C., and the resulting solution was stirred for 4 h. The reaction mixture was then quenched with $H_2O$, extracted with $Et_2O$, washed with Brine, dried over anhydrous $Na_2SO_4$, concentrated, and purified by column chromatography (silica gel, 0 to 15% gradient ethyl acetate in hexanes) to afford the title product (20 mg, 53%). ¹H NMR (300 MHz, CDCl₃): δ 0.88 (t, J=7.5 Hz, 3H), 0.86 (s, 3H), 1.15-1.40 (m, 9H), 1.48-1.60 (m, 2H), 3.62 (t, J=7.5 Hz, 2H); ¹³C NMR (75 MHz, CDCl₃) δ 14.39, 14.61, 19.09, 19.87, 29.62, 30.03, 35.86, 36.07, 36.80, 63.61. The optical purity of ≥99% ee was determined by ¹H-NMR analysis of the ester which was prepared by treating title product with α-Methoxy-α-methyl-1-naphthaleneacetic Acid (MNPA). In the analysis of ¹H-NMR, methanol-d₄ was used as a deuterated solvent.

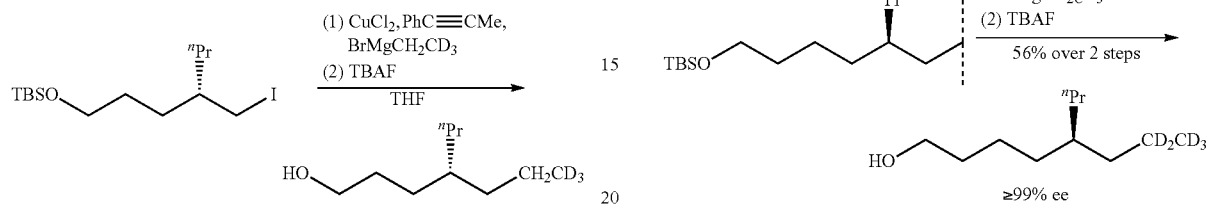

Example 72: (R)-4-propylheptan-7,7,7-d₃-1-ol

To a stirred mixture of magnesium turnings (146 mg, 6.0 mmol) in dry diethyl ether (2.5 mL) was added dropwise bromoethane-2,2,2-d₃ (560 mg, 5.0 mmol) in dry diethyl ether (2.5 mL). The solution of bromoethane-2,2,2-d₃ was added at a rate that maintained moderate boiling of the solvent. After 2 hr refluxing the resulting 1 M solution of (ethyl-2,2,2-d₃)magnesium was used directly.

To a solution of (S)-tert-butyl((4-(iodomethyl)heptyl)oxy) dimethylsilane (85 mg, 0.23 mmol), CuCl₂ (1.5 mg, 0.012 mmol), 1-phenyl-1-propyne (4.3 µL, 0.035 mmol), 1-Methyl-2-pyrrolidinone (177 µL, 1.8 mmol) in THF (1.5 mL) was slowly added 1 M solution of (ethyl-2,2,2-d₃) magnesium bromide (0.76 mL, 0.76 mmol) at 0° C., and the resultant solution was stirred for 2 h at 0° C. The reaction mixture was then quenched with aqueous saturated NH₄Cl solution, extracted with ethyl ether, washed with Brine, dried over anhydrous Na₂SO₄, and concentrated. The residue was dissolved in THF (0.5 mL), and TBAF (1 M in THF, 0.35 mL, 0.35 mmol) was added at 23° C., and the resulting solution was stirred for 4 h. The reaction mixture was then quenched with H₂O, extracted with Et₂O, washed with Brine, dried over anhydrous Na₂SO₄, concentrated, and purified by column chromatography (silica gel, 0 to 15% gradient ethyl acetate in hexanes) to afford the title product (20 mg, 53%). ¹H NMR (300 MHz, CDCl₃): δ 0.87 (t, J=7.5 Hz, 3H), 1.15-1.40 (m, 11H), 1.48-1.60 (m, 2H), 3.62 (t, J=6.0 Hz, 2H); ¹³C NMR (101 MHz, CDCl₃) δ 13.48, 14.38, 19.38, 19.65, 29.40, 29.82, 35.78, 35.87, 36.65, 63.47. The optical purity of ≥99% ee was determined by ¹H-NMR analysis of the ester which was prepared by treating title product with α-Methoxy-α-methyl-1-naphthaleneacetic Acid (MNPA). In the analysis of ¹H-NMR, acetonitrile-d₃ was used as a deuterated solvent.
n=4 (Pr)

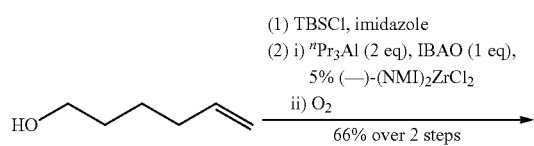

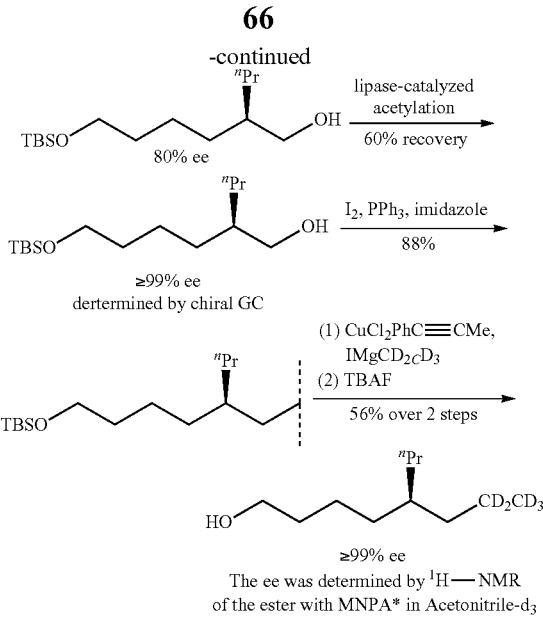

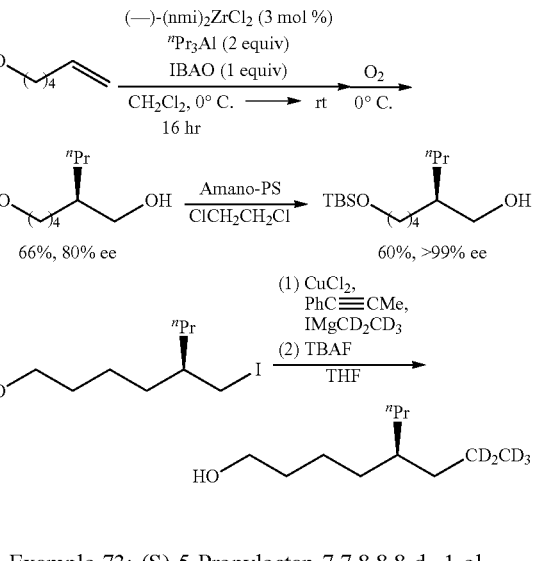

Example 73: (S)-5-Propyloctan-7,7,8,8,8-d₅-1-ol

To a stirred mixture of magnesium turnings (146 mg, 6.0 mmol) in dry diethyl ether (2.5 mL) was added dropwise iodoethane-d₅ (805 mg, 5.0 mmol) in dry diethyl ether (2.5 mL). The solution of iodoethane-d₅ was added at a rate that maintained moderate boiling of the solvent. After 2 hr refluxing the resulting 1 M solution of (ethyl-d₅)magnesium iodide was used directly.

To a solution of (R)-tert-butyl((5-(iodomethyl)octyl)oxy) dimethylsilane (96 mg, 0.25 mmol), CuCl₂ (1.7 mg, 0.013 mmol), 1-phenyl-1-propyne (4.7 µL, 0.038 mmol), 1-Methyl-2-pyrrolidinone (193 µL, 2.0 mmol) in THF (1.5 mL) was slowly added 1 M solution of (ethyl-d₅)magnesium iodide (0.83 mL, 0.83 mmol) at 0° C., and the resultant solution was stirred for 2 h at 0° C. The reaction mixture was then quenched with aqueous saturated NH₄Cl solution, extracted with ethyl ether, washed with Brine, dried over anhydrous Na₂SO₄, and concentrated. The residue was dissolved in THF (0.5 mL), and TBAF (1 M in THF, 0.38 mL, 0.38 mmol) was added at 23° C., and the resulting solution was stirred for 4 h. The reaction mixture was then quenched with H₂O, extracted with Et₂O, washed with Brine, dried over anhydrous Na₂SO₄, concentrated, and purified by column chromatography (silica gel, 0 to 15% gradient ethyl acetate in hexanes) to afford the title product (25 mg, 56%). $^1$H NMR (300 MHz, CDCl$_3$): δ 0.87 (t, J=6.0 Hz, 3H), 1.15-1.40 (m, 11H), 1.48-1.60 (m, 2H), 3.64 (t, J=7.5 Hz, 2H); $^{13}$C NMR (101 MHz, CDCl$_3$) δ 13.29, 14.41, 18.64, 19.69, 22.75, 33.19, 33.39, 35.62, 35.92, 36.82, 63.03. The optical purity of ≥99% ee was determined by $^1$H-NMR analysis of the ester which was prepared by treating title product with α-Methoxy-α-methyl-1-naphthaleneacetic Acid (MNPA). In the analysis of $^1$H-NMR, acetonitrile-d$_3$ was used as a deuterated solvent.

Example 74: Representative Procedure for the Synthesis of MNPA Esters

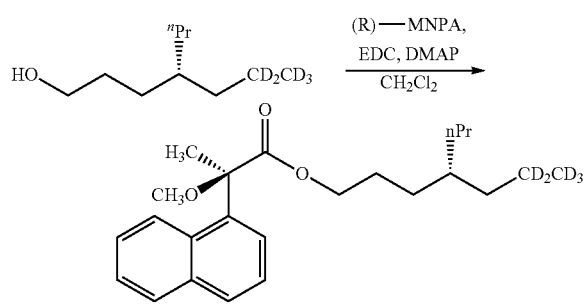

To the solution of (R)-4-propylheptan-6,6,7,7,7-d$_5$-1-ol (3.0 mg, 0.018 mmol) in CH$_2$Cl$_2$ (0.5 mL) was added (R)-MNPA (8.5 mg, 0.037 mmol), N-(3-Dimethylaminopropyl)-N-ethylcarbodiimide hydrochloride (11 mg, 0.055 mmol), and 4-(dimethylamino) pyridine (6.8 mg, 0.055 mmol). The resultant solution was stirred for 24 h at 23° C. The reaction mixture was then quenched with water, washed with 1M HCl aq, aqueous saturated NaHCO$_3$ solution, and water, then dried over anhydrous MgSO$_4$, and concentrated. The residue was dissolved in acetonitrile-d$_3$ for the $^1$H NMR analysis.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A process of preparing a compound of formula I,

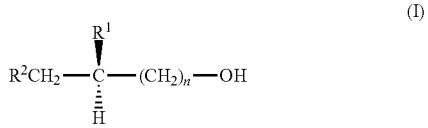
(I)

wherein
R$^1$ is alkyl, cycloalkyl-alkyl, cyclo(hetero)alkyl-alkyl, or aryl-alkyl;
R$^2$ is H, D, CD$_3$, CH$_2$CD$_3$, CD$_2$CH$_3$, CD$_2$CD$_3$, alkyl, cycloalkyl, cycloalkyl-alkyl, cyclo(hetero)alkyl-alkyl, aryl-alkyl, alkenyl, aryl, or heteroaryl, wherein each of alkyl, cycloalkyl, cycloalkyl-alkyl, cyclo(hetero)alkyl-alkyl, aryl-alkyl, alkenyl, aryl, and heteroaryl is optionally mono- or polysubstituted with substituents independently selected from halo, O-alkyl, cyano, amino, nitro, COOMe, and COOEt; and
n is an integer selected from 2-8
the process comprising treating a compound of formula (IV) having a high enantiomeric purity of ee≥99%:

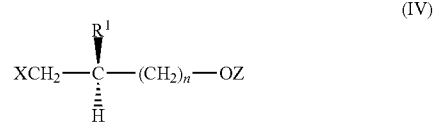
(IV)

wherein X is OR$_x$, R$_x$ is a protective group, and Z is H or a protective group; under a reduction condition or a cross-coupling condition to prepare said compound of formula (I), wherein said compound of formula (I) has a high enantiomeric purity (ee≥99%).

2. The process of claim 1, wherein said compound of formula (IV) is prepared by
(a) treating a compound of formula (III)

(III)

under a Zr-catalyzed asymmetric carboalumination condition to prepare intermediate (I);
(b) treating said intermediate (I) with a reagent to prepare said compound of formula (IV) having a low enantiomeric purity of ee<99%; and
(c) purifying the compound of formula (IV) having a low enantiomeric purity under a lipase-catalyzed acetylation reaction condition to prepare said compound of formula (IV) having a high enantiomeric purity of ee≥99%; wherein Z and n in formula (III) have the same meanings as in claim 1.

3. The process of claim 1, wherein said reduction condition comprises LiAlH$_4$.

4. The process of claim 1, wherein said cross-coupling condition is a Cu-, Ni-, or Pd-catalyzed cross-coupling reaction.

5. A process of preparing a compound of formula (I),

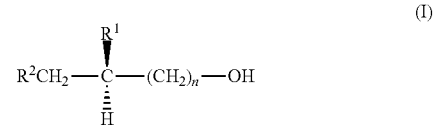
(I)

wherein
R$^1$ is alkyl, cycloalkyl-alkyl, cyclo(hetero)alkyl-alkyl, or aryl-alkyl;
R$^2$ is H, D, CD$_3$, CH$_2$CD$_3$, CD$_2$CH$_3$, CD$_2$CD$_3$, allyl, cycloalkyl, cycloalkyl-alkyl, cyclo(hetero)alkyl-alkyl, aryl-alkyl, alkenyl, aryl, or heteroaryl, wherein each of alkyl, cycloalkyl, cycloalkyl-alkyl, cyclo(hetero)alkyl-alkyl, aryl-alkyl, alkenyl, aryl, and heteroaryl is optionally mono- or polysubstituted with substituents independently selected from halo, O-alkyl, cyano, amino, nitro, COOMe, and COOEt; and
n is an integer selected from 2-8
the process comprising
(a) treating a compound of formula (III)

(III)

where n and Z have the same meanings as for formula (I); under a Zr-catalyzed asymmetric carboalumination condition to prepare intermediate (I);

(b) treating said intermediate (I) with a reagent to prepare said compound of formula (IV) having a low enantiomeric purity of ee<99%

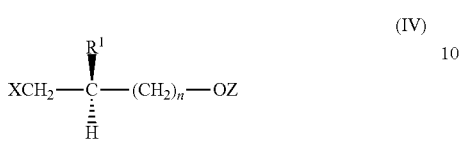

wherein X is $OR_x$ wherein $R_x$ is a protective group; and Z is H or a protective group and wherein n and Z have the same meanings as for formula (I);

(c) purifying the compound of formula (IV) having said low enantiomeric purity under a lipase-catalyzed acetylation reaction condition to prepare a compound of formula (IV) having an enantiomeric excess of 99% or above; and (d) treating said compound of formula (IV) having a high enantiomeric purity of ee≥99% under a reduction condition or a cross-coupling condition to prepare said compound of formula (I).

6. A process of preparing a compound of formula (II),

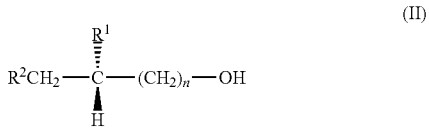

wherein $R^1$ is alkyl, cycloalkyl-alkyl, cyclo(hetero)alkyl-alkyl, or aryl-alkyl;

$R^2$ is H, D, $CD_3$, $CH_2CD_3$, $CD_2CH_3$, $CD_2CD_3$, alkyl, cycloalkyl, cycloalkyl-alkyl, cyclo(hetero)alkyl-alkyl, aryl-alkyl, alkenyl, aryl, or heteroaryl, wherein each of alkyl, cycloalkyl, cycloalkyl-alkyl, cyclo(hetero)alkyl-alkyl, aryl-alkyl, alkenyl, aryl, and heteroaryl is optionally mono- or polysubstituted with substituents independently selected from halo, O-alkyl, cyano, amino, nitro, COOMe, and COOEt; and n is an integer selected from 2-8;

the process comprising treating a compound of formula (V) having a high enantiomeric purity of ee≥9%:

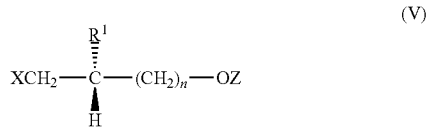

wherein X is $OR_x$, $R_x$ is a protective group, and Z is H or a protective group and n is an integer selected from 2-8; under a reduction condition or a cross-coupling condition to prepare said compound of formula (II), wherein said compound of formula (H) has a high enantiomeric purity of ee≥99%.

7. The process of claim 6, wherein said compound of formula (V) is prepared by (a) treating a compound of formula (III)

where n and Z have the same meanings as for formula (V); under a Zr-catalyzed asymmetric carboalumination condition to prepare intermediate (II);

(b) treating said intermediate (H) with a reagent to prepare said compound of formula (V) having a low enantiomeric purity of ee<99%; and (c) purifying the compound of formula (V) having said low enantiomeric purity under a lipase-catalyzed acetylation reaction condition to prepare said compound of formula (V) having a high enantiomeric purity of ee≥99%.

8. The process of claim 6, wherein said reduction condition comprises $LiAlH_4$.

9. The process of claim 6, wherein said cross-coupling condition is a Cu-, Ni-, or Pd-catalyzed cross-coupling reaction.

10. The process of claim 6, wherein said cross-coupling condition is a Cu-catalyzed cross-coupling reaction with an alkylmagnesium halide reagent.

11. The process of claim 10, wherein said cross-coupling condition comprises MeMgBr and $Li_2CuCl_4$.

12. The process of claim 10, wherein said cross-coupling condition comprises EtMgCl, $CuCl_2$, and 1-phenylpropyne.

13. The process of claim 6, wherein said cross-coupling condition is a Pd-catalyzed Negishi coupling reaction condition.

14. The process of claim 13, wherein said Pd-catalyzed Negishi coupling reaction condition comprises vinyl bromide and $Pd(DPEphos)Cl_2$.

15. The process of claim 2, wherein said Zr-catalyzed asymmetric carboalumination condition comprises a trialkylaluminium reagent, an aluminoxane, and $(-)-(NMI)_2ZrCl_2$ in a solvent.

16. The process of claim 15, wherein said aluminoxane is methylaluminoxane.

17. The process of claim 16, wherein said trialkylaluminium is $Me_3Al$.

18. The process of claim 15, wherein said aluminoxane is isobutylaluminoxane.

19. The process of claim 18, wherein said trialkylaluminium is $Et_3Al$ or $^nPr_3Al$.

20. The process of claim 12, wherein said solvent is $CH_2Cl_2$.

* * * * *